(12) United States Patent
Lassen et al.

(10) Patent No.: US 11,534,424 B2
(45) Date of Patent: Dec. 27, 2022

(54) COMPOUNDS AND METHODS FOR TREATMENT OF PRIMARY BILIARY CHOLANGITIS

(71) Applicant: Arena Pharmaceuticals, Inc., San Diego, CA (US)

(72) Inventors: Cheryl Geraldine Lassen, Zurich (CH); Robert Mark Jones, San Mateo, CA (US); Que Liu, San Diego, CA (US); Ronald J. Christopher, Carlsbad, CA (US)

(73) Assignee: Arena Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/486,464

(22) PCT Filed: Feb. 16, 2018

(86) PCT No.: PCT/US2018/000091
§ 371 (c)(1),
(2) Date: Aug. 15, 2019

(87) PCT Pub. No.: WO2018/151873
PCT Pub. Date: Aug. 23, 2018

(65) Prior Publication Data
US 2020/0000770 A1 Jan. 2, 2020

Related U.S. Application Data

(60) Provisional application No. 62/459,916, filed on Feb. 16, 2017, provisional application No. 62/502,129, filed on May 5, 2017, provisional application No. 62/506,906, filed on May 16, 2017.

(51) Int. Cl.
*A61K 31/404* (2006.01)
*A61P 1/16* (2006.01)
*A61K 31/575* (2006.01)

(52) U.S. Cl.
CPC .............. *A61K 31/404* (2013.01); *A61P 1/16* (2018.01); *A61K 31/575* (2013.01)

(58) Field of Classification Search
CPC .... A61K 31/404; A61K 31/575; A61K 45/06; A61P 1/16
See application file for complete search history.

(56) References Cited

U.S. PATENT DOCUMENTS

| | | |
|---|---|---|
| 3,206,470 A | 9/1965 | William et al. |
| 3,503,963 A | 3/1970 | Schweizer et al. |
| 3,592,932 A | 7/1971 | Duerr et al. |
| 3,598,801 A | 8/1971 | Beffa et al. |
| 3,608,087 A | 9/1971 | Patchett et al. |
| 3,686,238 A | 8/1972 | Zaffaroni et al. |
| 3,690,834 A | 9/1972 | Goldstein et al. |
| 3,849,420 A | 11/1974 | Tong |
| 3,852,434 A | 12/1974 | Kahan et al. |
| 3,862,117 A | 1/1975 | Leverenz |
| 3,887,329 A | 6/1975 | Hegar et al. |
| 3,948,914 A | 4/1976 | Fischer |
| 3,966,744 A | 6/1976 | Goldstein et al. |
| 3,966,764 A | 6/1976 | Goldstein et al. |
| 3,975,384 A | 8/1976 | Narr et al. |
| 3,984,411 A | 10/1976 | Claverie et al. |
| 4,057,559 A | 11/1977 | Asselin et al. |
| 4,101,541 A | 7/1978 | Petitpierre et al. |
| 4,139,705 A | 2/1979 | Dunbar et al. |
| 4,189,427 A | 2/1980 | Komorowski |
| 4,189,579 A | 2/1980 | Dunbar et al. |
| 4,242,507 A | 12/1980 | Itoh et al. |
| 4,267,174 A | 5/1981 | Berger et al. |
| 4,273,870 A | 6/1981 | Endo et al. |
| 4,275,148 A | 6/1981 | Endo et al. |
| 4,343,804 A | 8/1982 | Munison et al. |
| 4,397,848 A | 8/1983 | Bosies et al. |

(Continued)

FOREIGN PATENT DOCUMENTS

| | | |
|---|---|---|
| BE | 829845 | 12/1975 |
| BE | 868796 | 1/1979 |

(Continued)

OTHER PUBLICATIONS

Cheung et al., Aliment. Pharmacol. Ther., publ. online Nov. 12, 2015, vol. 43, pp. 283-293 (Year: 2015).*
Bergasa et al., Bailliere's Clinical Gastroenterology, , publ. 2000, vol. 14(4), pp. 643-655 (Year: 2000).*
Rudic et al., Cochrane Database Syst. Rev., publ. 2012. pp. 1-139 (Year: 2012).*
Combes et al., Hepatology, publ. 2005, vol. 42(5), pp. 1184-1193 (Year: 2005).*
"2.9.26 Specific Surface Area by Gas Adsorption," European Pharmacopoeia, 2811-2814.

(Continued)

*Primary Examiner* — Sarah Pihonak
(74) *Attorney, Agent, or Firm* — Fish & Richardson P.C.

(57) ABSTRACT

The present invention relates to, inter alia, methods of treatment and combinations of (R)-2-(7-(4-cyclopentyl-3-(tri-fluoromethyl)benzyloxy)-1,2,3,4-tetrahydrocyclopenta[b]indol-3-yl)acetic acid (Compound 1) useful for the treatment of primary biliary cholangitis (PBC). In some embodiments, the methods further comprise administering Compound 1, or a pharmaceutically salt, solvate, or hydrate thereof, in combination with a compound selected from the group consisting of: an antihistamine (diphenhydramine), cholestyramine (questran, prevalite), rifampin, an opioid antagonist (naloxone), pilocarpine (isopto carpine, salagen), cevimeline (evoxac), calcium and/or vitamin D supplement, and vitamin A, D, E and/or K supplement. Other embodiments, relate to titration packages for enabling compliance with a regimen of changing dosage of a medication over a period of time for the treatment of primary biliary cholangitis (PBC).

18 Claims, 7 Drawing Sheets

(56) References Cited

U.S. PATENT DOCUMENTS

| | | |
|---|---|---|
| 4,476,248 A | 10/1984 | Gordon et al. |
| 4,493,726 A | 1/1985 | Burdeska et al. |
| 4,517,183 A | 5/1985 | Bosies et al. |
| 4,612,376 A | 9/1986 | Takaya et al. |
| 4,643,995 A | 2/1987 | Engel et al. |
| 4,766,213 A | 8/1988 | Juraszyk et al. |
| 4,782,076 A | 11/1988 | Mobilio et al. |
| 4,810,699 A | 3/1989 | Sabatucci et al. |
| 4,880,932 A | 11/1989 | Moriya et al. |
| 5,221,678 A | 6/1993 | Atkinson et al. |
| 5,571,815 A | 11/1996 | Schaper et al. |
| 5,624,941 A | 4/1997 | Barth et al. |
| 5,691,364 A | 11/1997 | Buckman et al. |
| 5,776,967 A | 7/1998 | Kreft et al. |
| 5,830,911 A | 11/1998 | Failli et al. |
| 5,849,759 A | 12/1998 | Amaiz et al. |
| 5,948,786 A | 9/1999 | Fujiwara et al. |
| 5,952,504 A | 9/1999 | Yoo et al. |
| 5,962,479 A | 10/1999 | Chen |
| 6,008,234 A | 12/1999 | Kochany et al. |
| 6,060,478 A | 5/2000 | Gilligan |
| 6,107,301 A | 8/2000 | Aldrich et al. |
| 6,187,777 B1 | 2/2001 | Norman et al. |
| 6,191,149 B1 | 2/2001 | Chokai et al. |
| 6,218,431 B1 | 4/2001 | Schoen et al. |
| 6,239,126 B1 | 5/2001 | Kelly et al. |
| 6,267,985 B1 | 7/2001 | Chen et al. |
| 6,294,671 B1 | 9/2001 | Frietze |
| 6,350,750 B1 | 2/2002 | Den Hartog et al. |
| 6,410,583 B1 | 6/2002 | Labelle et al. |
| 6,414,002 B1 | 7/2002 | Cheng et al. |
| 6,506,762 B1 | 1/2003 | Horvath et al. |
| 6,525,064 B1 | 2/2003 | Dellaria et al. |
| 6,545,016 B1 | 4/2003 | Dellaria et al. |
| 6,545,017 B1 | 4/2003 | Dellaria et al. |
| 6,552,192 B1 | 4/2003 | Hanuš et al. |
| 6,569,879 B2 | 5/2003 | Liu et al. |
| 6,583,154 B1 | 6/2003 | Norman et al. |
| 6,620,821 B2 | 9/2003 | Robl et al. |
| 6,660,744 B1 | 12/2003 | Hirst et al. |
| 6,713,508 B2 | 3/2004 | Sahoo et al. |
| 6,787,542 B2 | 9/2004 | Wang et al. |
| 6,844,351 B1 | 1/2005 | Chen et al. |
| 6,849,636 B2 | 2/2005 | Waddell et al. |
| 6,956,047 B1 | 10/2005 | Chen et al. |
| 6,960,692 B2 | 11/2005 | Kohno et al. |
| 7,056,942 B2 | 6/2006 | Hildesheim et al. |
| 7,057,046 B2 | 6/2006 | Sher et al. |
| 7,083,933 B1 | 8/2006 | Griffin |
| 7,098,235 B2 | 8/2006 | Sher et al. |
| 7,132,426 B2 | 11/2006 | Jones et al. |
| 7,250,441 B2 | 7/2007 | Gopalsamy et al. |
| 7,276,249 B2 | 10/2007 | Ryde et al. |
| 7,417,039 B2 | 8/2008 | Davis |
| 7,425,630 B2 | 9/2008 | Gharbaoui et al. |
| 7,470,699 B2 | 12/2008 | Jones et al. |
| 7,625,906 B2 | 12/2009 | Jones et al. |
| 7,763,278 B2 | 7/2010 | Cooper et al. |
| 7,812,159 B2 | 10/2010 | Gharbaoui et al. |
| 7,838,525 B2 | 11/2010 | Jones et al. |
| 8,293,751 B2 | 10/2012 | Jones et al. |
| 8,362,248 B2 | 1/2013 | Jones et al. |
| 8,410,119 B2 | 4/2013 | Jones et al. |
| 8,415,484 B2 | 4/2013 | Jones et al. |
| 8,580,841 B2 | 11/2013 | Jones et al. |
| 8,853,419 B2 | 10/2014 | Montalban et al. |
| 9,085,581 B2 | 7/2015 | Jones et al. |
| 9,108,969 B2 | 8/2015 | Jones et al. |
| 9,126,932 B2 | 9/2015 | Jones et al. |
| 9,175,320 B2 | 11/2015 | Montalban et al. |
| 9,447,041 B2 | 9/2016 | Montalban et al. |
| 9,522,133 B2 | 12/2016 | Jones et al. |
| 10,301,262 B2 | 5/2019 | Blackburn et al. |
| 10,676,435 B2 | 6/2020 | Blackburn |
| 11,007,175 B2 | 5/2021 | Glicklich et al. |
| 11,091,435 B2 | 8/2021 | Blackburn et al. |
| 11,149,292 B2 | 10/2021 | Montalban et al. |
| 2002/0058026 A1 | 5/2002 | Hammerly |
| 2002/0137755 A1 | 9/2002 | Bilodeau et al. |
| 2002/0156081 A1 | 10/2002 | Hirst et al. |
| 2003/0083269 A1 | 5/2003 | Brouillette et al. |
| 2003/0211421 A1 | 11/2003 | Hanabata et al. |
| 2003/0224058 A1 | 12/2003 | Ryde et al. |
| 2004/0110241 A1 | 6/2004 | Segal |
| 2004/0224941 A1 | 11/2004 | Seko et al. |
| 2004/0254222 A1 | 12/2004 | Kohno et al. |
| 2005/0004114 A1 | 1/2005 | Whitehouse et al. |
| 2005/0009786 A1 | 1/2005 | Pan et al. |
| 2005/0014724 A1 | 1/2005 | Marsilje et al. |
| 2005/0014725 A1 | 1/2005 | Mi |
| 2005/0014728 A1 | 1/2005 | Pan et al. |
| 2005/0033055 A1 | 2/2005 | Bugianesi et al. |
| 2005/0070562 A1 | 3/2005 | Jones et al. |
| 2005/0182067 A1 | 8/2005 | Balan et al. |
| 2005/0197353 A1 | 9/2005 | Ritzeler et al. |
| 2005/0209251 A1 | 9/2005 | Linker et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |
| 2006/0122222 A1 | 6/2006 | Whitehouse et al. |
| 2006/0154866 A1 | 7/2006 | Cbu et al. |
| 2006/0155128 A1 | 7/2006 | Jones et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2007/0010494 A1 | 1/2007 | Ehrhardt et al. |
| 2007/0043014 A1 | 2/2007 | Doherty et al. |
| 2007/0060573 A1 | 3/2007 | Wortmann et al. |
| 2007/0066590 A1 | 3/2007 | Jones et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0149595 A1 | 6/2007 | Tanaka et al. |
| 2007/0149597 A1 | 6/2007 | Nishi et al. |
| 2007/0167413 A1 | 7/2007 | Srinivas et al. |
| 2007/0167425 A1 | 7/2007 | Nakade et al. |
| 2007/0167473 A1 | 7/2007 | Jones et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0225351 A1 | 9/2007 | Lippa et al. |
| 2007/0244155 A1 | 10/2007 | Sharma et al. |
| 2007/0254886 A1 | 11/2007 | Habashita et al. |
| 2007/0259928 A1 | 11/2007 | Yoshida et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0004265 A1 | 1/2009 | Misselwitz et al. |
| 2009/0012093 A1 | 1/2009 | Fukatsu et al. |
| 2009/0036434 A1 | 2/2009 | Jones et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0203676 A1 | 8/2009 | Barba et al. |
| 2009/0253802 A1* | 10/2009 | Kaneko ............ A61P 1/00 514/654 |
| 2009/0270409 A1 | 10/2009 | Alper et al. |
| 2009/0286816 A1 | 11/2009 | Jones et al. |
| 2009/0325907 A1 | 12/2009 | Kohno et al. |
| 2010/0004272 A1 | 1/2010 | Jones et al. |
| 2010/0029650 A1 | 2/2010 | Fang et al. |
| 2010/0160359 A1 | 6/2010 | Jones et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0000153 A1 | 1/2011 | Albert |
| 2011/0039933 A1* | 2/2011 | Evindar ............ A61P 1/16 514/563 |
| 2011/0082134 A1 | 4/2011 | Jones et al. |

(56) References Cited

U.S. PATENT DOCUMENTS

| | | | |
|---|---|---|---|
| 2011/0105471 A1 | 5/2011 | Burcham | |
| 2011/0112060 A1 | 5/2011 | Jones et al. | |
| 2011/0130409 A1* | 6/2011 | Jones | A61P 9/00 514/255.05 |
| 2011/0159096 A1 | 6/2011 | Duran Lopez et al. | |
| 2011/0160243 A1 | 6/2011 | Jones et al. | |
| 2011/0230457 A1 | 9/2011 | Berghansen et al. | |
| 2012/0064060 A1 | 3/2012 | Habashita et al. | |
| 2012/0295947 A1 | 11/2012 | Montalban et al. | |
| 2012/0329848 A1 | 12/2012 | Jones et al. | |
| 2013/0023494 A1 | 1/2013 | Jones et al. | |
| 2013/0023527 A1 | 1/2013 | Jones et al. | |
| 2013/0184307 A1 | 7/2013 | Jones et al. | |
| 2013/0203807 A1 | 8/2013 | Tarcic et al. | |
| 2014/0038889 A1 | 2/2014 | Jones | |
| 2014/0038987 A1 | 2/2014 | Jones et al. | |
| 2014/0051629 A1 | 2/2014 | Jones et al. | |
| 2014/0155654 A1 | 6/2014 | Preda et al. | |
| 2014/0350115 A1 | 11/2014 | Kostik et al. | |
| 2014/0357690 A1 | 12/2014 | Montalban et al. | |
| 2015/0336966 A1 | 8/2015 | Jones et al. | |
| 2015/0284399 A1 | 10/2015 | Jones et al. | |
| 2015/0335618 A1 | 11/2015 | Jones et al. | |
| 2016/0016904 A1 | 1/2016 | Montalban et al. | |
| 2016/0038506 A1 | 2/2016 | Podolski et al. | |
| 2017/0159088 A1 | 6/2017 | Montalban et al. | |
| 2017/0217885 A1 | 8/2017 | Jones et al. | |
| 2018/0186738 A1 | 7/2018 | Blackburn et al. | |
| 2018/0263958 A1 | 9/2018 | Glicklich et al. | |
| 2019/0135752 A1 | 5/2019 | Jones et al. | |
| 2019/0330153 A1 | 10/2019 | Blackburn et al. | |
| 2020/0016121 A1 | 1/2020 | Lassen et al. | |
| 2020/0361869 A1 | 11/2020 | Blackburn et al. | |
| 2020/0407316 A1 | 12/2020 | Jones et al. | |
| 2021/0228545 A1 | 7/2021 | Christopher et al. | |
| 2021/0338636 A1 | 11/2021 | Glicklich et al. | |
| 2021/0386706 A1 | 12/2021 | Adams | |
| 2022/0002244 A1 | 1/2022 | Blackburn et al. | |
| 2022/0023258 A1 | 1/2022 | Naik | |
| 2022/0142977 A1 | 5/2022 | Naik | |

FOREIGN PATENT DOCUMENTS

| | | |
|---|---|---|
| CN | 101980704 | 2/2011 |
| CN | 101981030 | 2/2011 |
| CN | 102197038 | 9/2011 |
| CN | 105816453 | 8/2016 |
| CN | 106278999 | 1/2017 |
| DE | 2048375 | 4/1971 |
| DE | 2223644 | 11/1972 |
| DE | 2356644 | 5/1974 |
| DE | 2341925 | 3/1975 |
| DE | 2460238 | 7/1975 |
| DE | 2503136 | 7/1975 |
| DE | 2831850 | 2/1980 |
| DE | 3334455 | 9/1984 |
| DE | 3406329 | 8/1985 |
| DE | 3601196 | 7/1987 |
| EP | 0014976 | 9/1980 |
| EP | 0053678 | 10/1981 |
| EP | 0055693 | 7/1982 |
| EP | 0123402 | 10/1984 |
| EP | 0149088 | 12/1984 |
| EP | 0154190 | 9/1985 |
| EP | 0468785 | 1/1992 |
| EP | 0565488 | 10/1993 |
| EP | 0604800 | 7/1994 |
| EP | 1650186 | 4/2006 |
| EP | 1826197 | 8/2007 |
| EP | 2003132 | 12/2008 |
| EP | 1772145 | 3/2011 |
| EP | 2017263 | 11/2011 |
| FR | 1551400 | 12/1968 |
| GB | 1436893 | 5/1976 |
| JP | 2007262009 | 10/2007 |
| NL | 66144961 | 4/1967 |
| WO | WO 1991/06537 | 5/1991 |
| WO | WO 1997/14674 | 4/1997 |
| WO | WO 2000/035886 | 6/2000 |
| WO | WO 2000/055153 | 9/2000 |
| WO | WO 2000/064888 | 11/2000 |
| WO | WO 2001/060807 | 2/2001 |
| WO | WO 2001/022938 | 4/2001 |
| WO | WO 2001/023387 | 4/2001 |
| WO | WO 2001/023388 | 4/2001 |
| WO | WO 2001/025210 | 4/2001 |
| WO | WO 2001/027107 | 4/2001 |
| WO | WO 2001/037831 | 5/2001 |
| WO | WO 2001/046204 | 6/2001 |
| WO | WO 2001/047887 | 7/2001 |
| WO | WO 2001/049677 | 7/2001 |
| WO | WO 2001/053263 | 7/2001 |
| WO | WO 2001/058900 | 8/2001 |
| WO | WO 2001/060870 | 8/2001 |
| WO | WO 2001/062233 | 8/2001 |
| WO | WO 2001/076573 | 10/2001 |
| WO | WO 2001/085699 | 11/2001 |
| WO | WO 2001/087829 | 11/2001 |
| WO | WO 2001/087892 | 11/2001 |
| WO | WO 2001/090082 | 11/2001 |
| WO | WO 2002/002539 | 1/2002 |
| WO | WO 2002/002549 | 1/2002 |
| WO | WO 2002/006237 | 1/2002 |
| WO | WO 2002/006274 | 1/2002 |
| WO | WO 2002/008188 | 1/2002 |
| WO | WO 2002/019975 | 3/2002 |
| WO | WO 2002/024169 | 3/2002 |
| WO | WO 2002/032408 | 4/2002 |
| WO | WO 2002/032893 | 4/2002 |
| WO | WO 2002/039987 | 5/2002 |
| WO | WO 2002/040451 | 5/2002 |
| WO | WO 2002/040456 | 5/2002 |
| WO | WO 2002/040458 | 5/2002 |
| WO | WO 2002/040480 | 5/2002 |
| WO | WO 2002/044362 | 6/2002 |
| WO | WO 2002/045652 | 6/2002 |
| WO | WO 2002/050071 | 6/2002 |
| WO | WO 2002/059083 | 8/2002 |
| WO | WO 2002/060388 | 8/2002 |
| WO | WO 2002/064094 | 8/2002 |
| WO | WO 2002/064616 | 8/2002 |
| WO | WO 2002/070485 | 9/2002 |
| WO | WO 2002/072101 | 9/2002 |
| WO | WO 2002/081454 | 10/2002 |
| WO | WO 2002/085892 | 10/2002 |
| WO | WO 2002/092068 | 11/2002 |
| WO | WO 2002/098864 | 12/2002 |
| WO | WO 2002/098878 | 12/2002 |
| WO | WO 2002/102313 | 12/2002 |
| WO | WO 2003/000666 | 1/2003 |
| WO | WO 2003/002544 | 1/2003 |
| WO | WO 2003/004498 | 1/2003 |
| WO | WO 2.003/018556 | 3/2003 |
| WO | WO 2003/026661 | 4/2003 |
| WO | WO 2003/029205 | 4/2003 |
| WO | WO 2003/032989 | 4/2003 |
| WO | WO 2003/050117 | 6/2003 |
| WO | WO 2003/051822 | 6/2003 |
| WO | WO 2003/057689 | 7/2003 |
| WO | WO 2003/059378 | 7/2003 |
| WO | WO 2003/061663 | 7/2003 |
| WO | WO 2003/062252 | 7/2003 |
| WO | WO 2003/073986 | 9/2003 |
| WO | WO 2003/074008 | 9/2003 |
| WO | WO 2003/076418 | 9/2003 |
| WO | WO 2003/077656 | 9/2003 |
| WO | WO 2003/080070 | 10/2003 |
| WO | WO 2003/087064 | 10/2003 |
| WO | WO 2003/088962 | 10/2003 |
| WO | WO 2003/093269 | 11/2003 |
| WO | WO 2003/094845 | 11/2003 |
| WO | WO 2003/061567 | 12/2003 |
| WO | WO 2003/103632 | 12/2003 |

(56) References Cited

FOREIGN PATENT DOCUMENTS

| | | |
|---|---|---|
| WO | WO 2003/103633 | 12/2003 |
| WO | WO 2003/103640 | 12/2003 |
| WO | WO 2003/104208 | 12/2003 |
| WO | WO 2003/105763 | 12/2003 |
| WO | WO 2003/105771 | 12/2003 |
| WO | WO 2003/106450 | 12/2003 |
| WO | WO 2004/000762 | 12/2003 |
| WO | WO 2004/000819 | 12/2003 |
| WO | WO 2004/000843 | 12/2003 |
| WO | WO 2.004/009596 | 1/2004 |
| WO | WO 2004/002495 | 1/2004 |
| WO | WO 2004/004777 | 1/2004 |
| WO | WO 2004/004778 | 1/2004 |
| WO | WO 2004/009597 | 1/2004 |
| WO | WO 2004/009602 | 1/2004 |
| WO | WO 2004/010936 | 2/2004 |
| WO | WO 2004/010992 | 2/2004 |
| WO | WO 2004/013633 | 2/2004 |
| WO | WO 2004/014871 | 2/2004 |
| WO | WO 2004/017896 | 3/2004 |
| WO | WO 2004/019869 | 3/2004 |
| WO | WO 2004/020408 | 3/2004 |
| WO | WO 2004/020409 | 3/2004 |
| WO | WO 2004/024943 | 3/2004 |
| WO | WO 2004/029204 | 4/2004 |
| WO | WO 2004/031189 | 4/2004 |
| WO | WO 2004/033431 | 4/2004 |
| WO | WO 2004/033710 | 4/2004 |
| WO | WO 2004/035588 | 4/2004 |
| WO | WO 2004/037823 | 5/2004 |
| WO | WO 2004/041164 | 5/2004 |
| WO | WO 2004/056748 | 7/2004 |
| WO | WO 2004/056825 | 7/2004 |
| WO | WO 2004/056829 | 7/2004 |
| WO | WO 2004/058174 | 7/2004 |
| WO | WO 2004/058727 | 7/2004 |
| WO | WO 2004/062665 | 7/2004 |
| WO | WO 2004/064806 | 8/2004 |
| WO | WO 2004/065380 | 8/2004 |
| WO | WO 2004/066963 | 8/2004 |
| WO | WO 2.004/074218 | 9/2004 |
| WO | WO 2004/058149 | 9/2004 |
| WO | WO 2004/074297 | 9/2004 |
| WO | WO 2004/076413 | 9/2004 |
| WO | WO 2004/010949 | 10/2004 |
| WO | WO 2004/071442 | 10/2004 |
| WO | WO 2004/085401 | 10/2004 |
| WO | WO 2004/096752 | 11/2004 |
| WO | WO 2004/096757 | 11/2004 |
| WO | WO 2004/098583 | 11/2004 |
| WO | WO 2004/099144 | 11/2004 |
| WO | WO 2004/103279 | 12/2004 |
| WO | WO 2004/103306 | 12/2004 |
| WO | WO 2004/103309 | 12/2004 |
| WO | WO 2004/103997 | 12/2004 |
| WO | WO 2004/104205 | 12/2004 |
| WO | WO 2004/110368 | 12/2004 |
| WO | WO 2004/110979 | 12/2004 |
| WO | WO 2004/111000 | 12/2004 |
| WO | WO 2004/113330 | 12/2004 |
| WO | WO 2005/000833 | 1/2005 |
| WO | WO 2005/007647 | 1/2005 |
| WO | WO 2005/007658 | 1/2005 |
| WO | WO 2005/016894 | 2/2005 |
| WO | WO 2005/020920 | 3/2005 |
| WO | WO 2005/021503 | 3/2005 |
| WO | WO 2005/023762 | 3/2005 |
| WO | WO 2005/025554 | 3/2005 |
| WO | WO 2005/026148 | 3/2005 |
| WO | WO 2005/020882 | 4/2005 |
| WO | WO 2005/030127 | 4/2005 |
| WO | WO 2005/030129 | 4/2005 |
| WO | WO 2005/030751 | 4/2005 |
| WO | WO 2005/032465 | 4/2005 |
| WO | WO 2005/033099 | 4/2005 |
| WO | WO 2005/035525 | 4/2005 |
| WO | WO 2005/037215 | 4/2005 |
| WO | WO 2005/040095 | 5/2005 |
| WO | WO 2005/041899 | 5/2005 |
| WO | WO 2005/042488 | 5/2005 |
| WO | WO 2005/044780 | 5/2005 |
| WO | WO 2005/046603 | 5/2005 |
| WO | WO 2005/047297 | 5/2005 |
| WO | WO 2.005/058849 | 6/2005 |
| WO | WO 2005/049033 | 6/2005 |
| WO | WO 2005/058315 | 6/2005 |
| WO | WO 2005/058848 | 6/2005 |
| WO | WO 2005/061489 | 7/2005 |
| WO | WO 2005/063750 | 7/2005 |
| WO | WO 2005/070886 | 8/2005 |
| WO | WO 2005/072530 | 8/2005 |
| WO | WO 2005/075426 | 8/2005 |
| WO | WO 2005/079788 | 9/2005 |
| WO | WO 2005/080330 | 9/2005 |
| WO | WO 2005/082089 | 9/2005 |
| WO | WO 2005/082841 | 9/2005 |
| WO | WO 2005/085179 | 9/2005 |
| WO | WO 2005/090348 | 9/2005 |
| WO | WO 2005/097745 | 10/2005 |
| WO | WO 2005/100365 | 10/2005 |
| WO | WO 2005/058295 | 11/2005 |
| WO | WO 2005/117909 | 12/2005 |
| WO | WO 2005/121121 | 12/2005 |
| WO | WO 2005/123677 | 12/2005 |
| WO | WO 2006/001463 | 1/2006 |
| WO | WO 2006/009092 | 1/2006 |
| WO | WO 2006/010379 | 2/2006 |
| WO | WO 2006/011554 | 2/2006 |
| WO | WO 2006/013948 | 2/2006 |
| WO | WO 2006/020951 | 2/2006 |
| WO | WO 2006/010544 | 3/2006 |
| WO | WO 2006/034337 | 3/2006 |
| WO | WO 2006/034446 | 3/2006 |
| WO | WO 2006/039325 | 4/2006 |
| WO | WO 2006/040966 | 4/2006 |
| WO | WO 2006/043149 | 4/2006 |
| WO | WO 2006/043490 | 4/2006 |
| WO | WO 2006/047195 | 5/2006 |
| WO | WO 2006/047516 | 5/2006 |
| WO | WO 2006/050946 | 5/2006 |
| WO | WO 2006/052566 | 5/2006 |
| WO | WO 2006/064757 | 6/2006 |
| WO | WO 2006/067531 | 6/2006 |
| WO | WO 2006/067532 | 6/2006 |
| WO | WO 2006/070208 | 7/2006 |
| WO | WO 2006/076231 | 7/2006 |
| WO | WO 2006/076243 | 7/2006 |
| WO | WO 2006/076455 | 7/2006 |
| WO | WO 2006/078992 | 7/2006 |
| WO | WO 2006/079406 | 8/2006 |
| WO | WO 2006/083491 | 8/2006 |
| WO | WO 2006/088944 | 8/2006 |
| WO | WO 2006/100631 | 9/2006 |
| WO | WO 2006/100633 | 9/2006 |
| WO | WO 2006/100635 | 9/2006 |
| WO | WO 2006/063033 | 11/2006 |
| WO | WO 2006/131336 | 12/2006 |
| WO | WO 2006/137019 | 12/2006 |
| WO | WO 2006/137509 | 12/2006 |
| WO | WO 2007/003964 | 1/2007 |
| WO | WO 2007/005673 | 1/2007 |
| WO | WO 2007/024922 | 3/2007 |
| WO | WO 2007/035355 | 3/2007 |
| WO | WO 2007/037196 | 4/2007 |
| WO | WO 2007/039470 | 4/2007 |
| WO | WO 2007/060626 | 5/2007 |
| WO | WO 2007/080542 | 7/2007 |
| WO | WO 2007/083089 | 7/2007 |
| WO | WO 2007/085451 | 8/2007 |
| WO | WO 2007/086001 | 8/2007 |
| WO | WO 2007/089335 | 8/2007 |
| WO | WO 2007/091396 | 8/2007 |
| WO | WO 2007/091501 | 8/2007 |
| WO | WO 2007/092638 | 8/2007 |

(56) References Cited

FOREIGN PATENT DOCUMENTS

| | | |
|---|---|---|
| WO | WO 2007/098474 | 8/2007 |
| WO | WO 2007/100617 | 9/2007 |
| WO | WO 2007/109330 | 9/2007 |
| WO | WO 2007/109334 | 9/2007 |
| WO | WO 2007/095561 | 10/2007 |
| WO | WO 2007/115820 | 10/2007 |
| WO | WO 2007/116866 | 10/2007 |
| WO | WO 2007/120689 | 10/2007 |
| WO | WO 2007/120702 | 10/2007 |
| WO | WO 2007/061458 | 11/2007 |
| WO | WO 2007/092190 | 11/2007 |
| WO | WO 2007/129473 | 11/2007 |
| WO | WO 2007/129745 | 11/2007 |
| WO | WO 2007/132307 | 11/2007 |
| WO | WO 2008/005569 | 1/2008 |
| WO | WO 2008/005576 | 1/2008 |
| WO | WO 2008/008895 | 1/2008 |
| WO | WO 2008/016674 | 2/2008 |
| WO | WO 2008/018427 | 2/2008 |
| WO | WO 2008/019090 | 2/2008 |
| WO | WO 2008/023783 | 2/2008 |
| WO | WO 2008/024196 | 2/2008 |
| WO | WO 2008/016692 | 3/2008 |
| WO | WO 2008/025798 | 3/2008 |
| WO | WO 2008/028937 | 3/2008 |
| WO | WO 2008/029371 | 3/2008 |
| WO | WO 2008/030843 | 3/2008 |
| WO | WO 2008/035239 | 3/2008 |
| WO | WO 2008/029306 | 5/2008 |
| WO | WO 2008/0763 56 | 6/2008 |
| WO | WO 2008/070692 | 6/2008 |
| WO | WO 2008/074820 | 6/2008 |
| WO | WO 2008/074821 | 6/2008 |
| WO | WO 2008/076243 | 6/2008 |
| WO | WO 2008/079382 | 7/2008 |
| WO | WO 2008/089015 | 7/2008 |
| WO | WO 2008/091967 | 7/2008 |
| WO | WO 2008/114157 | 9/2008 |
| WO | WO 2008/128832 | 10/2008 |
| WO | WO 2008/128951 | 10/2008 |
| WO | WO 2008/097819 | 11/2008 |
| WO | WO 2008/137435 | 11/2008 |
| WO | WO 2008/152149 | 12/2008 |
| WO | WO 2009/019167 | 2/2009 |
| WO | WO 2009/019506 | 2/2009 |
| WO | WO 2009/011850 | 3/2009 |
| WO | WO 2009/038974 | 3/2009 |
| WO | WO 2009/064250 | 5/2009 |
| WO | WO 2009/078983 | 6/2009 |
| WO | WO 2009/094157 | 7/2009 |
| WO | WO 2009/103552 | 8/2009 |
| WO | WO 2009/115954 | 9/2009 |
| WO | WO 2009/12653 5 | 10/2009 |
| WO | WO 2009/125434 | 10/2009 |
| WO | WO 2009/126245 | 10/2009 |
| WO | WO 2009/151529 | 12/2009 |
| WO | WO 2009/151621 | 12/2009 |
| WO | WO 2009/151626 | 12/2009 |
| WO | WO 2010/011316 | 1/2010 |
| WO | WO-2010011316 A1 * 1/2010 ........... C07C 211/27 |
| WO | WO 2010/027431 | 3/2010 |
| WO | WO 2010/072703 | 7/2010 |
| WO | WO 2010/074271 | 7/2010 |
| WO | WO 2010/075239 | 7/2010 |
| WO | WO 2010/075271 | 7/2010 |
| WO | WO 2010/075273 | 7/2010 |
| WO | WO 2010/084944 | 7/2010 |
| WO | WO 2010/093704 | 8/2010 |
| WO | WO 2011/005290 | 1/2011 |
| WO | WO 2011/005295 | 1/2011 |
| WO | WO 2011/005929 | 1/2011 |
| WO | WO 2011/008663 | 1/2011 |
| WO | WO 2011/030139 | 3/2011 |
| WO | WO 2011/059784 | 5/2011 |
| WO | WO 2011/094008 | 8/2011 |
| WO | WO 2011/109471 | 9/2011 |
| WO | WO 2011/127051 | 10/2011 |
| WO | WO 2012/015758 | 2/2012 |
| WO | WO 2012/040279 | 3/2012 |
| WO | WO 2012/109108 | 8/2012 |
| WO | WO 2012/135570 | 10/2012 |
| WO | WO 2012/145361 | 10/2012 |
| WO | WO 2012/145603 | 10/2012 |
| WO | WO 2012/145604 | 10/2012 |
| WO | WO 2012/170702 | 12/2012 |
| WO | WO 2013/055910 | 4/2013 |
| WO | WO 2014/136282 | 9/2014 |
| WO | WO 2016/112075 | 7/2016 |
| WO | WO 2016/209809 | 12/2016 |
| WO | WO 2018/151834 | 8/2018 |
| WO | WO 2018/151873 | 8/2018 |
| WO | WO 2020/146529 | 7/2020 |

OTHER PUBLICATIONS

Actelion, Clinical Trials.gov, "Multicenter, Randomized, Double-blind, Placebo-controlled, Phase IIa Study to Evaluate the Efficacy, Safety, and Tolerability of ACT-128800, an S1P1 Receptor Agonist, Administered for 6 Weeks to Subjects With Moderate to Severe Chronic Plaque Psoriasis" http://clinicaltrials.gov/ct2/show/NCT00852670, 2009.

Allende et al., "Sphingosine-1-phosphate lyase deficiency produces a pro-inflammatory response while impairing neutrophil trafficking," J Biol Chem; 2011, 286:7348-58.

American Gastroenterological Assoc. IBD emerges as a global disease, Jan. 5, 2012, ScienceDaily. www.sciencedaily.com/releases/2012/01/120104135402.htm. Accessed Jan. 7, 2015.

Arbiser, "Why targeted therapy hasn't worked in advanced cancer," J Clinical Invest., Oct. 2007, 117(10):2762-2765.

Avoiding Fatal Responses to Flu Infection, ScienceDaily, http://www.sciencedaily.com/releases/2011/09/110915134410.htm, Sep. 15, 2011, 2 pages.

Balatoni et al., "FTY720 sustains and restores neuronal function in the DA rat model of MOG-induced experimental autoimmunue encephalomyelitis," Brain Res. Bull., 2007, 74:307-316.

Bar-Haim et al., "Interrelationship between Dendritic Cell Trafficking and Francisella tularensis Dissemination following Airway Infection," PLoS Pathog., 2008, 4(11):e1000211, 15 pages.

Baumruker et al., "FTY720, an immunomodulatory sphingolipid mimetic: translation of a novel mechanism into clinical benefit in multiple sclerosis," Expert Opin. Investig. Drugs, 2007, 16(3):283-289.

Berge et al., "Pharmaceutical salts," Journal of Pharmaceutical Sciences, 1977, 66:1-19.

Biopharmatiques, "Merging Pharma and Biotech", http://www.biopharmaceutiques.com/fr/tables/clinical_studies_709.html, 2009.

Bioreversible Carriers in Dmg Design, ed. Edward B. Roche, American Pharmaceutical Association and Pergamon Press 1987 *too voluminous.

Boismenu et al., "Insights from mouse models of colitis," K. Leukoc Biol, 67:267-278, 2000.

Bolick et al., "Sphingosine-1-Phosphate Prevents Tumor Necrosis Factor-alpha-Mediated Monocyte Adhesion to Aortic Endothelium in Mice," Arterioscler. Thromb. Vasc. Biol., 2005, 25:976-981.

Brinkman, "Sphingosine 1-phosphate receptors in health and disease: Mechanistic insights from gene deletion studies and reverse pharmacology," Pharmacol. Ther., 2007, 115:84-105.

Brinkmann et al., "Fingolimod (FTY720): discovery and development of an oral drug to treat multiple sclerosis," Nat Rev Drug Discov, Nov. 2010, 9(11):883-97.

Brinkmann et al., "FTY720 Alters Lymphocyte Homing and Protects Allografts Without Inducing General Immunosuppression," Transplantation Proc., 2001, 33:530-531.

Brinkmann et al., "FTY720: Altered Lymphocyte Traffic Results in Allograft Protection," Transplantation, Sep. 2001, 72(5):764-769.

Brinkmann et al., "The immune modulator FTY720 targets sphingosine 1-phosphate receptors," J Biol Chem 2002; 277:21453-57.

(56) References Cited

OTHER PUBLICATIONS

Brinkmann, "FTY720 (fingolimod) in Multiple Sclerosis: therapeutic effects in the immune and the central nervous system", British Journal of Pharmacology, 158: 1173-1182, 2009.
Brunauer et al., "Adsorption of gases in multimolecular layers," J. Am. Chem. Soc., 1938, 60:309-319.
Bnmsting et al. "Pyoderma (Echthyma) Gangrenosum Clinical and Experimental Observations in Five Cases Occurring in Adults," Arch Dermatol Syph, 1930, 22:655-680.
Budde et al., "First Human Trial of FTY720, a Novel Immunomodulator, in Stable Renal Transplant Patients," J Am Soc. Nephrol., 2002, 13:1073-1083.
Burisch et al., "The burden of inflammatory bowel disease in Europe," J Crohns Colitis., 2013, 7(4):322-37.
Buzard, Daniel J et al., "Recent Progress in the Development of Selective S1P1 Receptor Agonists for the Treatment of Inflammatory and Autoimmune Disorders", Expert Opinion, 1141-1159, 2008.
Buzard et al., "Discovery of APD334: design of a clinical stage functional antagonist of the sphinogosine-1-phosphate-1 receptor," ACS Med. Chem. Lett., 2014, 5, 5(12):1313-1317.
Buzard et al., "Discovery and Characterization of Potent and Selective 4-Oxo-4-(5-(5-phenyl-1,2,4-oxadiazol-3-yl)indolin-1-yl)butanoic acids as S1P1 Agonists", Biorganic Med. Chem. Lett., 2011, 6013-6018.
Centers for Disease Control and Prevention. Inflammatory bowel disease (IBO). http://www.cdc.gov/ibd/. Accessed Jan. 8, 2015, 2 pages.
Chawla et al., Challenges in Polymorphism of Pharmaceuticals, CRIPS, Jan.-Mar. 2004, vol. 5, No. 1, 4 pages.
Chiba et al., "Role of Sphingosine 1-Phosphate Receptor Type 1 in Lumphocyte Egress from Secondary Lymphoid Tissues and Thymus," Cell Mole Immunol,, Feb. 2006, 3(1): 11-19.
Chiba, "FTY720, a new class of immunomodulator, inhibits lymphocyte egress from secondary lymphoid tissues and thymus by agonistic activity at sphingosine 1-phosphate receptors," Pharmacol. Ther., 2005, 108:308-319.
Chun et al., "International Union of Pharmacology. XXXIV. Lysophospholipid receptor nomenclature," Pharmacological Reviews, 2002, 54(2):265-269.
Coelho et al., "The Immunomodulator FTY720 has a direct cytoprotective effect in oligodendrocyte Progenitors," J Pharmacol. Exp, Ther., 2007, 323:626-635.
Cohen, "Neutrophilic dermatoses: a review of current treatment options," Am J Clin Dermatol., 2009, 10(5):301-12.
Collier et al., "Radiosynthesis and In-vivo Evaluation of the Psuedopeptide 8-pioid Antagonist [$^{125}$I] -ITIPP(Ψ)," J. Labelled Compd. Radiopharm., 1999, 42, S264-S266.
Coste et al., "Antinociceptive activity of the SIP-receptor agonist FTY720," J Cell Moll Med., 2008, 12(3):995-1004.
Crohn's and Colitis Foundation of America. The Facts About Inflammatory Bowel Diseases. Nov. 2014, New York, NY 10017. http://www.ccfa.org/assets/pdfs/ibdfactbook.pdf. Accessed Jan. 7, 2015.
D'Ambrosio et al., "Ponesimod, a selective S1P1 receptor modulator: a potential treatment for multiple sclerosis and other immune-mediated diseases," Therapeutic Advances in Chronic Disease, 2016, 7(1):18-33.
Danese et al., "Ulcerative colitis," N Engl J Med, 2011, 365(18):1713-1725.
Daniel et al., "FTY720 Ameliorates Th1-Mediated Colitis in Mice by Directly Affecting the Functional Activity of DC4+CD25+ Regulatoiy T Cell1," J Immunol., 2007, 178:2458-2468.
Deguchi et al., "The SIP receptor modulator FTY720 prevents the development of experimental colitis in mice," Oncol. Rep., 2006, 16:699-703.
Dev et al., "Brain sphingosine-1-phosphate receptors: Implication for FTY720 in the treatment of multiple sclerosis," Pharmacol Ther., 2008, 117:77-93.

Dillmann et al., "S1PR4 Signaling Attenuates ILT 7 Internalization To Limit IFN-α Production by Human Plasmacytoid Dendritic Cells," J Immunol., 2016, 15;196(4):1579-90.
Fingolimod, Wikipedia, the free encyclopedia, retrieved on Jul. 22, 2014, http://en.wikipedia.org/wiki/Fingolimod, 6 pages.
Fischer et al., "Targeting receptor tyrosine kinase signalling in small cell lung cancer (SCLC): What have we learned so far?" Cancer Treatment Revs., 2007, 33:391-406.
Freling et al., "Cumulative incidence of, risk factors for, and outcome of dermatological complications of anti-TNF therapy in inflammatory bowel disease: a 14-year experience," Am J Gastroenterol, 2015, 110:1186-1196.
Fu et al., "Long-term islet graft survival in streptozotocin- and autoimmune-induced diabetes models by immunosuppressive and potential insulinotropic agent FTY720," Transplantation, May 2002, 73(9): 1425-1430.
Fujii et al., "FTY720 suppresses CD4+CD44highCD62L- effector memory T cell-mediated colitis," Am J Physol Gastrointest Liver Physiol., 2006, 291:G267-G274.
Fujino et al., "Amerlioration of Experimental Autoimmune Encephalomyelitis in Lewis Rats by FTY720 Treatment," J Pharmacol. Exp. Ther., 2003, 305(1):70-77.
Fujishiro et al., "Change from Cyclosporine to Combination Therapy of Mycophenolic Acid with the New Sphinogosine-1-phosphate Receptor Agonist, KRP-203, Prevents Host Nephrotoxicity and Transplant Vasculopathy in Rats," J Heart Lung Transplant, 2006, 25:825-833.
Gabriel et al., "High throughput screening technologies for direct cyclic AMP measurement", ASSAY and Drug Development Technologies, 2003, 1(2):291-303.
Gameiro et al., "Pyoderma gangrenosum: challenges and solutions" Clin. Cos. Inv. Dermatol, 2015, 8:285-293.
Gergely et al., "The selective sphingosine 1-phosphate receptor modulator BAF312 redirects lymphocyte distribution and has species-specific effects on heart rate," British J of Pharm, 2012, 167(5):1035-1047.
Golub et al., "Molecular Classification of Cancer: Class Discovery and Class Prediction by Gene Expression Monitoring," Science, 1999, 286:531-537.
Gottlieb, et al., "NMR Chemical Shifts of Common Laboratory Solvents as trace Impurities," J. Org. Chem. 1997, 62, 7512-7515.
Greene, T.W. and Wuts, P.G.M., Protecting Groups in Organic Synthesis, $3^{rd}$ Edition, 1999 [Wiley] * (too voluminous to provide).
Griesser, "The Importance of Solvates" in Polymorphism in the Pharmaceutical Industry, 211-233 (Rolf Hilfiker, ed., 2006).
Groeneveld, "Vascular pharmacology of acute lung injury and acute respiratory distress syndrome," Vascular Pharmacol., 2003, 39:247-256.
Guillory, "Generation of Polymorphs, Hydrates, Solvates, and Amorphous Solids," in:Polymorphism in Pharmaceutical Solids, ed. Harry G.Brittan, vol. 95, Marcel Dekker, Inc. New York, 1999, pp. 202-209.
Hale et al., "Potent SIP receptor agonists replicate the pharmacologic actions of the novel immune modulator FTY720," Bioorganic Med Chem., Lett., 2004, 14:3351-335.
Han, Sangdon et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-1-phosphate (S1P1) Receptor Agonists", Arena Pharmaceuticals, Inc., MEDI098, ACS Poster, Mar. 2011.
Herzinger et al., "Sphingosine-1-Phosphate Signaling and the Skin," Am J Clin Dermatol., 2007, 8(6):329-336.
Higuchi and Stella, Pro-drugs as Novel Delivery Systems vol. 14 of the A.C.S. Symposium Series, 1975, 129 pages.
Hwang et al., "FTY720, a New Immunosuppressant, Promotes Long-Term Graft Survival and Inhibits the Progression of Graft Coronary Artery Disease in a Murine Model of Cardiac Transplantation," Circulation, 1999, 100:1322-1329.
Idzko et al., "Local application of FTY720 to the lung abrogates experimental asthma by altering dendritic cell function," J Cline Invest, Nov. 2006, 116(11):2935-2944.
International Search Report and Written Opinion in Application No. PCT/US2018/000091, dated May 6, 2018, 8 pages.

(56) References Cited

OTHER PUBLICATIONS

International Search Report and Written Opinion in Appln. No. PCT/US2018/000048, dated Aug. 23, 2018.
Ishii et al., "Sphingosine-1-phosphate mobilizes osteoclast precursors and regulates bone homeostasis," Nature, Mar. 2009, 458(7237):524-528.
Jones, Robert M., "Discovery of Potent and Selective Sphingosine-1-Phosphate 1 (S1P1) Receptor Agonists", CHI 6$^{th}$ Annual Drug Discovery Chemistiy, San Diego, CA, Apr. 12, 2011.
Jung et al., "Functional Consequences of SIP Receptor Modulation in Rat Oligodendroglial Lineage Cells," Glia, 2007, 55:1656-1667.
Kaneider et al., "The immune modulator FTY720 targets sphingosine-kinase-dependent migration of human monocytes in response to amyloid beta-protein and its precursor," FASEB J, 2004, 18:309-311.
Kappos et al., "A placebo-controlled trial of oral fingolimod in relapsing multiple sclerosis," N Engl J Med., 2010, 362(5):387-401.
Kappos et al., "Oral Fingolimod (FTY720) for Relapsing Multiple Sclerosis," N Engl J Med., 2006, 355:1124-1140.
Karimian et al., "Sphingosine kinase-1 inhibition protects primary rat hepatocytes against bile salt-induced apoptosis," Biochim Biophys Acta., 2013, 1832(12):1922-9.
Kataoka et al., "FTY720, Sphingosine 1-Phosphate Receptor Modulator, Ameliorates Experimental Autoimmune Encephalomyelitis by Inhibition of T Cell Infiltration," Cell Mol. Immunol., Dec. 2005, 2(6):439-448.
Kandel et al., "FTY720 for Treatment of Ischemia-Reperfusion Injury Following Complete Renal Ischemia; Impact on Long-Term Survival and T-Lymphocyte Tissue Infiltration," Transplantation Proc., 2007, 39:499-502.
Kawasaki, Andrew et al., "Discovery and Characterization of 2-(7-(5-phenyl-1,2,4-oxadiazol-3-yl)-2,3-dihydro-1H-pyrrolo[1,2-a]indol-1-yl)acetic acid Derivatives as Potent & Selective Human S1P1 Receptor Agonists", Arena Pharmaceuticals, Inc., MED1254, ACS, Mar. 2011.
Keul et al., "The Sphinogosine-1-Phosphate Analogue FTY720 Reduces Atherosclerosis in Apolipoprotein E-Deficient Mice," Arterioscler Thromb Vasc Biol., 2007, 27:607-613.
Kim et al., "Sphingosine-1-phosphate inhibits human keratinocyte proliferation via Akt/protein kinase B inactivation," Cell Signal, 2004, 16:89-95.
Kimura et al., "Essential Roles of Sphingosine 1-Phosphate/S1P1 Receptor Axis in the Migration of Neural Stem Cells Toward a Site of Spinal Cord Injury," Stem Cells, 2007, 25:115-124.
Kiyabayashi et al., "FTY720 Prevents Development of Experimental Autoimmune Myocarditis Through Reduction of Circulating Lymphocytes," J Cardiovasc. Pharmacol. 2000, 35410-416.
Kohono et al., "A Novel Immunomodulator, FTY720, Prevents Development of Experimental Autoimmune Myasthenia Gravis in C57BL/6 Mice," Biol Pharma Bull., 2005, 28(4):736-739.
Kohono et al., "A Novel Immunomodulator, FTY720, Prevents Spontaneous Dermatitis in NC/Nga Mice," Biol. Pharm. Bull., 2004, 27(9):1392-1396.
Koreck et al., "The Role of Innate Immunity in the Pathogensis of Acne," Dermatol., 2003, 206:96-105.
Kurose et al., "Effects of FTY720, a novel immunosuppressant, on experimental autoimmune uveoretinitis in rats," Exp. Eye Res., 2000, 70:7-15.
Lala et al., "Role of nitric oxide in tumor progression: Lessons from experimental tumors," Cancer Metastasis Rev., 1998, 17:91-106.
Lamontagne et al., "Antagonism of Sphingosine-1-Phosphate Receptors by FTY720 Inhibits Angiogenesis and Tumor Vascularization," Cancer Res., 2006, 66:221-231.
Le Bas, et al., "Radioiodinated Analogs of EP 00652218 for the Exploration of the Tachykinin NK1 Receptor by Spect," J. Labelled Compl. Radiopharm. 2001, 44, S280-S282.
Lee et al., "FTY720: A Promising Agent for Treatment of Metastatic Hepatocellular Carcinoma," Clin. Cancer Res., 2005, 11:8458-8466.

Lima et al., "FTY720 Treatment Prolongs Skin Graft Survival in a Completely Incompatible Strain Combination," Transplant Proc., 2004, 36:1015-1017.
Liu et al., "Long-Term Effect of FTY720 on Lymphocyte Count and Islet Allograft Survival in Mice," Microsurgery, 2007, 27:300-304.
Lleo et al., "Etiopathogenesis of primary viliary cirrhosis," *World J Gastroenterol*, Jun. 2008, 14(21):3328-3337.
Loftus, "Clinical epidemiology of inflammatory bowel disease: Incidence, prevalence, and environmental influences," Gastroenterology, 2004; 126(6):1504-17.
Madhusudan et al., "Tyrosine kinase inhibitors in cancer therapy," Clinical Biochem., 2004, 37:618-635.
Maki et al., "Prevention and Cure of Autoimmune Diabetes in Nonobese Diabetic Mice by Continuous Administration of FTY720," Transplantation, 2005, 79:1051-1055.
Maki et al., "Prevention of autoimmune diabetes by FTY720 in Nonobese diabetic mice," Transplantation, Dec. 2002, 74(12): 1684-1686.
Martini et al., "Current perspectives on FTY720," Expert Opin. Investig. Drugs, 2007, 16:505-518.
Martini et al., "SIP modulator FTY720 limits matrix expansion in acute anti-thy 1 mesangioproliferative glomerulonephritis," Am J Physiol Renal Physiol., 2007, 292:F1761-F1770.
Marzano et al., "Cutaneous manifestations in patients with inflammatory bowel diseases: pathophysiology, clinical features, and therapy," Inflamm. Bowel Dis., 2014, 20:213-227.
Marzano et al., "Role of inflammatory cells, cytokines and matrix metalloproteinases in neutrophil-mediated skin diseases," Experimental Immunology, 2010, 162:1-11.
Matloubian et al., "Lymphocyte egress from thymus and peripheral lymphoid organs in dependent on S1P receptor 1," Nature, Jan. 2004, 427:355-360.
Matsuura et al., "Effect of FTY720, a novel immunosuppressant, on adjuvant- and collagen-induced arthritis in rats," Int. J Immunopharmacol. 2000, 22:323-331.
Matsuura et al., "Effect of FTY720, a novel immunosuppressant, on adjuvant-induced arthritis in rats," Inflamm. Res. 2000, 49:404-410.
Medscape. 2017 Inflammatory Bowel Disease: Practice Essentials, 2017 http://emedicine.medscape.com/article/179037-ovcrview#aw2aab6b2b4. Accessed Jan. 8, ~015.
Miron et al., "FTY720 Modulates Human Oligodendrocyte Progenitor Process Extension and Survival," Ann Neurol, 2008, 63:61-71.
Miyamoto et al., "Therapeutic Effects of FTY720, a New Immunosuppressive Agent, in a Murine Model of Acute Viral Myocarditis," J Am Coll Cardiol., 2001, 37(6): 1713-1718.
Mizushima et al., "Therapeutic Effects of a New Lymphocyte Homing Reagent FTY720 in Interleukin-10 Gene-deficient Mice with Colitis," Inflamm Bowel Dis., May 2004, 10(3):182-192.
Morissette, et al., "High-Throughput Crystallization: Polymorphs, Salts, Co-Crystals and Solvates", *Adv. Drug Delivery Rev.*, 56:275-300 (2004).
Nakashima et al., "Impaired Initiation of Contact Hypersensitivity by FTY720," J Invest Dermatol., 2008, 128:2833-2841.
Nestle et al., "Plasmacytoid predendritic cells initiate psoriasis through interferon-alpha production," J Exp Med., 2005, 202(1):135-43.
Neurath et al., "Antibodies to Interleukin 12 Abrogate Established Experimental Colitis in Mice," J. Exp. Med, 182:1281-1290, 1995.
Newman et al., "Solid-state analysis of active pharmaceutical ingredient in drug products," DDT, Oct. 2003, 8(19):898-905.
Nofer et al., "FTY720, a Synthetic Sphingosine 1 Phosphate Analogue, Inhibits Development of Atherosclerosis in Low-Density Lipoprotein Receptor Deficient Mice," Circulation, 2007, 115:501-508.
Ogawa et al., "A novel sphingosine-1-phosphate receptor agonist KRP-203 attenuates rate autoimmune myocarditis," Biochem. Biophys. Res. Commun., 2007, 361:621-628.
Okayasu et al., "A Novel Method in the Induction of Reliable Experimental Acute and Chronic Ulcerative Colitis in Mice," Gastroenterology, 98:694-702, 1990.

(56) References Cited

OTHER PUBLICATIONS

Okazaki et al., "Effects of FTY720 in MRL-Ipr/Ipr mice: therapeutic potential in systemic lupus eiythematosus," J Rheumatol., 2002, 29:707-716.
Oo et al., "Immunosuppressive and Anti-angiogenic Sphingosine 1-Phosphate Receptor-1 Agonists Induce Ubiquitinylation and Proteasomal Degradation of the Receptor," J Biol Chem., 2007, 282(12):9082-9089.
Optical Microscopy, Physical Tests, 2012, 331-334.
Pan et al., "A Monoselective Sphingosine- 1-Phosphate Receptor-1 Agonist Prevents Allograft Rejection in a Stringent Rat Heart Transplantation Model," Chem. Biol., 2006, 13:1227-1234.
Paul et al., "Evidence-based recommendations on topical treatment and phototherapy of psoriasis: systematic review and expert opinion of a panel of dermatologists," J Eur Acad Dermatol Venereol, 2012, 26 (suppl 3): 1-10.
Pheilschifter et al., "Treatment with immunomodulator FTY720 does not promote spontaneous bacterial infections after experimental stroke mice," Experimental Translational Stroke Med., 2011, 3, 6 pages.
Premenko-Lanier et al., "Transient FTY720 treatment promotes immune-mediated clearance of a chronic viral infection," Nature, Aug. 2008, 454:894-899.
Quaglino et al., "Phenotypical characterization of circulating cell subsets in pyoderma gangrenosum patients: the experience of the Italian immuno-pathology group," J Eur Acad Dermatol Venereal, 2016, 30(4):655-8.
Rasenack et al., "Crystal habit and tableting behavior," International Journal of Pharmaceutics, Sep. 2002, 244(1-2): 45-57.
Rausch et al., "Predictiability of FTY720 Efficacy in Experimental Autoimmune Encephalomyelitis by In Vivo Macrophage Tracking: Clinical Implications for Ultrasmall Superparamagnetic Iron Oxide-Enhanced Magnetic Resonance Imaging," 2004, J Magn. Reson. Imaging, 2004, 20:16-24.
Raveney et al., "Fingolimod (FTY720) as an Acute Rescue Therapy for Intraocular Inflammatory Disease," Arch Ophthalmol, 2008, 126(10):1390-1395.
Reines et al., "Topical application of sphingosine-l-phosphate and FTY720 attenuate allergic contact dermatitis reaction through inhibition of dendritic cell migration," J Clin Invest Dermatol, 2009, 129(8): 1954-62.
Remington, The Science and Practice of Pharmacy, 20th Edition, 2000, Lippincott Williams & Wilkins, (Editors: Gennaro et al.) * (too voluminous).
Reshetnyak, "Primary biliary cirrhosis: Clinical and laboratory criteria for its diagnosis," World J of Gastroenterology, 2015, 21(25):7683-7708.
Rheumatoid Arthritis Health Center—Most Common Types of Arthritis, WebMD, http://www.webmd.com/rheumatoid-arthritis/guide/most-common-arthritis-types, 2012, 2 pages.
RN 380350-42-5, STN/CAPLUS (Year: 2002).
Ronald Hoffman, M.D., "Crohns disease and ulcerative colitis," Sep. 1995, http://www.drhoffman.com/page.cfm/171, 5 pages.
Rosen et al., "Egress: a receptor-regulated step in lymphocyte trafficking," Immunol. Rev. 2003, 195:160-177.
Sakagawa et al., "Rejection following donor or recipient preoperative treatment with FTY720 in rat small bowel transplantation," Transpl. Immunol., 2004, 13:161-168.
Sanchez et al., "Phosphorylation and Action of the Immunomodulator FTY720 Inhibits Vascular Endothelial Cell Growth Factor-induced Vascular Permeability," J Biol Chem., 2003, 278(47):47281-47290.
Sanna et al., "Enhancement of cappillary leakage and restoration of lymphocyte egress by a chiral S1P1 antagonist in vivo," Nature Chem Biol., Aug. 2006, 2(8):434-441.
Sanna et al., "Sphingosine 1-Phosphate (SIP) Receptor Subtypes S1P1 and S1P3, Respectively, Regulate Lymphocyte Recirculation and Heart Rate," J. Biol Chem., 2004, 279(14):13839-13848.

Sauer et al., "Involvement of Smad Signlaing in Sphingosine 1-Phosphate-mediated Biological Responses of Keratinocytes," J Biol. Chem., 2004, 279:38471-38479.
Sawicka et al., "Inhibition of Th1- and Th2-Mediated Airway Inflammation by the Sphingosine 1-Phosphate Receptor Agonist FTY720," J Immunol., 2003, 171:6206-6214.
Schafiee et al., "An efficent enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," Tetrahedron: Asymmetry, Sep. 2005, 16:3094-3098.
Schaper et al.,"Sphingosine-1-phosphate differently regulates the cytokine production of IL-12, IL-23 and IL-27 in activated murine bone marrow derived dendritic cells," Mol Immunol., 2014, 59(1):10-8.
Schmid et al., "The Immunosuppressant FTY720 inhibits tumor Angiogenesis via the Sphingosine 1-Phosphate Receptor 1," J Cell Biochem., 2007, 101:259-270.
Schuppel et al., "Sphingosine 1-phosphate restrains insulin-mediated keratinocyte proliferation via inhibition of Akt through the S1P2 receptor subtype," J Invest Dermatol, 2008, 128:1747-56.
Schwab and Cyster, "Finding a way out: lymphocyte egress from lymphoid organs," Nature Immunol., Dec. 2007, 8(12):1295-1301.
Shimizu et al., "KRP-203, a Novel Synthetic Immunosuppressant, Prolongs Graft Survival and Attenuates Chronic Rejection in Rat Skin and Heart Allografts," Circulation, 2005, 111:222-229.
Shtukenberg et al., "Spherulites," Chemical Reviews, 2012, 112: 1805-1838.
Stahly, "Diversity in Single- and Multiple-Component Crystals. The Search for and Prevalence of Polymorphs and Cocrystals," Crystal Growth & Design (2007), 7(6), 1007-1026.
Storey, et al., "Automation of Solid Form Screening Procedures in the Pharmaceutical Industry-How to Avoid the Bottlenecks", Crystallography Reviews, 10(1):45-46 (2004).
Sturino et al: "Discovery of a potent and selective prostaglandin D2 receptor antagonist, [(3R)-4-(4-chloro-benzyl)-7-Fluoro-5-(methylsulfonyl)-1,2,3,4-tetrahydrocyclopenta[b]indol-3-yl]-acetic acid (MK-0524)", Journal of Medicinal Chemistiy, Feb. 22, 2007, pp. 794-806.
Su et al., "Histopathologic and immunopathologic study of pyoderma gangrenosum," J Cut. Path, 1986, 13(5):323-330.
Suzuki et al., "Efficacy of Mycophenolic Acid Combined with KRP-203, a Novel Immunomodulator, in a Rat Heart Transplantation Model," J Heart Lung Transplant, 2006, 25:302-309.
Suzuki et al., "Immunosuppressive effect of a new drug, FTY720, on lymphocyte responses in vitro and cardiac allograft survival in rats," Transplant Immunol., 1996, 4:252-255.
Taverela, "Review article: skin complications associated with inflammatory bowel disease," Aliment Pharmacol Ther, 2004, Suppl 4:50-53.
Taylor et al., "Insights into the mechanism of FTY720 and compatibility with regulatory T cells for the inhibition of graft-versus-host disease (GVHD)," Blood, 2007, 110:3480-3488.
Truong et al., "Human Islet Function is not Impaired by the Sphingosine-1-Phosphate Receptor Modulator FTY720," Am J Transplantation, 2007, 7:2031-2038.
Truppo et al., "Optimization and Scale-Up of a Lipase-Catalyzed Enzymatic Resolution of an Indole Ester Intermediate for a Prostaglandin D2 (DP) Receptor Antagonist Targeting Allergic Rhinitis," Organic Process Research and Development, Feb. 2006, 10(3):592-598.
U.S. Department of Health & Human Services National, 2016 Institutes of Health, https://rarediseases.info.nih.gov/diseases/7510/pyoderma-gangrenosum.
Vachal et al., "Highly selective and potent agonists of sphinogosin-1-phosphate 1 (S1P1) receptor," Bioorganic Med Chem Lett., Jul. 2006, 16(14):3684-3687.
Vaclavkova et al., "Oral ponesimod in patients with chronic plaque psoriasis: a randomised, double-blind, placebo-controlled phase 2 trial," Lancet, 2014, 384(9959):2036-45.
Valdimarsson et al., "Psoriasis—as an autoimmune disease caused by molecular mimicry," Trends in Immunology, Oct. 2009, 30(10):494-501.

(56) References Cited

OTHER PUBLICATIONS

Variankaval and Cote, "From Form to Function: Cyrstallization of Active Pharmaceutical Ingredients," AIChe Journal, Jul. 2008, 54(7): 1682-1688.
Vavricka et al., "Extraintestinal manifestations of inflammatory bowel disease," Inflammatory Bowel Diseases, 2015, 21(8):1982-1992.
Villullas et al., "Characterisation of a Sphingosine 1-Phosphate-Activated Ca2+ Signalling Pathway in Human Neuroblastoma Cells," J. Neurosci. Res, 73:215-226, 2003.
Vippagunta, et al., "Crystalline Solids," Adv. Drug Delivery Rev., 48:3-26 (2001).
Von den Driesch, "Pyoderma gangrenosum: a report of 44 cases with follow-up," Br. J. Dermatol, 1997, 137(6):1000-5.
Webb et al., "Sphingosine 1-phosphate receptors agonists attenuate relapsing—remitting experimental autoimmune encephalitis in SJL mice," J Neuroimmunol., 2004, 153:108-121.
Webster, "The Pathophysiology of Acne," Cutis, 2005, 76(suppl. 2):4-7.
Weenig et al., "Skin ulcers misdiagnosed as pyoderma gangrenosum," N Engl J Med, 2002, 347:1412-1418.
Whetzel et al., "Sphingosine-1 Phosphate Prevents Monocyte/Endothelial Interactions in Type 1 Diabetic NOD Mice Through Activation of the S1P1 Receptor," Circ. Res., 2006, 99:731-739.
Wollina, "Pyoderma gangrenosum-a review," Orphanet Journal of Rare Diseases; 2007, 2:19.
World IBP Day, http://www.worldibdday.org/index.html. Accessed Jan. 7, 2015.
Xu et al., "Safety, pharmacokinetics, pharmacodynamics, and bioavailability of GSK2018682, a sphingosine-1-phosphate receptor modulator, in healthy volunteers," Am College of Clinical Pharm, 2014, 3(3): 170-178.
Yamamoto, "Crohn's disease and mucocutaneous conditions," Journal of Clinical and Experimental Dermatology Research, 2014 4(2):1-6.
Yan et al., "Discovery of 3-arylpropionic acids as potent agonists of sphingosine-1-phosphate receptor-1 (S1P1) with high selectivity against all other known SIP receptor subtypes," Bioorg. Med. Chem. Lett., 2006, 16:3679-3683.
Yanagawa et al., "FTY720, a Novel Immunosuppressant, Induces Sequestration of Circulating Mature Lymphocytes by Acceleration of Lymphocyte Homing in Rats. II. FTY720 Prolongs Skin Allograft Survival by Decreasing T Cell Infiltration into Grafts But not cytokine production in vivo," J Immunol., 1998, 160:5493-5499.
Yang et al., "Sphingosine kinase/sphingosine 1-phosphate (S1P)/S1P receptor axis is involved in liver fibrosis-associated angiogenesis," J Hepatol., 2013, 59(1):114-23.
Yang et al., "The immune modulator FYT720 prevents autoimmune diabetes in nonobese diabetic mice," Clin. Immunol., 2003, 107:30-35.
Yates et al., "Further evidence for an association between psoriasis, Crohn's disease and ulcerative colitis," Br J Dermatol, 1982, 106(3):323-330.
Zhang et al., "FTY720 attenuates accumulation of EMAP-11+ and MHC-II+ monocytes in early lesions of rat traumatic brain injmy," J Cell Mol Med., 2007, 11(2):307-314.
Zhang et al., "FTY720: A Most Promising Immunosuppressant Modulating Immune Cell Functions," Mini Rev. Med Chem., 2007, 7:845-850.
Zhu et al., "Synthesis and Mode of Action of 125I-and 3H- Labeled Thieno[2,3-c]pyridine Antagonists of Cell Adhesion Molecule Expression," J. Org. Chem., 2002, 67, 943-948.
Fenofibrate Prescribing Information Revised Nov. 2018, 19 pages.
Abbott et al, "Blockade of the neuropeptide Y Y2 receptor with the specific antagonist BIIE0246 attenuates the effect of endogenous and exogenous peptide YY (3-36) on food intake," Brain Res, 2005, 1043:139-144.
Abdalla et al., "Synthesis and reaction of 3-cyano 2-(1H)-pyridones," Pakistan Journal of Scientific and Industrial Research, Jun. 1977, 30(3):139-149.

Abe et al., "First Synthesis and Determination of the Absolute Configuration of Sulphostin, a Novel Inhibitor of Dipeptidyl Peptidase IV." J. Nat. Prod., 2004, 67:999-1004.
Abramovitch et al., "Solution and flash vacuum pyrolysis of some 2.6-disubstituted β-phenethyslulfonyl azides and of β-styrenesulfonyl azide," J. Org Chem, 1985, 50-2066-2073.
Abstract # 107, p. 56, Toward Understanding Islet Biology, Jan. 21, 2003-Jan. 26, 2003, Keystone, Colorado.
Abstract #112, p. 42, Diabetes Mellitus: Molecular Mechanisms, Genetics and New Therapies, Jan. 27, 2005-Feb. 2, 2005, Keystone, Colorado.
Abstract #117 & Poster, Diabetes: Molecular Genetics, Signaling Pathways and Integrated Physiology. Jan. 14, 2007-Jan. 19, 2007, Keystone, Colorado, 3 pages.
Abstract #228, p. 54, Diabetes Mellitus: Molecular Mechanisms, Genetics and New Therapies, Jan. 27, 2005-Feb. 2, 2005, Keystone, Colorado.
Abstract #230 & Poster, Diabetes: Molecular Genetics, Signaling Pathways and Integrated Physiology, Jan. 14, 2007-Jan. 19, 2007, Keystone, Colorado, 6 pages.
Accession No. 2003:2246299 Chemicals. IH-Pvrazolo [3,4-d] pyrimidin-4-amine, N-cyclohexyl-N-methyl-1-(3--methyphenyl)-(2003),1 page.
Accession No. 2003:2246300 Chemicals, 1H-Pyrazolo [3,4-d] pyrimidin-4-amine, N-cyclohexyl-1-(2,4--dimethlphenyl)-N-methyl-(2003), 1 page.
Accession No. 2003:2415108 CHEMCATS, Interbioscreen Compound Library, Chemical Name: 1H-Pyrazolo[3,4-d]pyrimidine-4-amine, N-cyclohexyl-N-methyl-1-(3-methylphenyl)-, XP-002311326, 2003, CAS Registry No. 393844-90-1, 1 page.
Accession No. 2003:2415906 CHEMCATS, Interbioscreen Compound Library, Chemical Name: 1H-Pyrazolo[3,4-d]pyrimidine-4-amine, N-cyclohexyl-1-1-(4-methylphenyl)-, XP-002311325, 2003, CAS Registry No. 393844-89-8, 1 page.
Accession No. 2003:2416398 CHEMCATS, Interbioscreen Compound Library, Chemical Name: 1H-Pyrazolo[3,4-d]pyrimidine-4-amine, N-cyclohexyl-1-1-(2,4-dimethylphenyl)-N-methyl-, XP-002311324, 2003, CAS Registry No. 393844-91-2, 1 page.
Accession No. 2003:2417080 CHEMCATS, Interbioscreen Compound Library, Chemical Name: 1H-Pyrazolo[3,4-d]pyrimidine-4-amine, N-cyclohexyl-N-methyl-1-phenyl)-, XP-002311323, 2003, CAS Registry No. 393844-87-6, 1 page.
Adams et al., "Etrasimod (APD334), an Oral, Next-Generation Sphingosine-1-Phosphate Receptor Modulator Inhibits the Development of Colitis in Lymphoid-Null Mice Injected with Colitogenic CD4+ T Cells," The FASEB Journal, Apr. 2017, 31(S1): 993.11-993-11.
Adrian et al., "Human Distribution and Release of a Putative New Gut Hormone, Peptide YY," Gastroenterol., 1985, 89(5):1070-1077.
Ahren et al., "Inhibition of Dipeptidyl Peptidase-4 Augments Insulin Secretion in Response to Exogenously Administered Glucagon-Like Peptide-1, Glucose-Dependent Insulinotropic Polypeptide, Pituitary Adenylate Cyclase-Activating Polypeptide, and Gastrin-Releasing Peptide in Mice," Endocrinology, 2005, 146(4):2055-2059.
Ahren et al., "Inhibition of Dipeptidyl Peptidase-4 Reduces Glycemia, Sustains Insulin Levels, and Reduces Glucagon Levels in Type 2 Diabetes," J. Clin. Endocrinol. Metab., 2004, 89:2078-2084.
Ahren et al., "Inhibition of Dipeptidyl Peptidease IV Improves Metabolic Control Over a 4-week Study Period in Type 2 Diabetes," Diabetes Care, 2002, 25:869-875.
Aidsinfo.nih.gov [online] "Dyslipidemia," Nov. 1, 2012, retrieved Jan. 22, 2014, retrieved from URL <http://aidsinfo.nih.gov/guidelines/html/2/pediatric-arv-guidelines/91/dyslipidemia>, 4 pages.
Ambooken et al., "Malignant pyoderma gangrenosum eroding the parotid gland successfully treated with dexametlrasone pulse therapy," Int. J. Dermatol., 2014, 53:1536-1538.
American Diabetes Association, "Dyslipidemia Prevalent in Type 2 Diabetes," Jul. 2010, http://docnews.diabetesjournals.org/content/3/3/19.1.full, retrieved on Sep. 24, 2014, 2 pages.
American Diabetes Association, "Hyperglycemia (High blood sugar)," accessed Jul. 1, 2011, http://www.diabetes.org/living-with-diabetes/treatment-and-care/blood-glucose-control/hyperglycemia.html. 1 page.

(56) References Cited

OTHER PUBLICATIONS

American Heart Association [online], "Metabolic Syndrome," available on or before Nov. 2001, retrieved on Sep. 24, 2014, retrieved from URL <http://www.americanheart.org/pre-senter.jhtml?identifier=4756>, 3 pages.
Appukkuttan et al., "Translation-Metal-Free Sonogasbira-Type Coupling Reactions in Water," European Journal of Organic Chemisty, 2003, 24-4713-4716.
Arehar et al. "Acceleration of Cardiovascular Disease by a Dysfunctional Prostacyclin Receptor Mutation—Potential Implications for Cyclooxygenase-2 Inhibition," Circ Res, 2008, 102:986-993.
Arena Pharmaceuticals [online], "Arena Pharmaceuticals Reports Positive Phase 2 Results from the OASIS Trial for Etrasimod in Patients with Ulcerative Colitis." Mar. 19, 2018, retrieved Mar. 21, 2022, retrieved from URL <https://invest.arenapharm.com/news-releases/news-release-details/arena-pharmaceuticals-reports-positive-phase-2-results-oasis>, 5 pages.
Arvanitis et al., "CRF Ligands via Suzuki and negishi couplings of 3-pyridvl boronic acids or halides with 2-benzyloxy-4-chloro-3-nitropyridione," Biooorganic & Medicinal Chemistry Letters, 2003, 13(2)-289-291.
Arvanitis et al., "Imidazo[4,5-b]ppyridines as corticotropin releasing factor receptor ligands," Bioorganic & Medicinal Chemistry Letters, 2003, 12(1):125-128.
Arvanitis et al., "Non-peptide corticotropin-releasing hormone antagonists; syntheses and stncture-activity relationships of 2-anilinopytimidines and triaznes." J Med Chem., 1999, 42(5):805-18.
Arvela et al., "Rapid cyanation of aryl iodides in water using microwave promotion," Org. Bio. Chem., 2003, 1:1119-1121.
Arvela et al., "Rapid, Easy Cyanation of Aryl Bromides and Chlorides Using Nickel Salts in Conjunction with Microwave Promotion," J. Org. Chem., 2003, 68:9122-9125.
Atik et al., "Burden of Osteoporosis," Clin Orthop Relat Res, 2006, 443:19-24.
Atwal et al., "Synthesis and Biological Activity of 5-aryl-4-(5-methyl-1H-imidazol-4-yl)piperidin-1-yl)pyrimidine Analogs as Potent, Highly Selective, and Orally Bioavailable NHE-1 Inhibitors," Bioorganic & Medicinal Chemistry Letters, 2006, 16(18):4796-4799.
Augustyns, et al., "Inhibitors of proline-specific dipeptidyl peptidases: DPP IV inhibitors as a novel approach for the treatment of type 2 diabetes," Expert Opin. Ther. Patents, 2005, 15:1387-1407.
Bailey et al., "Interactions Between Grapefruit Juice and Cardiovascular Drugs," American Journal of Cardiovascular Drug, 2004, 4(5) :281-297.
Baindur et al., "Solution-Phase Synthesis of a Library of 3, 5,7-Trisubstituted 3H-[1,2,3]triazolo[4,5-Id]pyrimidines," J. Comb. Chem., 2003, 5:653-659.
Bakkestuen et al., "Regioselective N-9 arylation of purines employing arylboronic acids in presence of Cu(II)," Tetrahedron Letters, 2003, 44:3359-3362.
Balasubramaniam et al., "Neuropeptide Y (NPY) Y2 receptor-selective agonist inhibits food intake and promotes fat metabolism in mice: Combined anorectic effects of Y2 and Y4 receptor-selective agonists," Peptides, 2007, 28:235-240.
Balasubramaniam et al, "Structure-Activity Studies Including a Ψ(CH-NH) Scan of Peptide YY (PYY) Active Site, PYY(22-36), for Interaction with Rat Intestinal PYY Receptors: Development of Analogues with Potent in Vivo Activity in the Intestine," J. Med. Chem., 2000, 43:3420-3427.
Baraldi et al., "An efficient one-pot synthesis of 6-alkoxy-8,9-dialkylpurines via reaction of 5-amino-4-chloro-6-alkylaminopyrimidines with N,N-dimethylalkaneamides and alkoxide ions," Tetrahedron, 2002, 58:7607-7611.
Barta et al., "Synthesis and activity of selective MMP inhibitors with an aryl backbone," Bioorg & Med Chem Ltrs, 2000, 10(24): 2815-2817.
Baskin et al., "A mild, convenient synthesis of sulfinic acid salts and sulfonamides from alkyl and aryl halides," Tetrahedron Letters, 2002, 43:8479-8483.

Baskin et al., "An Efficient Copper Catalyst for the Formation of Sulfones from Sulfinic Acid Salts and And Iodides," Org. Lett., 2002, 4(25):4423-4425.
Batterham et al., "Gut hormone PYY3-36 physiologically inhibits food intake," Nature, 2002, 418:650-654.
Bayes et al., "Apolipoprotein Ealleles, Dyslipemia, and Kidney Transplantation", Transplantation Proceedings, 2002, 34(1):373.
Becalski et al., "Synthesis of carbolines by the Graebe-Ullmann method," Acta Pol Pharm., 1977, 41:601-606.
Bedford et al., "Nonquaternary Cholinesterase Reactivators. 3.3(5)-Substituted 1,2,4-Oxadiazol-5(3)-Aldoximes and 1,2,4-Oxadiazole-5(3)-Thiocarbohydroximates as Reactivators of Organophsphonate-Inhibited Eel and Hunan Acetylcholinesterase In Vitro," J Med Chem, 1986, 29(11):2174-2183.
Behre, "Adiponectin obesity and atherosclerosis," Scand J Clin Lab Invest, 2007, 67:449-458.
Beller et al., "Based-catalyzed amination of olefins; an example of an environmentally friendly synthesis of amines," Chemosphere, 2001, 43(1):21-26.
Betti, et al., "Novel 3-Aralkyl-7 (amino-substituted)-1,2,3-triazole[4,5-d]primidines with High Affinity toward A1 Adenosine Receptors," J. Med. Chem, 1998, 41:668-673.
Bhatt and Thakkar, "Preparation and study of a nickel(II) ion selective electrode," Indian J. Chem, May 1994, 33A:436-437.
Biagi et al., "Synthesis of 4,6-Disubstituted- and 4,5,6-trisubstituted 2-phenyl-pyrimidines and their affinity towards A1 adenosine receptors," Farnaco, 1997, 52(1):61-65.
Bilchik et al, "Peptide YY is a Physiological Regulator of Water and Electrolyte Absorption in the Canine Small Bowel in Vivo," Gastroenterol., 1993, 105:1441-1448.
Boey et al., "Peptide YY ablation in mice leads to the development of hyperinsulinaemia and obesity," Diabetologia, 2006, 49:1360-1370.
Boey et al, "PYY transgenic mice are protected against diet-induced and genetic obesity," Neuropeptides, 2008, 42:19-30.
Bol'but, et al., "A new synthetic approach to fused pyrimidin-4-ones", Institute of Organic Chemistry, National Academy of Sciences of Ukraine, 2003, accessed Mar. 30, 2008, http://conf.iflab.kiev.ua/eng/reports/show/?id=348, 2 pages (Abstract).
Boldt et al. "Simple Synthesis of 2,4-diaminopyridines," Angewandie Chemie International Edition, 1970, 5 pages.
Bollag et al., "Glucose-dependent insulinotropic peptide is an integrative hormone with osteotropic effects," Mol Cell Endocrinol, 2001, 177:35-41.
Bollag et al., "Osteoblast-Derived Cells Express Functional Glucose-Dependent Insulinotropic Peptide Receptors," Endocrinology, 2000, 141:1228-1235.
Bomika et al., "Some Nucleophilic Substitution Reactions of 2-Chloro-3-Cyanopyridines," Khimiya Geterotsiklicheskikh Soedinenii, Aug. 1976, 8:1085-1088 (Translated pp. 896-899).
Boschelli et al., "1,3,4-Oxadiazole, 134-thiadiazole, and 1,3,4-triazole analogs of the fenamates: in vitro inhibition of cyclooxygenase and 5-Lipoxygenase activities," J Med Chem, 1953, 36:1802-1810.
Boswell et al., "Synthesis of Some N-carboxylic acid derivatives of phenoxypyrrolidines, 4-phenoxypiperidines, and 3-phenoxynortropanes with muscle relaxant and anticonvulsant activities," J Med Chem, 1974, 17(9):100-1008.
Bradley, "TNF-mediated inflammatory disease," J Pathol, 2008, 214:149-160.
Brancati et al., "Body Weight Patterns from 20 to 49 Years of Age and Subsequent Risk for Diabetes Mellitus," Arch. Intern. Med., 1999, 159:957-963.
Breuer, "Hypertriglyceridemia: A Review of Clinical Relevance and Treatment Options: Focus on Cerivastatin," Current Medical Research and Opinion, 2001, 17(1):60-73.
Brewer, "Benefit-Risk Assessment of Rosuvastatin 10 to 40 Milligrams," American Journal of Cardiology, 2003, 92(4B):23K-29K.
Bromidge et al., "Design of [R-(Z)-]-(+)-α-(methoxylmino)-lazabicyclo[2.2.2]octane-3-acetonitri le (SB 202026), a functionally selective azabicyclic muscarinic M1 against incorporating the N-methoxy imidoyl nitrile group as a novel esterbioisostere," J Med Chem, 1997, 40(26):4265-4280.

(56) References Cited

OTHER PUBLICATIONS

Brassard et al., "Pharmacokinetics and pharacodynamics of ponesimod, a selective S1P1 receptor modulator, in the first-in-human study," British Journal of Clinical Pharmacology, Dec. 2013, 76(6):888-896.

Buehler et al., "Physiologically active compounds. VI. Cyclic amino thiolesters of substituted chloracetic, benzilic and glycolic acids," J Med Chem, 1965, 8:643-647.

Bulger et al., "An investigation into the alkylation of 1,2,4-triazole," Tetrahedron Letters, 2000, 41:1297-1301.

Buzard, Daniel J. et al., "Discovery and Characterization of Potent and Selective 4-Oxo-4-(5-(5-phenyl-1,2,4-oxadiazol-3-yl)indolin-1-yl)butanoic acids as S1P1 Receptor Agonists", Arena Pliarmaceuticals, Inc., MED1099, ACS, Mar. 2011, 1 page.

Caldwell et al., "Fluoropyrrolidine amides as dipeptidyl peptidase IV inhibitors," Bioorg. Med.Chem. Lett., 2004, 14:1265-1268.

Capuzzi et al., "Beneficial effects of rosuvastatin alone and in combination with extended-release niacin in patients with a combined hyperlipidemia and low high-density lipoprotein cholesterol levels," American Journal of Cardiology, 2003, 91(11):1304-1310.

Capuzzi et al., "Rosuvastatin Alone or With Extended-Release Niacin: A New Therapeutic Option for Patients With Combined Hyperlipidemia," Preventive Cardiology, Fall 2004, 7(4):176-181.

Carswell et al., "Rosuvastatin," Drugs, 2002, 62(14):2075-2085.

Chan et al., "Isoquinoline-6-Carboxamides as Potent and Selective Anti-Human Cytomegalovirus (HCMV)Inhibitors," Bioorganic & Medicinal Chemistry Letters, 1999, 9:2583-2586.

Chapman et al., "Non-High-Density Lipoprotein Cholesterol as a Risk Factor: Addressing Risk Associated with Apolipoprotein B-Containing Lipoproteins," European Heart Journal Supplements, 2004, 6(Suppl. A):A43-A48.

Chapoulaud et al., "Synthesis of 4, 8-Diarylcinnolines and Quinazolines with Potential Applications in Nonlinear Optics. Diazines. Part 28," Tetrahedron (2000) 56:5499-5507.

Chaudhri et al, "Gastrointestinal Satiety Signals," Annu Rev Physiol, 2008, 70:239-255.

Chen et al., "Design and Synthesis of a Series of Non-Peptide High-Affinity Human Corticotropin-Releasing Factor 1 Receptor Antagonists," J Med. Chem., 1996, 39:4358-4360.

Chen et al., "Free Radical Method for the Synthesis of Spiro-Piperidinyl Heterocycles," Tetrahedron Letters, 1996, 37(3):5233-5234.

Chen et al., "Inhibitory Effect of Candesartan and Rosuvastatin on CD40 and MMPs Expression in Apo-E Knockout Mice: Novel Insights into the Role of RAS and Dyslipidemia in Atherogenesis," Journal of Cardiovascular Pharmacology, 2004, 44(4):446-452.

Chen et al., "Optimization of 3-phyenylprazolo[1,5-alpha]pyrimidines as potent corticotrophin-releasing factor-I antagonists with adequate lipophilicity and water solubility." Bioorganic & Medicinal Chemistry Letters, 2004, 14:3669-3673.

Chen et al., "Synthesis and Oral Efficacy of a 4-(Bulylethylamino)pyr-rolo[2,3-d]pyrimidine: A Centrally Active Corticotropin-Releasing Factor: Receptor Antagonist," J. Med. Chem., 1997, 40:1749-1754.

Cheng and Robins, "Potential purin antagonists. VI. Synthesis of 1-alkyl and 1-aryl-4-substituted pyrazolo[3,4-d]pyrimidines," J. Org Chem, 1956, 21:1240-1256.

Cheng, "Rosuvastatin in the Management, of Hyperlipidemia." Clinical Therapeutics, 2004, 26(9): 1368-1387.

Cheng-Lai, "Cerivastatin," Heart Disease, 2000, (2):93-99.

Cheng-Lai, Rosuvastatin: A New HMG-CoA Reductase Inhibitor for the Treatment of Hypercholesterolemia; Heart Disease. 5(1). 72-78 (2003).

Chorvat et al., "Synthesis, Corticotropin-Releasing Factor Receptor Binding Affinity, and Pharmacokinetic Properties of Triazolo-, Imidazo-, and Pyrrolopyrimidines and -pyridines," J. Med. Chem., 1999, 42:833-848.

Chu et al., "A Role for Intestinal Endocrine Cell-Expressed GPR119 in Glycemic Control by Enhancing GLP-I and Glucose-Dependent Insulinotropic Peptide Release," Endocrinology, 2008, 149(5):2038-2047.

Chu et al., "A role for B-cell-expressed G protein-coupled receptor 119 in glycemic control by enhancing glucose-dependent insulin release," Endocrinology, 2007, 148:2601-2609.

Chu, "Section 1: Drug Development," Cancer: Principles and Practice of Oncology, 2005, Lippincott Williams & Wilkins, 27 pages.

Citkowitz, "Hypertriglyceridemia," eMedicine Endorinology, Jul. 2008, http://emedicine.medscape.com/article/126568-print, retrieved on Sep. 24, 2014, 18 pages.

Clark et al., "Synthesis and Analgesic Activity of 1,3-Dihydro-3-(Substituted phenyl)imidazo(4,5-b]pyridine-2-ones and 3-(Substituted phenyl)-1,2,3-triazolo(4,5bpyridines," J. Med. Chem., 1978, 21(9):965-978.

Clark, "Treating Dyslipidemia with Statins: The Risk-Benefit Profile," American Heart Journal, 2003, 145(3):387-396.

Cleveland Clinic [online], "Metabolic Svndrome," Dec. 2009, retrieved on Sep. 24, 2014. retrieved from URL <http://my.clevelandclinic.org/disorders/metabolic_syndrome/hic_metabolic_syndrome.aspx>, 2 pages.

Clinical Trials [online], "Efficacy and Safety of Etrasimod (APD334) in Inflammatory Bowel Disease Patients With Active Skin Extraintestinal Manifestations," Dec. 31, 2020, Retrieved Jan. 25, 2022, retrieved from URL <https://clinicaltrials.gov/ct2/show/NCT03139032?term=etrasimod&draw=3&rank=13>, 32 pages.

Cocco et al., "Transformation of 6-Methylthiopyrimidines. Preparation of New Pyrimidine Derivatives and Fused Azolopyrimidines," Journal of Heterocyclic Chemistry, 2000, 37(4):707-710.

Cocuzza et al., "Use of the suzuki reaction for the synthesis of aryl-substituted heterocycles as corticotropin-releasing hormone (CRH) antagonists," Bioorganic & Medicinal Chemistry Letters, 1999, 9:1063-1066.

Cohen et al., "The Preparation and Properties of 6-Halomethylpurines," Div. of Nucleoprotein Chemistry . Sloan-Kettering Institute for Cancer Research, and Sloan Kettering Div. Grad. School of Med. Sci., Cornell Univ. Med. College, 1962, 27:3545-3549.

Colandrea et al., "Synthesis and regioselective alkylation of 1,6-and 1,7-naphythridines," Tetrahedron Letters, 2000, 41:8053-8057.

Cossey et al, "Pyridines and pyridinium salts from cyanoacetamides," Australian Journal of Chemistry, 1976, 29(5):1039-1050.

Cover Sheet and 23 Compounds, ChemCats file, 11 pp., (2006).

Cover Sheet and 1185 Compounds, CAS Registry and ChemCats files, 391 pp., (various dates—Jan. 12, 2005-Nov. 10, 2006).

Cover Sheet and 18 Compounds, CAS Registry, 9 pp., (various dates—Aug. 1, 2004-Jan. 13, 2005).

Cover Sheet and 2534 Compounds, CAS Registry and ChemCats files, 817 pp., (various dates—Feb. 7, 2006-Nov. 6, 2006).

Cover Sheet and 54 Compounds, CAS Registry and ChemCats files, 23 pp., (various dates—Jan. 15, 1998-Jun. 16, 2004).

Cox, "Peptide YY: A neuroendocrine neighbor of note," Peptides, 2007, 28:345-351.

Crosby et al., "030 Etrasimod, an oral, selective sphingosine 1-phosphate receptor modulator improves skin inflammation in a contact hypersensitivity dermatitis model," Journal of Investigative Dermatology, 2019, 139(9):Supplement 219, 1 page.

Crouse, et al., "Measuring Effects on Intima Media Thickness: An Evaluation of Rosuvastatin in Subclinical Atheroslerosis-The Rationale and Methodology of the Meteor Study," Cardiovascular Drugs and Therapy, 2004, 18(3):231-238.

Craze et al., "The Y2 receptor mediates increases in collateral-dependent blood flow in a model of peripheral arterial insufficiency," Peptides, 2007, 28:269-280.

Cryan et al., "Behavioral characterization of the novel GABAB receptor-positive modulator GS39783 (N,N'-dicyclopentyl-2-methylsulfanyl-5-nitro-pyrimidine-4,6-diamine): anxiolytic-like activity without side effects associated with baclofen or benzodiazepines," Journal of Pharmacology and Experimental Therapeutics, 2004, 310(3):952-963.

Dai et al., "The First General Method for Palladium-Catalyzed Negishi Cross-Coupling of Aryl and Vinyl Chlorides: Use of Commercially Available Pd/P(t-Bu)3)2 as a Catalyst," J. Am. Chern. Soc., 2001, 123(12):2179-2724.

(56) References Cited

OTHER PUBLICATIONS

Davidson, "Rosuvastatin: A Highly Efficacious Statin for the Treatment of Dyslipidemia," Expert Opinion on Investigational Drugs, 2002, 11(3):455.
De Denus et al., "Dyslipidemias and HMG-CoA Reductase Inhibitor Prescription in Heart Transplant Recipients," Annals of Pharmacotherapy, 2004, 28 (7/8):1136-1141.
Deacon et al., "Degradation of Endogenous and Exogenous Gastric Inhibitory Polypeptide in Healthy and in Type 2 Diabetic Subjects as Revealed Using a New Assay for the Intact Peptide," The Journal of Clinical Endocrinology & Metabolism, 2000. 85:3575-3581.
Deacon, "Therapeutic Strategies Based on Glucagon-Like Peptide 1," Diabetes, Sep. 2004, 53:2181-2189.
Deacon," What do we know about the secretion and degradation of incretin hormones?" Regul Pept, 2005, 128:117-124.
Deighan, et al., "Comparative Effects of Cerivastatin and Fenofibrate on the Atherogenic Lipoprotein Phenotype in Proteinuric Renal Disease," Journal of the American Society of Nephrology, 2001, 12(2):341-348.
Delmas and Meunier, "The Management of Paget's Disease of Bone." The New England Journal of Medicine, Feb. 1997, 336:558-566.
Demuth et al., "Type 2 diabetes—Therapy with dipeptidyl peptidase IV inhibitors," Biochimica et Biophysica Acta (BBA), 2005, 1751(1):33-44.
Desimoni et al, "Polynuclear Isoxazole Types-I-Isoxazolo[4,5-d]Pyrimidines," Tetrahedron, 1967, 23:675-680.
Devita et al. "Identification and initial structure-activity relationships of a novel non-peptide quinolone GnRH receptor antagonist," Bioorg & Med Chem Ltrs, 1999, 9(17):2615-2620.
Di Braccio et al., "Synthesis and preliminary pharmacological examination of 2,4-disubstituted N,N-dialkyl-1,8-napthyridine-3-carboxamides," Farmaco (1989) 44(9):865-881.
Ding et al., "A Combinatorial Scaffold Approach toward Kinase-Directed Heterocycle Libraries" J. Am, Chem. Soc. (2002) 124:1594-1596.
Dorwald, Side Reactions in Organic Synthesis, 2005, Wiley (table of Contents Only).
Drucker et al., "The incretin system: glucagon-like peptide-1 receptor agonists and dipeptidyl peptidase-4 inhibitors in type 2 diabetes," 'The Lancet, 2006. 368:1696-1705.
Drucker, "The biology of incretin hormones," Cell Metabolism, 2006, 3:153-165.
Dubau-Assibat et al., "Lawesson's Reagent: An Efficient 1,3-Dipole Trapping Agent", J. Org. Chem., 1995, 60(12):3904-3906.
Dugue et al., "Detection and Incidence of Muscular Adverse Drug Reactions: A prospective Analysis from Laboratory Signals," European Journal of Clinical Pharmacology, 2004, 60(4):285-292.
During et al., "Glucagon-like peptide-1 receptor is involved in learning and neuroprotection," Nat. Med., 2003, 9:1173-1179.
Dzierba et al., "Synthesis, Structure-Activity Relationships, and in Vivo Properties of 3,4-Dihydro-1H-pyrido[2,3-b]pyrazin-2-ones as Corticotropin-Releasing Factor-1 Receptor Antagonists," Journal of Medicinal Chemistry, 2004, 47(23):5783-5790.
Eberlein et al., "A New Molecular Form of PYY: Structural Characterization of Human PYY (3-36) and PYY(1-36)," Peptides, 1989, 10:797-803.
Edmondson et al., "Potent and selective proline derived dipeptidyl peptidase IV inhibitors," Bioorg. Med. Chem. Lett., 2004, 14:5151-5155.
Eicher et al., "Reaction of Triafulvenes with Isonitriles. A simple synthesis of diphenyl-substituted functionalized cyclobutene derivatives and related products," Synthesis (1987)(7):619-626.
Ekblad et al., "Distribution of pancreatic polypeptide and peptide YY," Peptides, 2002, 23:251-261.
Ekstrand et al., "Deletion of neuropeptide Y (NPY) 2 receptor in mice results in blockage of NPY-induced angiogenesis and delayed wound heating," PNAS USA, 2003, 100:6033-6038.

El Bahb et al., "The anti-epileptic actions of neuropeptide Y in the hippocampus are mediated by Y2 and not Y5 receptors," Eur. J. Neurosci., 2005, 22:1417-1430.
emedicinehealth.com [online], "High Blood Sugar" available on or before Jan. 23, 2016. via Internet Archive: Wavback Machine URL <http://web.archive.org/web/2016*/http://www.emedicinehealth.com/high_blood_sugar_hyperglycemia/page9_em.htm>, retrieved on Jul. 1, 2011, URL<http://www.emedicinehealth.com/high_blood_sugar_hyperglycemia/page9_em.htm>, 2 pages.
Escher et al., "Cyclopentylamine Substituted Triazolo[4,5-D]Pyrimidine: Implications for Binding to the Adenosine Receptor," Tetrahedron Letters (1991) 32(29):3583-3584.
Estel et al., "Synthesis of Ortho-Substituted Aminopyridines. Metalation of Pivalovlamino Derivatives," J. Heterocyclic Chem., 1989, 26:105-112.
Fellstrom, et al, "Why Do We Need a Statin Trial in Hemodialysis Patients?" Kidney International Supplement, 2003 63(84):S204-S206.
Feng et al., "Research Progress on Extraintestinal Manifestations of Inflammatory Bowel Disease," Journal of Gastroenterology and Hepatology, 2015, 24(6):631-640 (with English abstract).
Fischer et al., "What rheumatologists can learn from gastroenterologists," Zeitschrif für Rheumatologie, 2018, 77(6):460-468, 10 pages (with English abstract).
Flock et al., "GPR119 Regulates Murine Glucose Homeostasis Through Incretin Receptor-Dependent and Independent Mechanisms," Endocrinology, Feb. 2011, 152(2):374-383.
Fyfe et al. "GPR119 agonists as potential new oral agents for the treatment of type 2 diabetes and obesity," Expert Opinion on Drug Discovery, 2008, 3(4):403-413.
Fyfe et al., "GPR119 Agonists Are Potential Novel Oral Agents for the Treatment of Diabesity," Diabetes, 2007, 56(1):A142 (Abstract).
Gangloff et al., "Synthesis of 3,5-disubstituted-l,2,4-oxadiazoles using tetrabutylammonium fluoride as a mild and efficient catalyst," Tetrahedron Letters, 2001, 42:1441-1443.
Garcia, et al., "Effects of Cerivastatin in Dvslipemia and Other Cardiovascular Risk Factors after Renal Transplantation." Transplantation Proceedings, 2002, 34(1):401-402.
GeneMedRX [online], "Cytochrome P-450 (CYP) Metabolism Reference Table," available on or before Nov. 8, 2017, via Internet Archive: <https://web.archive.org/web/20171108224330/http://www.genemedrx.com/Cytochrome_P450_Metabolism_Table.php>, retrieved on Mar. 23, 2022, URL <http://www.genemedrx.com/Cytochrome_P450_Metabolism_Table.php>, 3 pages.
Gewald and Bellmann, "Synthese und Reaktionen von 4-Aminoisothiazolen," Liebigs Annalen der Chemie, 1979, 10:1534-1546.
Gilligan et al., "Corticotropin-releasing factor antagonists: Recent advances and exciting prospects for the treatment of human diseases," Current Opinion in Drag Discovery & Development, 2004, 7(4):487-497.
Gilligan, et al., "Corticotropin Releasing Factor (CRF) Receptor Modulators: Progress and Opportunities for New Therapeutic Agents," J. Med. Chem, 2000, 43(9):1641-1660.
Giner-Sorolla et al., "The Synthesis and Properties of 6-Mercaptomelhyipurine and Derivatives," Cornell University Medical College, 1965, 8:667-672.
Girouard and Iadecola, "Neurovascular coupling in the normal brain and in hypertension, stroke and Alzheimer disease," J. Appl. Physiol., 2006, 100:328-335.
Goldner et al., "Die Darstellung 2, 9-; 2, 6,9- and 6,9-snbstituierter Purine," Journal fuer Praktische Chemie (Leipzig), 1961, 12:242-252.
Gomez et al., "Intestinal peptide YY: ontogeny of gene expression in rat bowel and trophic actions on rat and mouse bowel," Am. J. Physiol., 1995, 268:G71-G81.
Gomtsyan et al., "Design, synthesis, and structure—activity relationship of 6-alkynylpvrimidines as potent adenosine kinase inhibitors," J Med Chem. (2002) 45(17):3639-3648.
Gonon et al.,"Adiponectin protects against myocardial ischaemia-reperfusion injury via AMP-activated protein kinase, Akt, and nitric oxide," Cardiovasc Res., 2008, 78:116-122.

(56) References Cited

OTHER PUBLICATIONS

Grandi et al., "Two molecular forms of Peptide YY (PYY) are abundant in human blood: characterization of a radioimmunoassay recognizing PYY 1-36 and PYY 3-36," Regul. Pept., 1994, 51:151-159.
Greig et al., "New Therapeutic Strategies and Drug Candidates for Neurodegenerative Diseases: p53 and TNF-α Inhibitors, and GLP-1 Receptor Agonists," Ann NY Acad Sci, 2004, 1035:290-315.
Grise et al, "Peptide YY Inhibits Growth of Human Breast Cancer in Vitro and in Vivo," J. Surg. Res., 1999, 82:151-155.
Groger "Moderne methoden der Suzuki-kreuzkupplung: die langerwarteten universellen synthesevarianten mit arylchloriden," J Prakt Chem , 2000, 342(4):334-339 (English Abstract).
Guerre-Millo, "Adiponectin: An Update," Diabetes & Metabolism, 2008, 34:12-18.
Guerrero et al., "Sphingosine 1-phosphate receptor 1 agonists: a patent review (2013-2015)," Expert Opinion on Therapeutic Patents, 2016, 26(4):455-470, 41 pages.
Guilherme et al., "Adipocyte dysfunctions linking obesity to insulin resistance and type 2 diabetes," Molecular Cell Biology, May 2008, 9:367-377.
Gundersen "Synthesis of purinecarbonitriles by Pd(0)-catalvsed coupling of halopurines with zinc cyanide," Acia Chemica Scandinavia (1996) 50:58-63.
Hafenbradl et al., "In vitro Characterization of Small-Molecule Kinase Inhibitors," Protein Kinase as Drag Targets, 2011 (B. Kiebl et al. eds) 185 pages.
Hamada et al., "An Improved Synthesis of Arylsulfonyl Chlorides From Aryl Halides," Synthesis, 1986, 852-854.
Hausmann et al., "Pulmonary Arterial Hypertension is Linked to Insulin Resistance and Reversed by Peroxisome Proliferator-Activated Receptor-γ Activation," Circulation, 2007, 115:1275-1284.
Hara et al., "Measurement of the High-Molecular Weight Form a Adiponectin in Plasma is Useful for tire Prediction of Insulin Resistance and Metabolic Syndrome," Diabetes Care, 2006, 29:1357-1362.
Hay et al, "Inflammator Bowel Disease: Costs-of-Illness," J Clin Gastroenterol. 1992. 14:309-317.
He et al., "4-(1,3-Dimethozyprop-2-ylamino)-2,7-dimethyl-8-(2,4-dichlorophenyl)-pyrazolo[1,5-al-1,3,5-triazine: A Potent, Orally Bioavailable CRF1 Receptor Antagonist," J. Med. Chem., 2000, 43:449-456.
Hecht et al., "On the 'activation' of cytokins," J Biological Chemistry, 1975, 250(18):7343-7351.
Hersperger et al., "Palladium-Catalyzed Cross-Coupling Reactions for the Synthesis of 6,8-Disubstituted 1,7-Naphthyridines: A Novel Class of Potent and Selective Phosphodiesterase Type 4D Inhibitors," J. Med. Chem., 2000. 43:675-682.
Hill and Peters, "Environmental Contributions to the Obesity Epidemic." Science, 1998, 280:1371-1374.
Hincheliff et al., "Systemic Sclerosis/Scleroderma: A Treatable Multisystem Disease," Am Fam Physician, Oct. 2008, 78(8):961-968.
Hocek et al., "An Efficient. Synthesis of 2-Substituted 6-Methylpurine Bases and Nucleosides by Fe- or Pd-Catalyzed Cross-Coupling Reactions of 2,6-Dichloropurines," J. Org. Chem., 2003, 68:5773-5776.
Holdgate et al., "Molecular Mechanism for Inhibition of 3-hydroxy-3-methyglutaryl CoA (HMG-CoA) Reductase by Rosuvastatin," Biochemical Society Transactions, 2003, 31(3):528-531.
Huang et al., "Synthesis and Antiplatelet Activity of Phenyl Quinolones," Bioorganic & Medicinal Chemistry, 1998, 6:1657-1662.
International Standard, "Determination of the specific surface area of solids by gas adsorption—BET method," 2010, Second Edition, 1-24.
Irwin et al., "Therapeutic potential of the original incretin hormone glucose-dependent insulinotropic polypeptide: diabetes, obesity, osteoporosis and Alzheimer's disease," Expert Opinion Investi. Drugs, 2010, 19(9): 1039-1048.

Ismail et al., "Number and Type of Vertebral Deformities: Epidemiological Characteristics and Relation to Back Pain and Height Loss," Osteoporosis International, 1999, 9:206-213.
Jia et al., "Design, Synthesis and Biological Activity of Novel Non-Amidine Factor Xa Inhibitors. Part 1: P1 Structure-Activity Relationships of the Substituted 1-(2-Naphtyl)-1H-pyrazoie-5-carboxylamides," Bioorganic & Medicinal Chemistry Letters, 2002, 12:1651-1655.
Jogie et al., "Unusual protein-binding specificity and capacity of aza-arenophilic gels," Journal of Molecular Recognition, 1998, 11:261-262.
Jones and Leonard, "The Emergence of GPR119 Agonists as Anti-Diabetic Agents," Ann. Rep. Med. Chem., 2009, 44:149-170.
Jones et al. "GPR119 agonists for the treatment of type 2 diabetes," Expert Opin. Ther. Patents, 2009, 19(10): 1339-1359.
Jones, "The Discovery of APD334, A Selective S1P1 Functional Antagonist", EFMC-ISMC (2014), Sep. 8, 2014 (PowerPoint), 22 pages.
Jones, Robert M., "Discovery of Potent and Selective Sphingosine-1-Phosphate I(SIPI) Receptor Agonists", CHI 6th Annual Discovery on Target, Boston, MA, Nov. 3, 2011, 26 pages.
Joshi et al., "Endogenous PYY and GLP-1 mediate L-glutamine responses in intestinal mucosa," British Journal of Pharmacology, 2013, 170:1092-1101.
Judge and Bever. "Potassium channel blockers in multiple sclerosis: neuronal Kv channels and effects of symptomatic treatment," Pharmacology & Therapeutics, 2006, 111:224-259.
Kametani et al. "Benzvene Reaction. IX. Benzyene Reaction of o-halobenzenes with acetonitrile or phenylacetonitrile in organic solvents," J. Org. Chern., 1972, 36(2):327-330.
Kanstrup et al., "Quality of Lipid-Lowering Therapy in Patients with Ischaemic Heart disease: A Register-Based Study in 3477 Patients," Journal of Internal Medicine, 2004, 255(3):367-372.
Kawakita et al., CAPLUS Abstract 115:136096, 1991, 3 pages.
Kawase et al., "a-trifluoromethylated acyloins induce apoptosis in human oral tumor cell hues," Bioorg & Med Chem Ltrs, 1999, 9(21):3113-3118.
Keane et al., "The CHORUS (Cerivastatin in Heart Outcomes in Renal Disease: Understanding Survival) Protocol: A Double-Blind, Placebo-Controlled Trial in Patients with ESRD," American Journal of Kidney Diseases, 2001, 37(1, Suppl. 2):S48-S53.
Keighley and Stockbrgger, "Inflammatory bowel disease," Ailment Pharmacol Ther, 2003, 18:66-70.
Keire et al., "Primary structures of PYY, [Pro34] PYY, and PYY-(3-36) confer different conformations and receptor selectivity," Am. J. Physiol, Gastrointest. Laver Physiol., 2000, 279:G126-G131.
Kelley et al., "Benzodiazepine receptor binding activity of 8-substituted-9-(3-substituted-benzyl)-6 diamethylammo)-9H-purines," Med Chem, 1990, 33(1):196-202.
Kelly et al., "A Synthesis of Aaptamine," Tetrahedron,1985, 41(15):3033-3066.
Kempson et al.. "Fused pyrimidine based inhibitors of phosphodiesterase 7 (PDE7): svnthesis and initial" structure-activity relationships, Bioorganic & Medicinal Chemistry Letters, 2005, 15:1829-1833.
Khattab et al., "Quinolines with heteroatom substituents in position 2 and 4. Nucleophilic substitution of 2,4-dichloro-3-phenylquinolines," ACH—Models in Chemistry, 1994, 131(3-4):521-527.
Kim and Egan, "The Role of Incretins in Glucose Homeostasis and Diabetes Treatment," Pharmacological Reviews, 2008, 60(4):470-512.
Klotzer et al., "Chlorierende formylierungsreaktionen an pyrimidinen," Monatshefte fuer Chemie, 1965, 96(5):1567-1572 (English Abstract).
Kolosov et al., "The interaction between 4-[phenyl-5-acetyl-6-methyl-3,4-dihydropyrimidine-2-one and 4-brombenzaldehyde", Institute of Organic Chemistry, Kharkiv, retrieved on Mar. 30, 2008, http://conf.iflab.kiev.ua/eng/reports/show/?id=926, 2 pages (Abstract Only).
Komori et al., "Effect of Etrasimod on Circulating Lymphocyte Subsets: Data from a Randomized Phase 1 Study in Healthy Japanese and Caucasian Men", The American Journal of Gastroenterology, Dec. 2020, 115: pS12.
Kotian et al., "Synthesis, ligand binding, and quantitative structure-activity relationship study of 3β-(4'-substituted phenyl)-2β-

(56) References Cited

OTHER PUBLICATIONS heterocyclic tropanes: evidence for an electrostatic interaction at the 2β-position," J Med Chem, 1996, 39(14):2753-2763.
Koumbourlis, "Scoliosis and the respiratory system," Paediatric Respiratory Reviews, 2006. 7:152-160.
Kovarick et al., "Multiple-Dose FTY720: Tolerability, Pharmacokinetics, and Lymphocyte Responses in Healthy Subjects," The Journal of Clinical Pharmacology, May 2004, 44(5):532-537.
Krauze et al., "Derivatives of 3-cyano-6-phenyl-4-(3'-pyridyl)-pyridine-2(1H)-thione and their neurotropic activity," European Journal of Medicinal Chemistry, 1999, 34(4):301-310.
Krauze et al., "Synthesis of 3-oxoisothiazolo[5,4-b]pyridines," Khimiya Geterotsiklicheskikh Soedinenii. 1982, (4):508-512.
Kreisberg et al., "Hyperlipidemia (High Blood Fat)," The Journal of Clinical Endocrinology & Metabolism, 2005, 90:0, 2 pages.
Kubota et al, "Disruption of Adiponectin Causes Insulin Resistance and Neointimal Formation," J. Biol. Chem., 2002, 2002, 277:25863-25866.
Kumagai et al., "Synthesis, SAR and biological activities of CRH1 Receptor: Novel 3- or 4-carbamoyl-1,2,5,6- tetrahydropyridinopyrrolopyrimidine derivative," 4th ACS National Meeting, Aug. 18-22, 2002, Boston, MA. Poster #259, 1 page.
Lai et al., "Association between Obesity and Hyperlipidemia Among Children," Yale Journal of Biology and Medicine 74 (2001), pp. 205-210.
Lai et al., "A one-pot method for the efficient conversion of aryl-and acyl-substituted methyl alcohols into chlorides," Synthetic Communications, 2003, 33(10): 1727-1732.
Lan, "GPR119 is Required for Physiological Regulation of Gucagon-like Peptide-1 Secretion but not for Metabolic Homeostasis," J. Endocrinol., 2009, 201:219-230.
Lanier et al., "Small molecule corticotrophin-releasing factor antagonists," Expert Opinion, 2002, 12(11):1619-1630.
Le Stunff and Bougneres, "Early Changes in Postprandial Insulin Secretion, Not in Insulin Sensitivity, Characterize Juvenile Obesity," Diabetes, 1994, 43:696-702.
Leadbeater el al., "First Examples of Transition-Metal Free Sonogashira-Type Couplings," Organic Letters, 2003, 5(21):3919-3922.
Leadbeater et al., "Transition-metal Free Sonogashira-type Couplings," Organic Letters, 2003 5(21):-3922.
Lechleitner, "Dyslipidaemia and Renal Disease—Pathophysiology and Lipid Lowering Therapy in Patients with Impaired Renal Function," Journal of Clinical and Basic Cardiology. 2000. 3(1):3-6.
Lee et al., "Neuropeptide Y induces ischemia angiogenesis and restores function of ischemic skeletal muscles," J. Clin. Invest., 2003, 111:1853-1862.
Lee et al., "Impaired angiogenesis in neuropeptide Y (NPY)-Y2 receptor knockout mice," Peptides, 2003, 24:99-106.
Lee et al., "Synthesis and biological evaluation of clitocine analogues as adenosine kinase inhibitors," Bioorg & Med Chem Ltrs, 2001, 11(18):2419-2422.
Leese el al., "Potential antipurines. Part II. Synthesis of 6- and 9-substituted purines and 8-azapurines," Journal of the Chemical Society. 1958. 4107-4110.
LeWitt, "Levodopa for the Treatment of Parkinson's Disease," The New England Journal of Medicine, Dec. 2008, 359(23):2468-2476.
Lin, et al., "Synthesis and Antitumor Activity of Halogen-Substituted 4-(3,3-Dimethyl-1-triazeno)uinolones," J. Med. Chem., 1978, 21(3):268-272.
Lindvall and Kokaia, "Stem cells for the treatment of neurological disorders," Nature, 2006, 441:1094-1096.
Litvak et al., "Polynucleotides and Their Components in the Processes of Aromatic Nucleophilic Substitution: II.1 Nucleophilic Modification of 3',5'-Bis-O-(α, β, α',β'-tetrafluoropyrid-y-y1)thymidine," Russian Journal of Bioorganic Chemistry, 2004, 30(4):337-343.
Litvinov et al., "Naphthyridines. Structure, physicochemical properties and general methods of synthesis," Russian Chemical Reviews, 2000, 69(3):201-220.

Liu et al, "Human Pancreatic Cancer Growth is inhibited by Peptide YY and BIM-43004-1," J. Surg. Res., 1995, 58:707-712.
Liu et al., "Pancreatic Peptide YY mRNA Levels Increase during Adaptation after Small Intestinal Resection," J. Surg. Res., 1995, 58:6-11.
Liu et al., "Peptide YY: A Potential Proabsorptive Hormone for the Treatment of Malabsorptive Disorders," Am Surg., 1996, 62:232-236.
Liu et al, "Y2 receptors decrease human pancreatic cancer growth and intracellular cyclic adenosine monophosphate levels," Surgery, 1995, 118:229-236.
Loupy et al., "Easy and efficient SNAr Reactions on halopyridines in solvent free conditions," Heterocycles, 1991, 32(10):1947-1952.
Lumb et al., "Novel Selective Neuropeptide Y2 Receptor PEGylated Peptide Agonists Reduce Food Intake and Body Weight in Mice," J. Med. Chem., 2007, 50:2264-2268.
Lundberg et al., "Localization of peptide YY (PYY) in gastrointestinal endocrine cells and effects on intestinal blood flow and motility," PNAS USA, 1982, 79:4471-4475.
Luo et al., "Clinical manifestations and therapy of extraintestinal manifestations with inflammatory bowel disease," International Journal of Digestive Diseases, 2006, pp. 87-90 (with English abstract).
Luo et al., "Microwave-assisted synthesis of aminopyrimidines," Tetrahedron Letters, 2002, 43:5739-5742.
Ma, et at. "Mild Method for Ullmann Coupling Reaction of Amines and Aryl Halides," Organic Letters, 2003, 5(14):2453-2455.
Macchia et al., "New N-n-propyl-substituted 3-aryl- and 3-cyclohexylpiperidines as partial agonists at the D4 dopamine receptor," J Med Chem, 2003, 46(1):161-168.
Mackman et al., "2-(2-Hydroxy-3-alkoxyphenyl)-1H-benzimidazole-5-carboxamidine derivatives as potent and selective urokinase-type plasminogen activator inhibitors," Bioorganic & Medicinal Chemistry Letters, 2002, 12(15):2019-2022.
Maeda el al., "Diet-induced insulin resistance in mice lacking adiponectin/ACRP30," Nat. Med, 2002, 8:731-737.
Majeed et al., "Stannylation Reactions and Cross-Couplings in Pyrimidines," Tetrahedron, 1989, 45(4):993-1006.
Markwalder, et al., "Synthesis and biological evaluation of 1-aryl-4,5-dihydro-1H-pyrazolo[3,4-d]pyrimidin-4-one inhibitors of cyclin-dependent kinases", J. Med. Chem., (2004), 47:5894-5911.
Marso et al., "Low Adiponectin Levels are Associated with Atherogenic Dyslipidemia and Lipid-Rich Plaque in Nondiabetic Coronary Arteries," Diabetes Care, 2008, 31:989-994.
Martin et al., "A Double-Blind, Randomized, Incomplete Crossover Trial to Assess the Dose Proportionality of Rosuvastatin in Healthy Volunteers," Clinical Therapeutics, 2003, 25(8):2215-2224.
Martin et al., "Absolute Oral Bioavailability of Rosuvastatin in Healthy White Adult Male Volunteers," Clinical Therapeutics, 2003, 25(10):2553-2563.
Martin et al., "An Open-Label, Randomized, Three-Way Crossover Trial of the Effects of Coadministration of Rosuvastatin and Fenofibrate on the Pharmacokinetic Properties of Rosuvastatin and Fenofibric Acid in Healthy Male Volunteers," Clinical Therapeutics, 2003, 25(2): 459-471.
Martin et al.. "Metabolism, Excretion, and Pharmacokinetics of Rosuvastatin in Healthy Adult Male Volunteers," Clinical Therapeutics, 2003, 25(11):2822-2835.
Matsuda et al., "Role of Adiponectin in Preventing Vascular Stenosis: The Missing Link of Adipo-Vascular Axis," J Biol Chem, 2002, 277:37487-37491.
Matsui et al., "Highly Potent Inhibitors of TNF—A Production. Part II: Metabolic Stabilization of a Newly Found Chemical Lead and Conformational Analysis of an Active Diastereoisomer," Bioorganic & Medicinal Chemistry, 2002, 10(12):3787-3805.
Matsuno et al., "Potent and Selective Inhibitors of Platelet-Derived Growth Factor Receptor Phosphorylation. 3. Replacement of Quinazoline Moiety and Improvement of Metabolic Polymorphism of 4-[4-N-Substituted (thio) caramoyl)-1-piperazinyl]-6,7-diamethoxyquinazoline Derivatives," J Med Chem, 2003, 46(23):4910-4925.

(56) References Cited

OTHER PUBLICATIONS

MayoClinic.com [online], "Type 2 diabetes," Jan. 2021, retrieved on Mar. 24, 2022, retrieved from URL <https://www.mayoclinic.org/diseases-conditions/type-2-diabetes/svmptoms-causes/syc-20351193>, 8 pages.

MayoClinic.com [online], "Obesity," Sep. 2021, retrieved on Mar. 24, 2022, retrieved from URL <https://www.mayoclinic.org/diseases-conditions/obesiiy/symptoms-causes/syc-20375742>.

MayoClinic.com [online],"Metabolic syndrome," May 2021, retrieved on Mar. 24, 2022, retrieved from URL <https://www.mayoclinic.org/diseases-conditions/metabolic-syndrome/symptoms-causes/syc-20351916>, 4 pages.

McFadden et al., "Peptide YY inhibits the growth of Barrett's esophageal adenocarcinoma in vitro," Am. J. Surg., 2004, 188:516-519.

McIntosh et al., "Dipeptidvl peptidase IV inhibitors: How do they work as new antidiabetic agents," Regulatory Peptides, 2005, 128:159-165.

Mentlein, "Therapeutic assessment of glucagon-like peptide-1 agonists compared with dipeptidyl peptidase IV inhibitors as potential antidiabetic drugs," Expert Opin Investig Drugs, 2005, 14(1):57-64.

Mesguiche et al., "4-Alkoxy-2,6-diaminopyrimidine Derivatives: Inhibitors of Cyclin Dependent Kinases 1 and 2," Bioorganic & Medicinal Chemistry Letters, 2003, 13(2):217-222.

Metzger et al., "Einstufensynthese von 2,4-Bis(sec-alkylamino-6-halogen-3-pyridincarbonitrilen** ," Liebigs Annalen der Chemie, 1980, 6:946-953 (with English abstract).

Mitchell and Borasio, "Amyotrophic lateral sclerosis," The Lancet, Jun. 2007, 369: 2031-2041.

Mitsunobu, "The Use of Diethyl Azodicarboxylate and Triphenylphosphine in Synthesis and Transformation of Natural Products", Synthesis, 1981, 1-28.

Mittelbach and Jmek. "Syntheses with Nitriles. 60. (1). Preparation of 4-Amino-5-cyano-6-phenylpyrimidines from 2-Amino-1,1-dicyano-2-phenylethene," J. Heterocyclic Chem, 1980, 17(7):1385-1387.

Miyashita et al., "Preparation of Heteroarenecarbonitriles by Reaction of Haloheteroarenes with Potassium Cyanide Catalyzed by Sodium p-Toluenesulfinate." Heterocycles, 1994, 39(1):345-350.

Mohan et al., "Solid-Phase Synthesis of N-Substituted Amidinophenoxy Pyridines as Factor XA Inhibitors," Bioorganic & Medicinal Chemistry Letters, 1998, 8(14):1877-1882.

Mombereau et al., "Genetic and Pharmacological Evidence of a Role for $GABA_B$ Receptors in the Modulation of Anxiety- and Antidepressant-Like Behavior," Neuropsychopharmacology, 2004, 29(6): 1050-1062.

Mongin and Queguiner, "Advances in the directed metallation of azines and diazines (pyridines, pyrimidines, pvrazines, pyridazines, quinolines, benzodiazines and carbolines). Part 1: Metallation of pyridines, quinolines and carbolines," Tetrahedron, 2001, 57(19):4059-4090.

Montgomery et al., "Isonucleosides. I. Preparation of Methyl 2-Deoxy-2-(purin-9-yl)arabinofuranosides and Methyl 3-Deoxy-3-(purin-9-y1) xylofuranosides," Journal of Organic Chemistry, 1975, 40(13):1923-1927.

Morimoto et al., "Potent and selective ET-A Antagonists, 1. Syntheses and Structure-Activity Relationships of N-(6-(2-(Aryloxy)ethoxy)-4-pyrimidinyl)sulfonamide Derivatives," J Med Chem, 2001, 44(21):3355-3368.

Moshchitskii et al., "Reaction of 2, 3, 5, 6-tetrachloro-4-pyridyl vinyl sulfone with nucleophilic agents," Khimiya Geterotsiklicheskikh Soedinenii,1972, 1634-1637. (Translated pp. 1482-1485).

Mosti et al., "4-Substituted 1-Phenyl-1H-Indazoles With Analgesic, Antiinflammatory, Antipyretic and Local Anesthetic Activities," IL Farmaco, 1990, 45(4):415-429.

Mosti et al., "Synthesis and Preliminary biological Evaluation of Novel N-Substited 1-Amino-3-[1-methyl(phenyl)-1H-indazol-4-yloxy]-propan-2-ols Interesting as Potential Antiarrhythmic, Local Anaesthetic and Anagesic Agents," Arzneim-Forsch Drug Res, 2000, 50(11):963-972.

Muci and Buchwald, "Practical Palladium Catalysts for C-N and C-O Bond Formation," Topics in Current Chemistry, 2002, 219:131-209.

Muck et al., "Lack of Pharmacokinetic Drug-Drug Interaction between Orlistat and Cerivastatin." Clinical Drag Investigation, 2000, 19(1):71-73.

Muller et al., "7-Deaza-2-phenyladenines: Structure-Activity Relationships of Potent $A_1$ Selective Adenosine Receptor Antagonists," J Med Chem, 1990, 33:2822-2828.

Nakamura el al., "Effect of Cerivastatin on Endothelial Dysfunction and Aortic CD36 Expression in Diabetic Hyperlipidemic Rats," Hypertens Res, 2004, 27(8):589-598.

Nakazato et al., "Design, synthesis and structure-affinity relationships of 4-methylidenepiperidine and 4-aryl-1,2,3,6-tetrahydropyridine derivatives as corticotropin-releasing factor1 receptor antagonists," Bioorganic & Medicinal Chemistry, 2000, 8(5):1183-1193.

Nakazato et al., "Synthesis, SAR and biological activities of CRH1 receptor: Novel 3- or 4-carbamoyl-1, 2,5,6-tetrahydropyridinoquinoline derivative," 24th ACS National Meeting, Aug. 18-22, 2002, Boston, MA. Poster #258, 1 page.

National Diabetes Information Clearinghouse [online] "Insulin resistance and Pre-Diabetes," last updated May 2018, retrieved on Mar. 23, 2022, retrieved from URL <https://www.niddk.nih.gov/health-information/diabetes/overview/what-is-diabetes/prediabetes-insulin-resistance>, 6 pages.

National Library of Medicine [online], "Glucose Metabolism Disorders", 2011, retrieved Jan. 11, 2011, retrieved from URL <http://nlm.nih.gov/cgi/mesh/2011MB_cgi?mode=&term=Glucose+Metabolism+Disorders&field=entry>, 3 pages.

Nauck et al., "Gastric Inhibitory Polypeptide and Glucagon-Like Peptide-1 in the Pathogenesis of Type 2 Diabetes," Diabetes, 2004, 53(3):S190-196.

Nauck et al., "Incretins and Their Analogues as New Antidiabetic Drugs," Drug News Perspect, 2003, 16(7):413-422.

ndep.nih.gov [online], "Diabetes Prevention," May 26, 2009, retrieved Jul. 1, 2011, retrieved from URL <http://ndep.nih.gov/diabetes/prev/prevention.htm>, 7 pages.

Nesi et al., "New Difunctionalized 4-Nitroisoxazoles from a-Nitroacetophenone Oxime," Heterocycles, 1985, 23(6):1465-1469.

Nezasa et al., "Uptake of rosuvastatin by isolated rat hepatocytes: comparison with pravastatin," Xenobiotica, 2003, 33(4):379-388.

Nicewonger et al., "Microwave-assisted acylation of 7-amino-5-aryl-6-cyanopyrido[2,3-d] pyrimidines," Molecular Diversityy, 2003, 7(2-4):247-252.

Niementowski, J. Praktika Chem., [2] "Synthesen von Chinazolinverbindugen" (1895), 51, 564-572.

Nightingale et al., "Gastrointestinal hormones in short bowel syndrome. Peptide YY may be the 'colonic brake' to gastric emptying," Gut, 1996, 39:267-272.

Nishimura et al., "Adiponectin Prevents Cerebral Ischemic Injury Through Endothelial Nitric Oxide Synthase-Dependent Mechanisms," Circulation, 2008, 117:216-223.

Norman et al., "Structure—Activity Relationships of a Series of Pyrrolo[3,2-d] pyrimidine Derivatives and Related Compounds as Neuropeptide Y5 Receptor Antagonists," J Med Chem, 2000, 43(22):4288-4312.

Novinson et al., "Novel Heterocyclic Nitrofurfural Hydrazones. In vivo Antitrypanosomal Activity," J Med Chem, 1976, 19(4):512-516.

O'Brien et al., "Vascular cognitive impairment," The Lancet Neurology, Feb. 2003, 2:89-98.

Okada et al., "Peripherally Not Centrally Administered Peptide YY(PYY) Decreases High Fat Diet Intake," Endocrine Society, 1993, 520 B:180.

Oku et al., "Adiponectin deficiency suppresses ABCA1 expression and ApoA-I synthesis in the liver," FFBS Letters, 2007, 581:5029-5033.

Olesen, "The use of bioisosteric groups in lead optimization," Current Opinion in Drug Discovery & Development, 2001, 4(4):471-478.

(56) References Cited

OTHER PUBLICATIONS

Olsson et al., "Rosuvastatin: A Highly Effective New7 HMG-CoA Reductase Inhibitor," Cardiovascular Drug Reviews, 2002, 20(4): 303-328.
Olsson, "Statins: how far have we come? A review of rosuvastatin," International Journal of Clinical Practice, 2003, Supplement 137:15-25.
Ortiz et al., "A Novel Long-Acting Selective Neuropeptide Y2 Receptor Polyethylene Glycol-Conjugated Peptide Agonist Reduces Food Intake and Body Weight and Improves Glucose Metabolism in Rodents," JPET, 2007, 323:692-700.
Ouchi and Walsh. "Adiponectin as anti-inflammatory factor," Clinica Chimica Acta, 2007, 380:24-30.
Ouchi et al., "Novel Modulator for Endothelial Adhesion Molecules: Adipocyte-Derived Plasma Protein Adiponectin," Circulation, 1999, 100:2473-2476.
Overton et al., "GPR119 a Novel G Protein-coupled Receptor Target for the Treatment of Type 2 Diabetes and Obesity," Brit. J. Pharmacol., 2008, 153:576-581.
Overton et al., "Deorphanization of a G protein-coupled receptor for oleoylethanolamide and its use in the discovery of small-molecule hypophagic agents," Cell Metabolism, 2006, 3:167-175.
Oxford Online Dictionary, Definition of Prescription, 2017, 4pp.
Ozeki el al., "Studies on Antiallergy Agent. 1. Synthesis of 1,4-Dihydro-4-oxo-3--quinolinecarboxylic Acids" Yakugaku Zasshi, 1987, 107(2): 123-134.
Parker and Balasubramaniam, "Neuropeptide Y Y2 receptor in health and disease," British Journal of Pharmacology, 2008, 153:420-431.
Parlow et al., "Design, Synthesis, and Crystal Structure of Selective 2-Pyridone Tissue Factor VIIa Inhibitors," J Med Chem, 2003, 46(22):4696-4701.
Paulsen et al., "Darstellung von Bausteinen zur Synthese carbocyclischer furanose-analoga," Chemische Berichte, 1981, 114(1):346-358 (with English abstract).
Pearson, "Inflammatory bowel disease," Nursing Times, 2004, 100(9):86-90.
Peat et al., "Novel pyrazolopyrimidine derivatives as GSK-3 inhibitors", Bioorganic & Medicinal Chemistry Letters, 2004, 14:2121-2125.
Pederson, "The Impact of Obesity on the Pathogenesis of Non-Insulin-Dependent Diabetes Mellitus: A Review of Current Hypotheses," Diabetes/Metabolism Reviews., 1989, 5(6):495-509.
Pei et al., "Discovery and Structure-Activity Relationships of Piperidinone- and Piperidine-Constrained Phenethylamines as Novel, Potent, and Selective Dipeptidyl Peptidase IV Inhibitors." J Med Chem, 2007, 50:1983-1987.
Pelat et al., "Rosuvastatin Decreases Cavcolin-1 and Improves Nitric Oxide-Dependent Heart Rate and Blood Pressure Variability in Apolipoprotein E-/- Mice in Vivo," Circulation, 2003, 107(19): 2480-2486.
Perry et al., "Prospective study of risk factors for development of non-insulin dependent diabetes in middle aged British men," BMJ, 1995, 310:560-564.
Peters et al., "Aminomethylpyrimidines as novel DPP-IV inhibitors: A 105-fold activity increase by optimization of aromatic substituents," Bioorganic & Medicinal Chemistry Letters, 2004, 14:1491-1493.
Peterson et al., "Expanding the Scope of Crystal Form Evaluation in Pharmaceutical Science," J Pharm Pharmaceut Sci, 2006, 9(3):317-326.
Phillips et al., "Discovery of N-[2-[5-Amino(imino)methyl]-2-hydroxyphenoxyl]-3,5-difluoro-6-[3-(4,5-dihydro-1-methyl-1H-imidazol-2-yl)phenoxyl]pyridin-4-yl)-N-methylglycine(ZK-807834): A Potent, Selective, and Orally Active Inhibitor of the Blood Coagulation Enzyme Factor Xa1-," J Med Chem, 1998, 41(19):3557-3562.
Pittner et al., "Effects of PYY[3-36] in rodent models of diabetes and obesity," International Journal of Obesity, 2004, 28:963-971.

Pomorski, "Synthesis of Acids. Derivatives of 4-Hydroxy-1, 5-Naphthyridine," Roczniki Chemii Aim Soc Chun Polonorum, 1974, 48:321-325.
Potenza and Lerner, "A Rapid Quantitative Bioassay for Evaluating the Effects of Ligands Upon Receptors That Modulate cAMP Levels in a Melanophore Cell Line," Pigment Cell Research, 1992, 5(6):372-378.
Poupaert, "Drug Design: Basic Principles and Applications," Encyclopedia of Pharmaceutical Technology, 2007, 1362-1369 (James Swarbrick 3rd ed.).
Prasad et al.. "Convenient Methods for the Reduction of Amides. Nitriles, Carboxylic Esters, Acids and Hydroboration of Alkenes Using NaBH4/I2 System," Tetrahedron, 1992, 48(22):4623-4628.
Press et al., "Synthesis and SAR of 6-Substituted Purine Derivatives as Novel Selective Positive Inotropes," J Med Chem, 1992, 35(24):4509-4515.
prnewswire.com [online], "Arena Pharmaceuticals Reports Positive Long-Term Data from the Open-Label Extension of the Phase 2 OASIS Trial Evaluating Etrasimod for Treatment of Ulcerative Colitis," Jan. 2019, retrieved on Mar. 25, 2022, retrieved from URL <https://www.prnewswire.com/news-releases/arena-pharmaceuticals-reports-positive-long-term-data-from-the-open-label-extension-of-the-phase-2-oasis-trial-evaluating-etrasimod-for-treatment-of-ulcerative-colitis-300773493.html>, 2 pages.
Quesada et al., "2-Amino-5-nitro-4,6-dipiperidionpyrimidinium hydrogensulfate monohydrate: hydrogen-bonded sheets containing highly distorted cations," Acta Cryst, 2003. 59:102-104 (Abstract; 1 page).
Quintela et al., "6-Dimethylamino 1H-Pyrazolo[3,4-d]pyrimidine Derivatives as New Inhibitors of Inflammatory Mediators in Intact Cells," Bioorganic &Medicinal Chemistry (2003) 11:863-868.
Quintela et al., "Pyrazolopyrimidines: synthesis, effect on histamine release from rat peritoneal mast cells and cytotoxic activity," Eur J Med Chem (2001) 36:321-332.
Raffel et al., "Diabetes Mellitus," Principles and Practice of Medical Genetics, 1996, 1:1401-1440.
Raisz, "Pathogenesis of osteoporosis: concepts, conflicts, and prospects," J Clin Invest, 2005, 115(12):3318-3325.
Ram et al., "Chemotherapeutic agents: Part XXII—Synthesis of p-deficient pyrimidines as leishmanicides," Indian Journal of Chemistry, 1991, 30B (10):962-965.
Rao et al.. "Impaired Glucose Tolerance and Impaired Fasting Glucose," 1962, American Family Physician, 69(8): 1961-1968.
Rayasam et al., "Fatty acid receptors as new therapeutic targets for diabetes," Expert Opin Thera Targets, 2007, 11(5):661-671.
Reed and Scribner, "In-vivo and in-vitro models of type 2 diabetes in pharmaceutical drug discovery," Diabetes Obes Metab, 1999 1(2):75-86.
Rehwald and Gewald, "Syntheses of Thieno[2,3-d)Pyrimidines and Aminopyrimidines from 2-Alkoxy-5- Cyano-4-Thioxopyrimidine Intermediates," Heterocycles, 1998, 48(6):1157-1167.
Reinsich et al., "Adalimumab for induction of clinical remission in moderately to severely active ulcerative colitis: results of a randomised controlled trial," Gut, 2011, 60:780-787.
Remington's Pharmaceutical Sciences, 1985, Mack Publishing Company, 17:1418-1419, 5 pages.
Renshaw and Batterham, "Peptide YY: A Potential Therapy for Obesity." Current Drug Targets, 2005, 6:171-179.
Rewcastle et al., "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor," J Med Chem, 1996, 39:1823-1835.
Rimoin et al., "Emery and Rimoin's Principles and Practice of Medical Genetics", 1996. 3:1401-1402.
Roberts and Suschitzky, "Peroxy-acid Oxidation of NN-Disubstituted Aminotetrafluoro-, Amino-3- chlorotrifluoro-, and Amino-3,5-dichlorodifluoro-pyridines," Journal of the Chemical Society, 1969 11:1485-1491.
Roberts et al., "Polychloroaromatic compounds. Part I. Oxidation of pentachloropyridine and its NN-disubstituted amino-derivatives with peroxyacids." Journal of the Chemical Society (Section) C: Organic (1968) (12):1537-1541.

(56) References Cited

OTHER PUBLICATIONS

Roberts, "Two More Drugs for Dyslipidemia", American Journal of Cardiology, 2004 93:809-811.
Robev, "4-Cyclopropylamino- and 4-Cyclobutylaminoderivatives of some Arylsubstituted 5-Cyanopytimidines," Doktady Bolgarskoi Akademii Nauk, 1981 34(12):1677-1680.
Robins and Lin, "Potential Purine Antagonists. IV. Synthesis of Some 9-Methyl-6-substituted purines1," Dep of Chem, 1957, 79:490-494.
Rodriguez-Spong et al.. "General Principles of Pharmaceutical Solid Polymorphism: A Supramolecular Perspective", Adv Drug Delivery Rev, 2004, 56:241-274.
Rondinone, "Diabetes: the latest developments in inhibitors, insulin sensitisers, new drug targets and novel approaches" Expert Opin, 2005, 9(2):415-418.
Rosenson, "Rosuvastatin: a new inhibitor of HMG-CoA reductase for the treatment of dyslipidemia", Expert. Review of Cardiovascular Therapy, 2003, 1(4):495-505.
Rotwein el al., "Polymorphism in the 5' flanking region of the human insulin gene: a genetic marker for non-insulin-dependent diabetes," N Engl J Med, 1983, 308(2):65-71.
Ruggeri, "Platelets in atherothrombosis," Nat Med, 2002, 8(11):1227-1234.
Ruocco et al., "Pyoderma gangrenosum: an updated review," Eur. Acad. Dermatol & Venereology, 2009, 23:1008-1017.
Sage, Document regarding search, Feb. 2003, 1 page.
Sandborn et al., "Efficacy and Safety of Etrasimod in a Phase 2 Randomized Trial of Patients with Ulcerative Colitis," Gastroenterology, Feb. 2020, 158(3):550-561.
Sandborn et al., "UEG Week 2018 Oral Presentations OP242—'A Randomized Double-Blind Placebo-Controlled Trial of A Selective, Oral Sphingosine 1-Phosphate Receptor Modulator, Etrasimod (ADP334), In Moderate to Severe Ulverative Colitis: Results From the Oasis Study'" United European Gastroenterology Journal, 2018, 6:A94-A95.
Schafer et al., "Zur synthese von 4-aminochinolinen durch intramolekulare Friedel-Cfafts-Reaktion," Montash fur Chemie (1978) 109:527-535 (English Abstract).
Schuster, "Rosuvastatin—A Highly Effective New 3-hydroxy-3-methylglutaryl Coenzyme A Reductase Inhibitor: Review of clinical Trial Data at 10-40 mg doses in Dyslipidemic Patients" Cardiology, 99(3): 126-139 (2003).
Schwartz and Holst, "An Enteroendocrine Full Package Solution," Cell Metabolism, 2010, 11:445-447.
Scott et al., "Rosuvastatin: A Review oi Its Use in the Management of Dyslipidemia," American Journal of Cardiovascular Drugs, 4(2), 117-138 (2004).
Semple et al., "Discovery of a second generation of the orphan G-protein coupled receptor GPR119 with an improved profile," Bioorganic & Medicinal Chemistry Letters, 2012, 22:1750-1755.
Shah et al., "Current Approaches in the treatment of Alzheimer's disease." Biomedicine &Pharmacotherapy. 2008, 62:199-207.
Shah "GPR119 Agonists for the Potential Treatment of Type 2 Diabetes and Related Metabolic Disorders," Vitamins & Hormones, 2010, 84:415-448.
Shah "GPR119 agonists: A promising new approach for the treatment of type 2 diabetes and related metabolic disorders," Current Opin Drug Discov Develop., 2009. 12:519-532.
Shepherd et al., "Safety of Rosuvastatin," American Journal of Cardiology, 94(7):882-888 (2004).
Shibata et al., "Adiponectin protects against myocardial ischemia-reperfusion injury through AMPK- and COX-2-dependent mechanisms," Nat Med, 2005, 11:1096-1103.
Shibata et al., "Adiponectin protects against the development of systolic dysfunction following myocardial infarction," J. Mol. Cell Cardiol., 2007, 42:1065-1074.
Shibata et al., "Adiponectin Stimulates Angiogenesis in Response to Tissue Ischemia through Stimulation of AMP-activated Protein Kinase Signaling," J. Biol. Chem., 2004, 279:28670-28674.

Shore et al., "Adiponectin attenuates allergen-induced airway inflammation and hyperresponsiveness in mice," J. Allergy Clin. Immunol, 2006, 118:389-395.
Showell et al., "Tetrahydropyridvioxadiazoles: semirigid muscarinic ligands," J Med Chem (1991) 34(3):1086-1094.
Sigma-Aldrich, catalog entry for 2-amino-6-chloro-4-pyrimidinol hydrate (catalog No. 07460); 1 page; retrieval date Mar. 16, 2010.
Sigma-Aldrich, catalog entry for 2-amino-6-hydroxy-2-mercaptopyrimidine monohydrate (catalog No. A57406); 1 page; retrieval date Mar. 16, 2010.
Sigma-Aldrich, catalog entry for 4,5-diamino-6-hydroxy-2-mercaptopyrimidine hemisulfate salt hydrate (3 92464); 1 page; retrieval date Mar. 16, 2010.
Sigma-Aldrich, catalog entry for 4,6-diamino-2-mercaptopyrimidine hydrate (catalog No. 125830); 1 page; retrieval date Mar. 16, 2010.
Silhar et al., "Facile and Efficient Synthesis of 6-(Hydroxymetbyl)purines," Org. Lett. (2004) 6(19):3225-3228.
Silvestri et at, "Novel indolyl aryl sulfones active against HIV-1 carrying NNRTI resistance mutations: synthesis and SAR studies," J Med Chem (2003) 46(12):2482-2493.
Smith et al., "Effects of positive allosteric modulators of the GABAB receptor on cocaine self-administration in rats," Psychopharmacology (2004)173(1-2):105-111.
Smith et. al., "Clinical, molecular, and genetic characteristics of PAPA syndrome: a review," Current Genomics, 2010, Bentham Science Publ., 11:519-527.
Soga et al., "Lysophosphatidvicholine enhances glucose-dependent insulin secretion via an orphan G-protein-coupled receptor," Biochem Biophys Res Commun (2005) 326:744-751.
Spruce, Lyle W., "Document regarding search," 2004, 1 page.
Starosotnikov et al., "Synthesis of -substituted 1-aryl-4,6-dinitro-1H-indazoles based on picrylacetaldehyde and their behavior in nucleophilic substitution reactions," Russian Chemical Bulletin 2003, 52(8), 1782-1709.
Steensma et al., "A novel method for the synthesis of aryl sulfones," Tetrahedron Ltrs (2001) 42:2281-2283.
Stein. "Management of Dyslipidemia in the High-Risk Patient," American Heart Journal, 144(6):S43-S50 (2002).
Sternfeld et al., "Synthesis and serotonergic activity of 3-[2-pyrrolidin-1-yl)ethyl]indoles: potent agonists for the h5-HTID receptor with high selectivity over the h5-HTIB receptor," J. Med Chem, 1999, 28(6):761-769.
STN Search Report dated May 22, 2017, 9 pages (RN 380350-42-5, STN/CAPLUS (Year: 2002).
Strupczewski et al., "Synthesis and neuroleptic activity of 3-(1-substituted-4-piperidinyl)-1,2-benzisoxazoles," J Med Chem (1985) 28(6):761-769.
Suami et al., "Nucleoside analogs. I. Synthesis of 1,3-dihydroxy-2-(6-substitued-9-pudinyl)cyclohexane," Journal of Heterocyclic Chemistry (1969) 6(5):663-665.
Sugimoto et al., "Lithiation of 1H-Pyrazolo[3,4-d]pyrimidine Derivative Using Lithium Alkanetellurolate," Tetrahedron Letters (1999) 40:2139-2140.
Sugimoto et al., "Preparation of Nitrogen-Containing π-Deficient Heteroaromatic Grignard Reagents: Oxidative Magnesiation of Nitrogen-Containing n-Deficient Halgenoheteroaromatics Using Active Magnesium," J. Org. Chem. (2003) 68:2054-2057.
Summer et al., "Alveolar macrophage activation and an emphysema-like phenotype in adiponectin-deficient mice," Am J. Physiol. Lung Cell Mol. Physiol, 2008, 294:L1035-L1042.
Takei et al., "A New Synthetic Method for Some Pyrazolo[4,3-]pyrimidines1)," Bulletin of the Chemical Society of Japan, Aug. 23, 2005, 52(1):208-211.
Tao et al., "Adiponectin Cardioprotection After Myocardial Ischemia/Reperfusion Involves the Reduction of Oxidative/Nitrative Stress," Circulation, 2007, 115:1408-1416.
Tatemoto and Mutt, "Isolation of two novel candidate hormones using a chemical method for finding naturally occurring polypeptides," Nature, 1980, 285:417-418.
Terashima et al., "Inhibition of human 06-alkylguanine-DNA alkyltransferase and potentiation of the cytotoxicity of

(56) References Cited

OTHER PUBLICATIONS chloroethylnitrosourea by 4(6)-(benzyloxy)-2,6(4)-diamino-5-(nitro or nitroso)pyrimidine derivatives and analogues," J Med Chem (1998) 41(4):503-508.
The Diabetes Mall [online] "Syndrome X," Feb. 2002, retrieved on Sep. 24, 2014, retrieved from URL <https://www.diabetesnet.com/about-diabetes/types-diabetes/syndrome-x>, 1 page.
The Pocket Oxford American Dictionary of Current English, "Advise" and "Prescribe" Oxford University Press, New York: 2002, pp. 11 and 623.
Thompson et al., "N6.9-Disubstituted Adenines: Potent, Selective Antagonists at the A1 Adenosine Receptor," J. Med. Chem. (1991) 34:2877-2882.
Thompson et al., "Synthesis and evaluation of 6-(dibromomethyl)~5-nitropyrimidines as potential antitumor agents," J Med Chem (1997) 40(5):766-770.
Tilg and Moschen, "Adipocytokines: mediators linking adipose tissue, inflammation and immunity," Nat. Rev. Immunol., 2006, 2006, 6:772-783.
Trejo et al., "Design and Synthesis of 4-Azaindoles as Inhibitors of p38 MAP Kinase," J. Med. Chem., (2003) 46:4702-4713.
Tseng and Liu, "Peptide YY and cancer: current findings and potential clinical applications," Peptides, 2002, 23:389-395.
Tsukiyama et al., "Gastric Inhibitory Polypeptide as an Endogenous Factor Promoting New Bone Formation after Food Ingestion," Mol Endocrinol., 2006, 20:1644-1651.
Tuomilehto et al., "A Review of the Efficacy of Rosuvastatin in Patients with Type 2 Diabetes," International Journal of Clinical Practice, Supplement, 143, 30-40 (2004).
Turck et al., "Advances in the directed metallation of azines and diazines (pyridines, pyrimidines, pyrazines. pyridazines, quinolones, benzodiazines and carbolines). Part 2: Metallation of pyrimidines, pyrazines, pyridazines mid benzodiazines," Tetrahedron (2001) 57(21):4489-4505.
Ueno et al., "The role of PYY in feeding regulation," Regul Pept., 2008, 145:12-16.
Ulrich, "Crystallization," Kirk-Othmer Enclyclopedia of the Chemical Technology, 2002, Chapter 4, 8:95-147.
United States Pharmacopeial Convention, USP35 NF30, 2012: U.S. Pharmacopoeia National Formulary, Optical Microscopy, Physical Tests, 2012, 331-334.
University of Maryland Medical Center [online], "Familial hypercholesterolemia," 2011, retrieved on July 2, 2011, retrieved from URL <http://www.umm.edu/ency/article/00392prv.htm>, 4 pages.
Ural et al., "Treatment with Cervistatin in Primary Mixed Hyperlipidemia Induces Changes in Platelet Aggregation and Coagulation System Components," International Journal of Hematology, 76(3):279-283 (2002).
Urgaonkar et al., "Pd/P(i-BuNCH2CH2)3N: an efficient catalyst for Suzuki cross-coupling of aryl bromides and chlorides with arylboronic adds," Tetrahedron Letters (2002) 43(49):8921-8924.
Urwyler et al., "N,N'-Dicyclopentyl-2-methylsulfanyl-5-nitro-pyrimidine-4,6-diamine (GS39783) and Structurally Related Compounds: Novel Allosteric Enhancers of γ-Aminobutyric AcidB Receptor Function," Journal of Pharmacology and Experimental Therapeutics 2003, 307(1):322-330.
Vascular Web [online], "Hyperlipidemia," 2010, retrieved on Jan. 28, 2011, retrieved from URL http://www.vascularweb.org/patients/NorthPoint/Hyperlipidemia.html>, 5 pages.
Vaughan et al., "The Reformatsky Reaction. I. Zinc and Ethyl -60-Bromoisobutyrate," J. Org. Chem, Jun. 1965, 30:1790-1795.
Vice et al., "Concise Formation of 4-Benzyl Piperidines and Related Derivatives Using a Suzuki Protocol," J. Org. Chem. (2001) 66:2487-2492, Supporting Information, pp. S1-S32.
Vice et al., "Concise Formation of 4-Benzyl Piperidines and Related Derivatives Using a Suzuki Protocol," J. Org. Chem. (2001) 66:2487-2492.
Villhauer et al., "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties," J. Med. Chem., 2003, 46:2774-2789.
Villhauer et al., "1-[2-[(5-Cyanopyridin-2-yl)amino]-ethylamino]acetyl-2-(S)-pyrrolidine-carbonitrile: A Potent, Selective, and Orally Bioavailable Dipeptidyl Peptidase IV Inhibitor with Antihyperglycemic Properties," J. Med. Chem., 2002, 45:2362-2365.
Vinogradov et al., "Synthesis and reactions of 1-aryl-3-formyl-4,6-dinitro-1H-indazoles," Mendeleev Communications, 2002, (5), 198-200.
Vona-Davis and McFadden, "PYY and the pancreas: Inhibition of tumor growth and inflammation," Peptides, 2007, 28:334-338.
Wang et al., "Amino-substituted heterocycles as isosteres of trans-cinnamides: design and synthesis of heterocyclic biaryl sulfides as potent antagonists of LFA-1/ICAM-1 binding," Bioorganic & Medicinal Chemistry Letters, 15(1), 195-201 (2005)..
Wang et al., "Improving the Oral Efficacy of CNS Drag Candidates: Discovery of Highly Orally Efficacious Piperidinyl Piperidine M2 Muscarinic Receptor Antagonists," J Med Chem (2002). 45(25):5415-5418.
Weber et al., "Microbic Superinfection in Relapse of Inflammatory Bowel Disease," J Clin Gastroenterol., 1992, 14(4):302-308.
Webmd.com [online], "Type I Diabetes Prevention," retrieved on May 26, 2009. Retrieved from URL <http://diabetes.webmd.com/tc/type-1-diabetes-prevention>, 3 pages.
Wells et al., "Regioselective nucleophilic substitutions of fluorobenzene derivatives," Tetrahedron Letters, (1996) 37(36):6439-6442.
Werbel et al., "Synthesis and antimalarial effects of 5,6-dichloro-2-[(4-[[ [4-(diethylamino)1-methylbutyl]amino [[-6-methyl-2-pyrimidinyl)amino] benzimidazole and related benzimidazoles and 1,H-Imidazo[4,5-b] pyridines," J. Het. Chem (1973) vol. 10, 363-382.
West, Solid State Chemistry and its application, New York, 1988, pp. 358 & 365.
Wilson et al., "Microwave-assisted synthesis of 2-aminoquinolines," Tetrahedron Letters (2002) 43(4):581-583.
Winkelmann et al., "Haplotypes of the Cholesteryl Ester Transfer Protein Gene Predict Lipid-Modifying Response to Statin Therapy," Germany Pharmacogenomics Journal, 3(5): 284-296 (2003).
Woldbye et al., "Differential suppression of seizures via Y2 and Y5 neuropeptide Y receptors," Neurobiology of Disease, 2005, 20:760-772.
Wolfe et al., "Scope and limitations of the Pd/BINAP-catalyzed amination of aryl bromides," J Org Chem, 2000, 65(4):1144-1157.
Wolfe et al., "Simple, efficient catalyst system for the palladium-catalyzed amination of aryl chlorides, bromides, and triflates," J Org Chem, 2000, 65(4):1158-1174.
Wolter et al., "Copper-Catalyzed Coupling of Aryl Iodides with Aliphatic Alcohols," Organic Letters, 2002, 4(6):973-976.
Wolter et al., "Copper-Catalyzed Coupling of Aryl Iodides with Aliphatic Alcohols," Organic Letters, 2002, 4(6):973-976, Supporting Information, pp. S1-S16.
World Health Organization Technical Report Series 921, "Prevention and Management of Osteopoosis," 2003, 206 pages.
Wortley et al., "Peptide YY Regulates Bone Turnover in Rodents," Gastroenterol., 2007, 133:1534-1543.
Wu et al., "One-Pot Two-Step Microwave-Assisted Reaction in Constructing 4,5-Disubstituted Pyrazolopyrimidines," Org. Lett., (2003) 5(20):3587-3590.
Xia et al., "Discovery of a nortropanol derivative as a potent and orally active GPR119 agonist for type 2 diabetes," Bioorganic Med. Chem. Lett., 2011, 21:3290-3296.
Xie et al., "Glucose-dependent insulinotropic polypeptide receptor knockout mice have altered bone turnover," Bone, 2005 37:759-769.
Yamamoto et al., "Correlation of the adipocyte-derived protein adiponectin with insulin resistance index and serum high-density lipoprotein-cholesterol, independent of body mass index, in the Japanese population," Clinical Science, 2002, 103:137-142.
Yarovenko et al., "New method for the preparation of 5-amino-1,2,4-oxadiazoles," Bull Acad Sci, USSR Div Chem Sci, (1991) 40:1924.

(56) References Cited

OTHER PUBLICATIONS

Yokota et al., "Adiponectin, a new member of the family of soluble defense collagens, negatively regulates the growth of myelomonocytic progenitors and the functions of macrophages," Blood, 2000, 96:1723-1732.

Yoon et al., "Reaction of Diisobutylalummum Hydride with Selected Organic Compounds Containing Representative Functional Groups," J. Org. Chem., (1985) 50:2443-2450.

Yoshida et al., "AS1907417, a novel GPR119 agonist, as an insulinotropic and β-cell preservative agent for the treatment of type 2 diabetes," Biochemical and Biophysical Research Communications, 2010, 400:745-751.

Yuan et al., "3-Aryl pyrazolo[4,3-d]pyrimidine derivatives nonpeptide CRF-1 antagonists," Bioorganic Medicinal Chemistry Lett. (2002) 2133-2136.

Zamponi et al., "Unique structure-activity relationship for 4-isoxazolyl-1,4-dihydropyridines," J Med Chem (2003) 46:87-96.

Zamponi et al., "Unique structure-activity relationship for 4-isoxazolyl-1,4-dihydropyridines," J Med Chem (2003). Supporting Information., pp. 1-31.

Zander et al., "Effect of 6-week course of glucagon-like peptide 1 on glycaemic control, insulin sensitivity, and β-cell function in type 2 diabetes: a parallel-group study," Lancet, 2002, 359:824-830.

Zhang, et al., "Preparation of 1-(Tri-n-Butylstannyl) Furanoid Glycals and Their Use in Palladium-Mediated Coupling Reactions," Tetrahedron Letters (1993) 34(10):1571-1574.

Zhong et al., "Effects of glucose-dependent insulinotropic peptide on osteoclast function," Am J Physiol Endocrinol Metab, 2007, 292:E543-E548.

Zhu et al., "Synthesis and Mode of Action of 125I-and 3H-Labeled Thieno[2,3-c]pyridine Antagonists of Cell Adhesion Molecule Expression," J. Org. Chem., 2002, 67(3):943-948.

Zon and Peterson, "In vivo Drag Discovery in the Zebrafish," Nature Reviews, Jan. 2005, 4:35-44.

Cohen et al., "Long-term efficacy of fingolimod treatment in relapsing-remitting patients who did not respond to interferon treatment," Abstract of Poster, Presented at 32nd Congress of ECTRIMS, Sep. 14-17, 2016, London, United Kingdom, 2 pages.

Jenne et al., "T-bet-dependent S1P5 expression in NK cells promotes egress from lymph nodes and bone marrow," Journal of Experimental Medicine, 2009, 206(11):2469-2481.

Liu et al., "Conjugated bile acids promote cholangiocarcinoma cell invasive growth through activation of sphingosine 1-phosphate receptor 2," Hepatology, 2014, 60(3):908-918.

Sun et al., "Interleukin-33 Promotes Disease Progression in Patients with Primary Biliary Cirrhosis," The Tohoku Journal of Experimental Medicine, 2014, 234(4):255-261.

\* cited by examiner

Schedule of Procedures and Visits for Screening, Treatment, and Follow-Up Periods

| Evaluation | Screening | | | Treatment Period | | | | | | | | Follow Up |
|---|---|---|---|---|---|---|---|---|---|---|---|---|
| | Week -8 to -4 | Day -1 | - | Week 2 | Week 4 | Week 8 | Week 12 | Week 14[a] | Week 16 | Week 20 | Week 24 (EOT)/(EWD) | Week 26 (EOS) |
| | Days -60 to -28 | | Day 1 Baseline | Day 14±1 | Day 28±2 | Day 56±2 | Day 84±2 | Day 98±2 | Day 112±2 | Day 140±2 | Day 168±3 | Day 182±3 |

FIGURE 2

Schedule of Procedures and Visits for the Screening Period

| Evaluation | Screening | |
|---|---|---|
| | Week -8 to -4 | - |
| | Days -60 to -28 | Day -1 |
| Informed consent | x | |
| Medical history | x | |
| Demographics | x | |
| Inclusion/exclusion | x | |
| PBC-40/ 5-D pruritus | | x |
| Body mass index | x | |
| Body weight | x | |
| Physical exam and neurological exam | x | |
| 12-lead ECG[3] | x | |
| 24-hour Holter monitoring[3] | | x |
| Vital signs[3] | x | |
| Concomitant medication | x | x |
| Dispense study drug[5] | | |
| Virology screen (HIV, HBsAg, HCV) | x | |
| AE evaluation | x | x |
| PML assessment | x | |
| TB screening | x | |
| Ophthalmoscopy with OCT (if available) | x | |
| Ophthalmological exams including Schirmer and TBUT | x | |
| Pulmonary function test | x | |
| PK blood samples[2] | | |
| Chemistry including ALP (fasted >8 hours) | x | x |
| Complete blood count and lymphocyte subsets | x | x |
| Urinalysis | x | x |
| Fasting lipid panel | x | x |
| Urine drug screen | x | |
| Pregnancy test[4] | x | x |
| Total serum IgG and IgM, AMA and HsCRP | | x |
| Serum bile acids and C4 | | x |
| FSH[6] | x | |
| Coagulation | x | x |
| Fibroscan® | x | |
| TSH and free T3 and T4 | x | |

FIGURE 3

Schedule of Procedures and Visits for the Treatment Period (Part 1)

| Evaluation | - | Treatment Period | | | | | | | |
|---|---|---|---|---|---|---|---|---|---|
| | Day 1 Baseline | Week 2 Day 14±1 | Week 4 Day 28±2 | Week 8 Day 56±2 | Week 12 Day 84±2 | Week 14[a] Day 98±2 | Week 16 Day 112±2 | Week 20 Day 140±2 | Week 24 (EOT)/(EWD) Day 168±3 |
| Informed consent | x | | | | | | | | |
| Medical history | x | | | | | | | | |
| Demographics | x | | | | | | | | |
| Inclusion/exclusion | x | | | | | | | | |
| PBC-40/ 5-D pruritus | x | x | x | x | | | x | x | x |
| Body mass index | | | | | | | | | x |
| Body weight | | | | | | | | | x |
| Physical exam and neurological exam | x[1] | x[1] | x[1] | x[1] | x[1] | x[a,1] | x[1] | x[1] | x |
| 12-lead ECG[3] | x | x | x | x | x | x[a] | x | x | x |
| 24-hour Holter monitoring[3] | x | | | | x[a] | | | | |
| Vital signs[3] | x | x | x | x | x | x[a] | x | x | x |
| Concomitant medication | x | x | x | x | x | x[a] | x | x | x |
| Dispense study drug[5] | x | x | x | x | x | x[a] | x | x | |
| Virology screen (HIV, HBsAg, HCV) | | | | | | | | | |
| AE evaluation | x | x | x | x | x | x[a] | x | x | x |
| PML assessment | x | x | x | x | x | x[a] | x | x | x |
| TB screening | | | | | | | | | |

FIGURE 4

Schedule of Procedures and Visits for the Treatment Period (Part 2)

| Evaluation | - | Treatment Period | | | | | | | | |
|---|---|---|---|---|---|---|---|---|---|---|
| | Day 1 Baseline | Week 2 Day 14±1 | Week 4 Day 28±2 | Week 8 Day 56±2 | Week 12 Day 84±2 | Week 14[a] Day 98±2 | Week 16 Day 112±2 | Week 20 Day 140±2 | Week 24 (EOT)/(EWD) Day 168±3 |
| Ophthalmoscopy with OCT (if available) | | | | | x | | | | x |
| Ophthalmological exams including Schirmer and TBUT | | | | | x[7] | | | | x[7] |
| Pulmonary function test | | | | | | | | | x |
| PK blood samples[2] | x | x | | | x | x[a] | | | x |
| Chemistry including ALP (fasted >8 hours) | x | x | x | x | x | x[a] | x | x | x |
| Complete blood count and lymphocyte subsets | x | x | x | x | x | x[a] | x | x | x |
| Urinalysis | x | x | x | x | x | | x | x | x |
| Fasting lipid panel | x | | x | | x | x[a] | | | x |
| Urine drug screen | | | | | | | | | |
| Pregnancy test[4] | x | | x | x | x | | x | x | x |
| Total serum IgG and IgM, AMA and HsCRP | x | | | | x | | | | x |
| Serum bile acids and C4 | x | | | | x | | | | x |
| FSH[6] | | | | | | | | | |
| Coagulation | x | | | | x | | x | | x |
| Fibroscan® | | | | | | | | | x |
| TSH and free T3 and T4 | | | | | | | | | |

FIGURE 5

Schedule of Procedures and Visits for the Follow-Up Period

| Evaluation | Follow Up Week 26 (EOS) Day 182±3 |
|---|---|
| Informed consent | |
| Medical history | |
| Demographics | |
| Inclusion/exclusion | |
| PBC-40/ 5-D pruritus | x |
| Body mass index | x |
| Body weight | x |
| Physical exam and neurological exam | x |
| 12-lead ECG[3] | |
| 24-hour Holter monitoring[3] | |
| Vital signs[3] | x |
| Concomitant medication | x |
| Dispense study drug[5] | |
| Virology screen (HIV, HBsAg, HCV) | |
| AE evaluation | x |
| PML assessment | |
| TB screening | |
| Ophthalmoscopy with OCT (if available) | |
| Ophthalmological exams including Schirmer and TBUT | |
| Pulmonary function test | |
| PK blood samples[2] | |
| Chemistry including ALP (fasted >8 hours) | x |
| Complete blood count and lymphocyte subsets | x[8] |
| Urinalysis | |
| Fasting lipid panel | |
| Urine drug screen | |
| Pregnancy test (serum)[4] | |
| Total serum IgG and IgM, AMA and HsCRP | x |
| Serum bile acids and C4 | |
| FSH[6] | |
| Coagulation | |
| Fibroscan® | |
| TSH and free T3 and T4 | |

FIGURE 6

COMPOUNDS AND METHODS FOR TREATMENT OF PRIMARY BILIARY CHOLANGITIS

FIELD OF THE INVENTION

The present invention relates to, inter alia, methods of treatment and combinations of (R)-2-(7-(4-cyclopentyl-3-(trifluoromethyl)benzyloxy)-1,2,3,4-tetrahydrocyclopenta[b]indol-3-yl)acetic acid (Compound 1) useful for the treatment of primary biliary cholangitis (PBC). In some embodiments, the methods further comprise administering Compound 1, or a pharmaceutically salt, solvate, or hydrate thereof, in combination with a compound selected from the group consisting of: an antihistamine (diphenhydramine), cholestyramine (questran, prevalite), rifampin, an opioid antagonist (naloxone), pilocarpine (isopto carpine, salagen), cevimeline (evoxac), calcium and/or vitamin D supplement, and vitamin A, D, E and/or K supplement. Other embodiments relate to titration packages for enabling compliance with a regimen of changing dosage of a medication over a period of time for the treatment of primary biliary cholangitis (PBC).

BACKGROUND OF THE INVENTION

The sphingosine-1-phosphate (S1P) receptors 1-5 constitute a family of G protein-coupled receptors with a seven-transmembrane domain. These receptors, referred to as $S1P_1$ to $S1P_5$ (formerly termed endothelial differentiation gene (EDG) receptor-1, -5, -3, -6, and -8, respectively; Chun et al., Pharmacological Reviews, 54:265-269, 2002), are activated via binding by sphingosine-1-phosphate, which is produced by the sphingosine kinase-catalyzed phosphorylation of sphingosine. $S1P_1$, $S1P_4$, and $S1P_5$ receptors activate Gi but not Gq, whereas $S1P_2$ and $S1P_3$ receptors activate both Gi and Gq. The $S1P_3$ receptor, but not the $S1P_1$ receptor, responds to an agonist with an increase in intracellular calcium.

The compound (R)-2-(7-(4-cyclopentyl-3-(trifluoromethyl)benzyloxy)-1,2,3,4-tetrahydrocyclopenta[b]indol-3-yl)acetic acid (Compound 1) is a potent ($EC_{50}$ cAMP, 0.093 nM (human)) and selective ($EC_{50}$ β-arrestin, 6.10 nM ($S1P_1$), >10,000 nM ($S1P_2$), >10,000 nM, ($S1P_3$), 147 nM ($S1P_4$), and 24.4 nM ($S1P_5$)), orally available investigational drug candidate for the $S1P_1$ receptor.

In preclinical studies, Compound 1 showed calculated lymphocyte lowering $IC_{50}$ values in four different species: 0.101 µM (mouse), 0.051 µM (rat), 0.058 µM (dog), and 0.098 µM (monkey). Notably, the calculated lymphocyte lowering $IC_{50}$ values reflect total plasma concentration wherein Compound 1 is highly protein bound (97.8% human, 98.0% rat). Compound 1 was shown to be efficacious in the murine experimental autoimmune encephalomyelitis (EAE) model that mimics multiple sclerosis. Prophylactically, Compound 1 prevented the onset and severity of disease relative to vehicle up to day 25, at which time dosing was discontinued. All treatment arms went on to develop severe disease. Therapeutic administration of Compound 1 was also examined. Treatment began at day 18, by which time all animals had developed severe disease. Compound 1 was administered from day 18 to day 37 and showed to reverse the disease relative to vehicle and was similar to the efficacy observed with fingolimod (i.e., GILE-NYA® was approved in September 2010 for the treatment of individuals with relapsing forms of multiple sclerosis). Similarly, Compound 1 was efficacious in a collagen induced arthritis (CIA) model. Prophylactic oral administration in female Lewis rats resulted in a significant reduction in ankle diameters on day 17 following a daily oral dose and was similar to that observed in rats treated with fingolimod or methotrexate. Improvement in histological parameters in the knees and ankles of CIA rats was also observed, suggesting that inhibiting lymphocyte entry into arthritic joints with Compound 1 treatment suppresses CIA in rodents. Additional details can be found in the following, PCT application, serial number PCT/US2009/004265, filed 22 Jul. 2009 (International Publication Number WO2010/011316); PCT application, serial number PCT/US2011/000153, filed 27 Jan. 2011 (International Publication Number WO2011/094008); and Buzard: D. J., et al., *ACS Med. Chem. Lett.* 2014, 5, 1313-1317; each hereby incorporated by reference in its entirety.

S1P is a signaling sphingolipid required by lymphocytes to exit the lymphoid tissue and enter the bloodstream via a chemotactic gradient. The S1P1 receptor is a physiological mediator which has been shown to regulate lymphocyte recirculation between lymphoid tissue and blood. Binding and internalization of the S1P1 receptor may result in lymphocyte retention within lymphoid tissue, with subsequent reduction in peripheral lymphocyte count and lymphocyte availability for recruitment to sites of inflammation. S1P1 receptor surface expression is required for S1P gradient-mediated lymphocyte migration out of lymphoid tissue into the circulation (Brinkmann V., *Nat Rev Drug Discov* 2010 November; 9(11):883-97).

Primary biliary cholangitis is a chronic cholestatic liver disease of unknown cause. Progressive bile-duct injury from portal and periportal inflammation may result in progressive fibrosis and eventual cirrhosis. Immunohistochemical staining of T lymphocytes in portal and periportal areas in PBC patients shows CD4-positive and CD8-positive T cells (T-cell populations known to be modulated by S1P1 interaction). In addition to T cells, natural killer cells also appear to play a role in PBC. Resting as well as activated NK cells express S1P1, S1P4, and S1P5 receptors. The S1P5 receptor has been reported to be involved in chemotaxis of NK cells (Jenne et al 2009). Allende et al. demonstrated a role for S1P4 in neutrophil trafficking in that S1P lyase deficient mice (Sgpl1−/−GrS1pr1) did not significantly differ from the single mutant Sgpl1−/− mice in blood levels of lymphocytes and neutrophils and in serum concentrations of pro-inflammatory cytokines). In contrast, mice that lacked both S1P lyase and S1P4 (Sgpl1−/−S1pr4−/−) had significantly lower blood neutrophil counts and serum pro-inflammatory cytokines than the single-mutant Sgpl1−/− mice (Allende et al. 2011). These data suggest involvement of the S1P4 receptor in neutrophil trafficking, which may be relevant given reports suggesting a role for IL-33 in enhancing the migration of neutrophils in the progression PBC (Sun et al. 2014). Avoidance of S1P2 interaction is important due to the reported links between S1P2 modulation in cholangiocarcinoma (CCA), possibly driven by conjugated bile acid modulation of the S1P2 receptor on cholangiocytes (Liu et al 2014). Inhibition of S1P1, but not S1P2 receptors, has been shown to reduce bile salt (glycochenodeoxycholic acid)-induced apoptosis in rat hepatocytes, indicating potential therapeutic benefits in PBC (Karimian et al., *Biochim Biophys Acta.* 2013 December; 1832(12):1922-9). Further, it has been reported that S1P1 may be involved in processes promoting liver fibrosis, suggesting that blockade of the S1P1 pathway may help attenuate liver fibrosis (Yang L et al., *J Hepatol.* 2013 July; 59(1):114-23). Modulation of the S1P1, S1P4, and S1P5 receptors therefore represents a target profile for treating PBC.

However, many of the S1P modulators that are currently on the market or in clinical development have reportedly shown evidence of elevating liver transaminases upon chronic administration. For example, liver enzyme elevation has been seen for GILENYA (fingolimod), siponimod, ponesimod, GSK2018682, and ozanimod (Gergely et al., *British J of Pharm* 2012; 167:1035-1047; D'Ambrosio et al., *Therapeutic Advances in Chronic Disease* 2016; 7(1):18-33; Cohen et al., 32$^{nd}$ *Congress of ECTRIMS* 2016 Sep. 14-17; Xu et al., *Am College of Clinical Pharm* 2014; 3(3):170-178). In fact, the product label for GILENYA (fingolimod) contain warnings and precautions about hepatic effects. Further, there is pathophysiological evidence of a reduction in drug metabolizing enzyme activities in patients with PBC, along with general liver impairment effects (as evidenced by elevated liver transaminases) (Reshetnyak, *World J of Gastroenterology* 2015 Jul. 7; 21(25):7683-7708). As such, the safety of a S1P modulator in a patient population with impaired liver function is unknown.

Described herein is a proof-of-concept clinical trial in which Compound 1 was evaluated in patients with PBC. Compound 1 shows an overall selective activation of S1P1, S1P4, and S1P5 and the potential for safe administration to individuals with liver impairment, and thus represents a much needed option for the treatment of individuals with PBC.

SUMMARY OF THE INVENTION

In its various embodiments, the present invention is directed to, inter alia, methods of treating primary biliary cholangitis (PBC) in an individual in need thereof comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof. In some embodiments, primary biliary cholangitis (PBC) is primary biliary cirrhosis.

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of primary biliary cholangitis (PBC).

In some embodiments, the individual was previously treated with a therapeutically effective amount of ursodeoxycholic acid (UDCA).

In some embodiments, the individual is currently treated with a therapeutically effective amount of ursodeoxycholic acid (UDCA).

In some embodiments, the therapeutically effective amount of UDCA is substantially the same amount (stable dose) for at least 6 months.

In some embodiments, the therapeutically effective amount of UDCA is substantially the same amount (stable dose) for at least 3 months.

In some embodiments, the individual was previously treated with ursodeoxycholic acid (UDCA) and the individual had an inadequate response to UDCA.

In some embodiments, the individual had an inadequate response to UDCA as determined by an alkaline phosphate (ALP)>1.67× upper limit of normal (ULN) for the individual.

In some embodiments, the individual had an inadequate response after 6 months of treatment with UDCA.

In some embodiments, the individual had an inadequate response after 6 months of treatment with UDCA and an alkaline phosphate (ALP)>1.67× upper limit of normal (ULN).

In some embodiments, the treatment dose of UDCA was at least 13 mg/kg/day.

In some embodiments, the individual has at least one primary biliary cholangitis diagnosis criteria selected from the group consisting of:
  anti-mitochondrial antibody (AMA) titer >1:40;
  alkaline phosphate (ALP)>1.5×ULN for at least 6 months; and
  liver biopsy findings consistent with PBC.

In some embodiments, the individual has at least two primary biliary cholangitis diagnosis criteria selected from the group consisting of:
  anti-mitochondrial antibody (AMA) titer >1:40;
  alkaline phosphate (ALP)>1.5×ULN for at least 6 months; and
  liver biopsy findings consistent with PBC.

In some embodiments, the individual has at least one of the criteria selected from the group consisting of:
  ALP>1.67×ULN but <10×ULN;
  ALT and AST<5×ULN;
  total bilirubin <1.5×ULN;
  international normalized ratio (INR)<1.2×ULN; and
  serum creatinine <1.5 mg/dL (133 µmol/L).

In some embodiments, the individual has at least one of the criteria selected from the group consisting of:
  ALP>1.67×ULN but <10×ULN;
  ALT and AST<5×ULN;
  total bilirubin <ULN;
  international normalized ratio (INR)<1.2×ULN; and
  serum creatinine <1.5 mg/dL (133 µmol/L).

In some embodiments, the individual has at least one additional condition selected from the group consisting of: pruritus, fatigue, osteoporosis, vitamin deficiencies, dry eyes and/or mouth, portal hypertension, and pain.

In some embodiments, the therapeutically effective amount of Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration.

In some embodiments, the individual is administered a titration dose of Compound 1 prior to the administering the therapeutically effective amount of Compound 1, wherein the titration dose is less than the therapeutically effective amount of Compound 1.

In some embodiments, the titration dose is less than about 2 mg of Compound 1.

In some embodiments, the titration dose is maintained until there are no significant changes in vital signs and/or EKG of the individual.

In some embodiments, the titration dose is maintained until the pulse rate ≥55 bpm, systolic blood pressure (SBP) ≥90, and diastolic blood pressure (DBP)≥55 mmHg in the individual.

In some embodiments, the titration dose is maintained for no more than 14 days prior to administering the therapeutically effective amount of Compound 1.

In some embodiments, the titration dose comprises a first titration dose and a second titration dose, wherein the first titration dose is less than the second titration dose and each titration dose is less than the therapeutically effective amount of Compound 1.

In some embodiments, the first titration dose is in an amount equivalent to about 1 mg of Compound 1.

In some embodiments, the second titration dose is in an amount equivalent to about 1.5 mg of Compound 1.

In some embodiments, the first titration dose is in an amount equivalent to about 1 mg of Compound 1 and the second titration dose is in an amount equivalent to about 1.5 mg of Compound 1.

In some embodiments, the first titration dose is maintained for no more than 7 days prior to administering the second titration dose.

In some embodiments, the second titration dose is maintained for no more than 7 days prior to administering the therapeutically effective amount of Compound 1.

In some embodiments, the therapeutically effective amount of Compound 1, or a pharmaceutically acceptable salt, hydrate, or solvate thereof, is in an amount equivalent to about 1.0 mg to about 5 mg of Compound 1.

In some embodiments, the therapeutically effective amount of Compound 1, or a pharmaceutically acceptable salt, hydrate, or solvate thereof, is in an amount equivalent to about 2 mg of Compound 1.

In some embodiments, the Compound 1, or a pharmaceutically acceptable salt, hydrate, or solvate thereof, is selected from: Compound 1, a calcium salt of Compound 1, and an L-arginine salt of Compound 1.

In some embodiments, the Compound 1, or a pharmaceutically acceptable salt, hydrate, or solvate thereof, is an L-arginine salt of Compound 1.

In some embodiments, the Compound 1, or a pharmaceutically acceptable salt, hydrate, or solvate thereof, is an anhydrous, non-solvated crystalline form of the L-arginine salt of Compound 1.

In some embodiments, the Compound 1, or a pharmaceutically acceptable salt, hydrate, or solvate thereof, is a crystalline free-plate habit of the non-solvated L-arginine salt of Compound 1.

In some embodiments, the Compound 1, or a pharmaceutically acceptable salt, hydrate, or solvate thereof, is an anhydrous, non-solvated crystalline form of Compound 1.

In some embodiments, the method further comprises administering Compound 1, or a pharmaceutically salt, solvate, or hydrate thereof, in combination with a therapeutically effective amount of with a compound selected from the group consisting of: an antihistamine (diphenhydramine), cholestyramine (questran, prevalite), rifampin, an opioid antagonist (naloxone), pilocarpine (isopto carpine, salagen), cevimeline (evoxac), calcium and/or vitamin D supplement, and vitamin A, D, E and/or K supplement.

Some embodiments of the present invention related to titration packages for enabling compliance with a regimen of changing dosage of a medication over a period of time for the treatment of primary biliary cholangitis (PBC), wherein the medication is (R)-2-(7-(4-cyclopentyl-3-(trifluoromethyl)benzyloxy)-1,2,3,4-tetrahydrocyclo-penta[b]indol-3-yl)acetic acid (Compound 1) or a pharmaceutically salt, solvate, or hydrate thereof, the package comprising:

a first number of daily units of a pharmaceutical composition comprising one or more doses of Compound 1, or a pharmaceutically acceptable salt, hydrate, or solvate thereof, wherein each dose is in an amount equivalent to about 1.5 mg or less of Compound 1, and a second number of daily units of a pharmaceutical composition comprising a standard dose of Compound 1, or a pharmaceutically acceptable salt, hydrate, or solvate thereof, is in an amount equivalent to about 1.0 to about 2.5 mg of Compound 1.

In some embodiments, the dose of the first number of daily units is in an amount equivalent to about 1 mg of Compound 1.

In some embodiments, the dose of the first number of daily units is in an amount equivalent to about 1.5 mg of Compound 1.

In some embodiments, the dose of the second number of daily units is in an amount equivalent to about 2 mg of Compound 1.

In some embodiments, the dose of the first number of daily units is in an amount equivalent to about 1 mg or 1.5 mg of Compound 1 and the dose of the second number of daily units is in an amount equivalent to about 2 mg of Compound 1.

Some embodiments relate to kits comprising a titration package according to any previous embodiment, and instructions indicating that the medication is to be administered to an individual in need of treatment of primary biliary cholangitis (PBC).

These and other aspects of the invention disclosed herein will be set forth in greater detail as the patent disclosure proceeds.

BRIEF DESCRIPTION OF THE DRAWINGS

FIG. 2 shows a schedule of procedures and visits for screening, treatment, and follow-up periods for individuals related to the clinical study described in Example 2.

FIG. 3 shows a schedule of procedures and visits for the screening period for individuals related to the clinical study described in Example 2.

FIG. 4 shows a schedule of procedures and visits for the treatment period (Part 1) for individuals related to the clinical study described in Example 2.

FIG. 5 shows a schedule of procedures and visits for the treatment period (Part 2) for individuals related to the clinical study described in Example 2.

FIG. 6 shows a schedule of procedures and visits for the follow-up period for individuals related to the clinical study described in Example 2.

Figure 1:
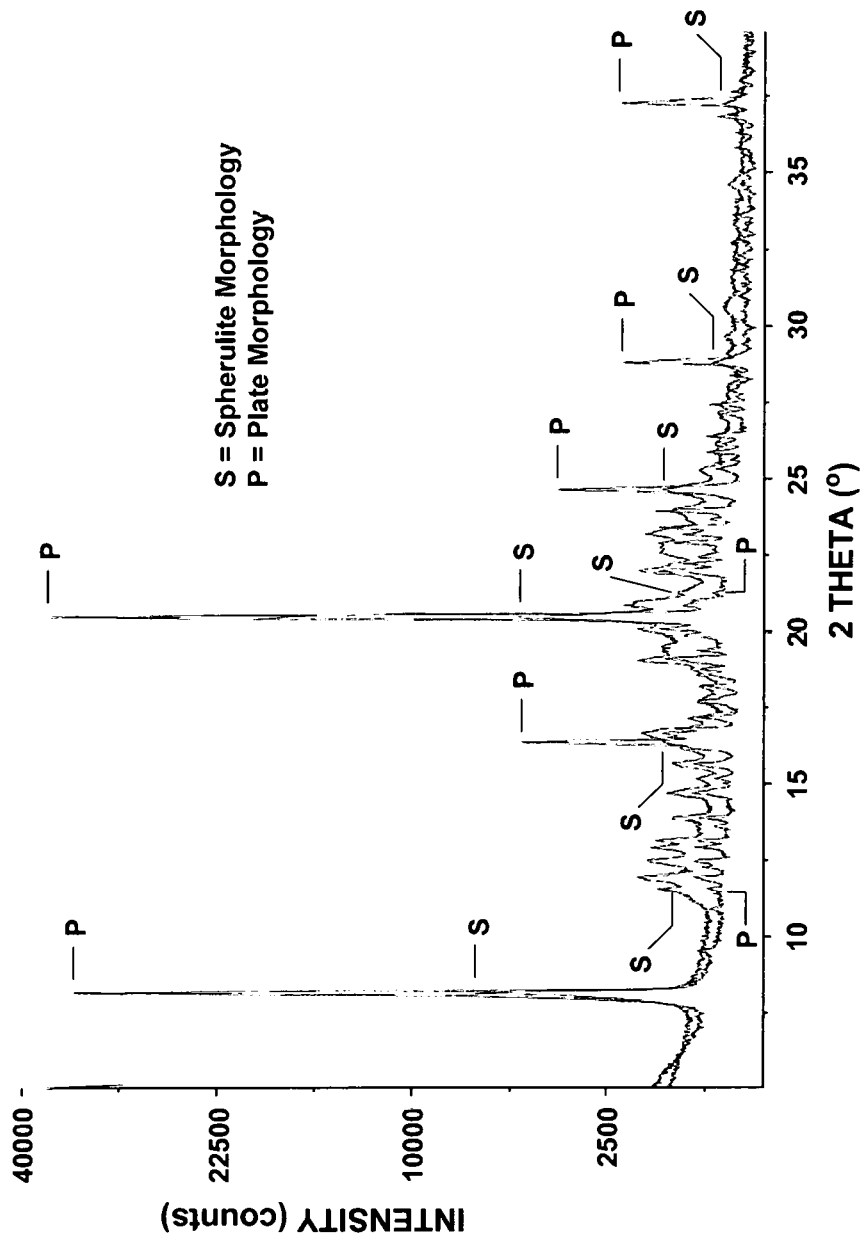
FIG. 1 shows a PXRD Pattern overlay for the L-arginine salt of Compound 1 showing the peak intensity differences between plates and spherulites indicating a higher degree of crystallinity for the plates compared to the spherulites. Also shown is the lower sample-related background scatter (i.e., a lower amorphous halo contribution) for the plates. However, the plates and spherulites are observed to show the same crystal phase.

Footnotes and abbreviations found in FIGS. 2 to 6 are provided below:

AE: adverse event; ALP: alkaline phosphatase; C4: 7 alpha-hydroxy-4-cholesten-3-one; ECG: electrocardiogram; EOS: end of study; EOT: end of treatment; EWD: early withdrawal; FU: follow up; HBsAg: hepatitis B surface antigen; HCV: hepatitis C virus; HIV: human immunodeficiency virus; PK: pharmacokinetics; PML: progressive multifocal leukoencephalopathy; pSS: primary Sjögren's syndrome; TB: tuberculosis.

*a* For patients with dose escalation who tolerate the 1 mg dose level based on available PK from Day 1 and Week 2, and safety data; Week 14 visit will only take place for these dose-escalated patients.

[1] Interim/abbreviated physical exam only.

[2] Blood samples for PK will be collected at up to 45 min pre-dose, and at 2, 4, 6, and 8 hours post-dose for Day 1 and Week 2, and optionally at 12 and/or 24 hours post-dose at Week 2. Week 12: If a patient does not dose escalate, a pre-dose sample will be taken. If a patient dose escalates to 2 mg daily dose, a pre-dose, 6- and 8-hour post-dose sample will be collected. Week 14: If a patient is on a 2 mg daily dose a pre-dose and 2, 4, 6, 8, and optional 12 and/or 24 hour post-dose sample will be collected. Week 24: all patients will have a PK sample collected approximately 24 hours after their last dose during the Week 24 visit with 2 optional timepoints between 72 hours and 1 week after their last dose. Day 1 and Week 2 data will provide guidance for potential dose escalation of etrasimod at week 12.

[3] Vital signs and 12-lead ECG will be captured hourly on Day 1/baseline and Week 2 pre-dose through at least 8 hours post-dose at the clinic. On Week 12 and Week 14, for those patients with dose escalation, vital signs and ECG monitoring will be performed hourly until at least 8 hours post dosing at the clinic. On Week 12, for those patients without dose escalation, ECG monitoring will be performed predose. For the rest of clinical visits (Weeks 4, 8, 16, 20, and 24), vital signs and 12-lead ECG will be captured at pre-dose. 24-hour Holter monitor will be performed 24 hours before dosing and through 24 hours post dosing on Day 1 and at Week 12 (if dose escalation occurred). Typically, all safety ECGs will be obtained as single tracings, with the exception of the pretreatment ECG obtained on Day 1, which is a triplicate recording.

[4] For all female patients, a urine dipstick pregnancy test is required at Day 1 and a serum hCG test is required for all other indicated visits.

[5] For the first 12 weeks of dose titration, individual patients will receive 1 mg q.d. if tolerable, followed by 2 mg q.d. at Week 12. During the rest of the study, dosage should be maintained at 2 mg q.d.

[6] FSH—only in women to confirm the postmenopausal status.

[7] For patients with abnormal results at screening.

[8] If the absolute peripheral lymphocyte count has not recovered to at least 80% of the baseline value, or reached normal ranges, at the 2-week follow-up, the patient must return for weekly CBC tests until the absolute peripheral lymphocyte count has returned to at least these values. AE: adverse event; ALP: alkaline phosphatase; C4: 7 alpha-hydroxy-4-cholesten-3-one; ECG: electrocardiogram; EOS: end of study; EOT: end of treatment; EWD: early withdrawal; FU: Follow up; HBsAg: hepatitis B surface antigen; HCV: hepatitis C virus; HIV: human immunodeficiency virus; PK: pharmacokinetics; PML: progressive multifocal leukoencephalopathy; pSS: primary Sjögren's syndrome; TB: tuberculosis.

DETAILED DESCRIPTION OF THE INVENTION

The present disclosure provides, inter alia, methods of treating primary biliary cholangitis (PBC) in an individual in need thereof comprising administering a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof.

Compound 1

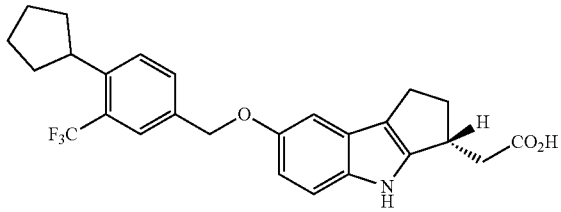

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of primary biliary cholangitis (PBC) in an individual.

In other embodiments, the present invention is directed to (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in the treatment of primary biliary cholangitis (PBC).

In other embodiments, the present invention is directed to titration packages for enabling compliance with a regimen of changing dosage of a medication over a period of time for the treatment of primary biliary cholangitis (PBC), wherein the medication is (R)-2-(7-(4-cyclopentyl-3-(trifluoromethyl)benzyloxy)-1,2,3,4-tetrahydrocyclo-penta[b]indol-3-yl)acetic acid (Compound 1) or a pharmaceutically salt, solvate, or hydrate thereof, the package comprising:

a first number of daily units of a pharmaceutical composition comprising one or more doses of Compound 1, or a pharmaceutically acceptable salt, hydrate, or solvate thereof, wherein each dose is in an amount equivalent to about 1.5 mg or less of Compound 1, and a second number of daily units of a pharmaceutical composition comprising a standard dose of Compound 1, or a pharmaceutically acceptable salt, hydrate, or solvate thereof, is in an amount equivalent to about 1.0 to about 2.5 mg of Compound 1.

Certain processes for the preparation of Compound 1 and the L-arginine salt of Compound 1 have been previously described; see WO2010/011316 and WO2011/094008. In addition, the novel crystalline plate habit for the L-arginine salt of Compound 1 has been previously described and is referred to herein as, "crystalline free-plate habit of the non-solvated L-arginine salt of Compound 1"; see WO2016/209809.

In some embodiments, the methods provided herein are for the treatment of primary biliary cholangitis that has progressed to primary biliary cirrhosis. In some embodiments, the methods provided herein are for the prevention of primary biliary cirrhosis. In some embodiments, the methods provided herein are for delayed progression to primary biliary cirrhosis.

The following is a list of abbreviations: ACS (acute coronary syndrome); ADL (activities of daily living); AE (adverse event); ALP (alkaline phosphatase); ALT (alanine aminotransferase (SGPT)); AMA (anti-mitochondrial antibodies); ANA (anti-nuclear antibodies); AST (aspartate aminotransferase (SGOT)); AV (atrio-ventricular); bpm (beats per minute); CBC (complete blood count); CFR (Code of Federal Regulations); CI (confidence interval); CRF (case report form); CRP (C-reactive protein); CRO (contract research organization); D (day); DILI (drug-induced liver injury); ECG (electrocardiogram); ED50 (half maximal dose); eGFR (estimated glomerular filtration rate); ELISA (enzyme-linked immunosorbent assay); EOS (end of study); EOT (end of treatment); FDA (Food and Drug Administration); FEV1 (forced expiratory volume); FU (follow up); FVC (forced vital capacity); GCP (Good Clinical Practice); GGT (gamma glutamyl transferase); HBsAg (hepatitis B surface antigen); hCG (human chorionic gonadotropin); HCV (hepatitis C virus); HREC (human research ethics committee (AUS)); HIV (human immunodeficiency virus); HR (heart rate); ICH (International Conference on Harmonization); ICF (informed consent form); IEC (Independent Ethics Committee); IND (Investigational New Drug); IRB (Institutional Review Board); INR (international normalized ratio); hormone-releasing system); IUD (intrauterine device); IUS (Intrauterine hormone-releasing system); kg (kilogram); LDH (lactate dehydrogenase); L (liter); MCH (mean corpuscular hemoglobin); MCV (mean corpuscular volume); MedDRA (Medical Dictionary for Regulatory Activities); mg (milligram); MI (myocardial infarction); NK (natural killer); NOAEL (no observed adverse effect level); OTC (over-the-counter); PBC (peripheral biliary cholangitis); PBL (peripheral blood lymphocyte); PD (pharmacodynamics); PFT (pulmonary function test); PGA (Physicians Global Assessments); PI (Principal Investigator); PK (pharmacokinetics); p.o. (per os (orally)); PRO (patient reported outcome); pSS (primary Sjögren's syndrome); PVG (pharmacovigilance); q.d. (quaque die (once daily)); SAP (statistical analysis plan); S1P (sphingosine 1-phosphate); SAE (serious adverse event); SBP (systolic blood pressure); SD (standard deviation); sec (second); SOP(s) (standard operating procedure(s)); t½ (elimination half-life); tmax (the median time to reach maximum plasma concentration); TBUT (Tear Film Break-up Time); TIA (transient ischemic attack); UDCA (ursodeoxycholic acid); ULN (upper limit of normal); VS (vital signs); VZV (varicella zoster virus); WBC (white blood cell); WHO (World Health Organization); and WHODRUG (World Health Organization Drug Dictionary).

Crystalline L-Arginine Salt of Compound 1

The crystalline free-plate habit or morphology and processes useful in the preparation of a crystalline free-plate habit of L-arginine salt of (R)-2-(7-(4-cyclopentyl-3-(trifluoromethyl)-benzyloxy)-1,2,3,4-tetrahydrocyclopenta[b]indol-3-yl)acetic acid are described in WO2016/209809. The plates were discovered from the novel synthetic methods and were shown to be thin hexagonal-like plates with two opposite sides of the plate being longer that the other sides (i.e., elongated hexagonal plate). However, due to the thin characteristic of the plates, a complete unbroken plate is rarely seen. Instead, what is generally observed are large to small broken pieces of the thin hexagonal-like plates. It is understood by those skilled in the art that microscopy is one of the more useful techniques to distinguish two crystalline habits or morphologies. This is particularly useful when 2 or more morphologies are associated with the same or substantially the same crystal phase as is the case with the L-arginine salt of Compound 1. Comparing the PXRD patterns of the habit prepared previously (i.e., WO2011/094008) and the plate habit prepared as described in WO2016/209809 (i.e., see FIG. 1, PXRD overlay between spherulites and plates) it was observed that the two PXRD patterns were the same or substantially the same, thus the two habits represented the same crystal phase.

Although the two habits revealed the same or substantially the same PXRD pattern, a higher degree of crystallinity was observed for the plate habit as indicated by substantially higher peak intensities and yet lower sample-related background scatter (i.e., a lower amorphous halo contribution). Since sample size and sample preparation can affect peak intensities and sample-related background scatter, and since the two habits share the same crystal phase, PXRD may not be considered the most appropriate test method to distinguish between two habits. However, PXRD does allow for determining whether two habits have the same crystal phase or different crystal phases. For determining different habits, microscopy is one of the more useful methods. Accordingly, the skilled person would be capable of reviewing a micrograph for a crystal habit and readily determine the crystal habit.

In addition to the techniques recognized in the art, specific surface can also be used to characterize a habit, such as the free-plates. Accordingly, the specific surface area values disclosed in the present invention have been obtained by means of a specific surface area analysis technique based on the BET (Brunauer, Emmett and Teller) theory, which is a well-accepted theory known in the art for the calculation of surface areas of solids by means of measuring their physical adsorption of gas molecules (see: Brunauer, S.; Emmett, P. H.; and Teller, E.; *J. Am. Chem. Soc.*, 1938, 60, 309). In particular, the specific surface area values measured in the present invention have been calculated from the BET surface area plot obtained by measuring the quantity of nitrogen gas molecules adsorbed by a weighted amount of solid at different relative pressures ($P/P_0$) within the range 0.05-0.3 ($P/P_0$), at 77.3 K. The measurement of the adsorption of gas molecules was carried out by means of a Micromeritics™ TriStar II BET surface analyzer having the characteristics as set out below in Example 3. Namely, nitrogen gas was used for the adsorption measurement. The sample for each analysis was degassed at 25° C. for 960 minutes under vacuum (i.e., 100 mm/Hg). The determination of the adsorption of nitrogen was measured at 77.3 K at eleven relative pressures ($P/P_0$) sufficiently dispersed within the range of about 0.05 to about 0.30 (i.e. eleven absolute pressures in the range of about 36 mm Hg to about 223 mm Hg relative to the saturated pressure at the time of measurement that ranged from about 738 mmHg to about 743 mmHg).

One aspect of the present invention relates to a novel crystalline plate morphology of L-arginine salt of (R)-2-(7-(4-cyclopentyl-3-(trifluoromethyl)benzyloxy)-1,2,3,4-tetrahydrocyclo-penta[b]indol-3-yl)acetic acid as described herein.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid.

In some embodiments, the crystalline free-plate habit has a powder X-ray diffraction pattern comprising peaks, in terms of 2θ, at 8.20±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.50° 0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.60°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.50±0.2°, 24.60°±0.2°, 28.8°±0.2°, and 37.3°±0.2°.

In some embodiments, the crystalline free-plate habit has a differential scanning calorimetry trace comprising an endotherm with an extrapolated onset temperature of 205.0° C. to 208.5° C. at a scan rate of 10° C./minute. In some embodiments, the crystalline free-plate habit has a differential scanning calorimetry trace comprising an endotherm with an extrapolated onset temperature of 205.0° C. to 208.1° C. at a scan rate of 10° C./minute. In some embodiments, the crystalline free-plate habit has a differential scanning calorimetry trace comprising an endotherm with an extrapolated onset temperature of 205.5° C. to 208.5° C. at a scan rate of 10° C./minute. In some embodiments, the crystalline free-plate habit has a differential scanning calorimetry trace comprising an endotherm with an extrapolated onset temperature of 206.0° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.5° C. at a scan rate of 10° C./minute. In some embodiments, the crystalline free-plate habit has a differential scanning calorimetry trace comprising an endotherm with an extrapolated onset temperature of 205.5° C. to 208.1° C. at a scan rate of 10° C./minute. In some embodiments, the crystalline free-plate habit has a differential scanning calorimetry trace comprising an endotherm with an extrapolated onset temperature of 206.5° C. to 208.1° C. at a scan rate of 10° C./minute. In some embodiments, the crystalline free-plate habit has a differential scanning calorimetry trace comprising an endotherm with an extrapolated onset temperature of 207.0° C. to 208.1° C. at a scan rate of 10° C./minute.

In some embodiments, the crystalline free-plate habit has a dynamic moisture sorption (DMS) profile with an adsorption phase from 30% RH to 90% RH wherein the crystalline free-plate habit gains about 0.3% weight or less at 90% RH. In some embodiments, the crystalline free-plate habit has a dynamic moisture sorption (DMS) profile with an adsorption phase from 30% RH to 90% RH wherein the crystalline free-plate habit gains about 0.2% weight or less at 90% RH.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a BET specific surface area of about 0.05 $m^2/g$, about 0.1 $m^2/g$, about 0.15 $m^2/g$, about 0.2 $m^2/g$, about 0.25 $m^2/g$, about 0.3 $m^2/g$, about 0.35 $m^2/g$, about 0.4 $m^2/g$, about 0.45 $m^2/g$, about 0.5 $m^2/g$, about 0.55 $m^2/g$, about 0.6 $m^2/g$, about 0.65 $m^2/g$, or about 0.7 $m^2/g$ to about 2.0 $m^2/g$, about 2.5 $m^2/g$, about 3.0 $m^2/g$, about 3.5 $m^2/g$, about 4.0 $m^2/g$, about 4.5 $m^2/g$, about 5.0 $m^2/g$, about 5.5 $m^2/g$, about 6.0 $m^2/g$, about 6.5 $m^2/g$, about 7.0 $m^2/g$, about 7.5 $m^2/g$, about 8.0 $m^2/g$, about 8.5 $m^2/g$, about 9.0 $m^2/g$, or about 9.5 $m^2/g$.

In some embodiments, the crystalline free-plate habit has a BET specific surface area of about 0.1 $m^2/g$ to about 5.0 $m^2/g$. In some embodiments, the crystalline free-plate habit has a BET specific surface area of about 0.1 $m^2/g$ to about 4.0 $m^2/g$. In some embodiments, the crystalline free-plate habit has a BET specific surface area of about 0.3 $m^2/g$ to about 4.0 $m^2/g$. In some embodiments, the crystalline free-plate habit has a BET specific surface area of about 0.5 $m^2/g$ to about 4.0 $m^2/g$. In some embodiments, the crystalline free-plate habit has a BET specific surface area of about 0.6 $m^2/g$ to about 4.0 $m^2/g$. In some embodiments, the crystalline free-plate habit has a BET specific surface area of about 0.3 $m^2/g$ to about 3.0 $m^2/g$. In some embodiments, the crystalline free-plate habit has a BET specific surface area of about 0.4 $m^2/g$ to about 2.0 $m^2/g$. In some embodiments, the crystalline free-plate habit has a BET specific surface area of about 0.5 $m^2/g$ to about 1.8 $m^2/g$. In some embodiments, the crystalline free-plate habit has a BET specific surface area of about 0.6 $m^2/g$ to about 1.6 $m^2/g$.

In some embodiments, the crystalline free-plate habit has:
1) a powder X-ray diffraction pattern comprising peaks, in terms of 2θ, at 8.2°±0.2°, 16.40±0.2°, 20.5°±0.2°, 24.6°±0.2°, 28.8°±0.2°, and 37.3°±0.2°;
2) a differential scanning calorimetry trace comprising an endotherm with an extrapolated onset temperature of 205.0° C. to 208.5° C. at a scan rate of 10° C./minute; and/or
3) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a powder X-ray diffraction pattern comprising peaks, in terms of 2θ, at 8.2°±0.2°, 16.40° 0.2°, 20.5°±0.2°, and 24.6°±0.2°;
2) a differential scanning calorimetry trace comprising an endotherm with an extrapolated onset temperature of 206.5° C. to t 208.5° C. at a scan rate of 10° C./minute; and/or
3) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a powder X-ray diffraction pattern comprising peaks, in terms of 2θ, at 8.2°±0.2°, 20.50° 0.2°, and 24.6°±0.2°;
2) a differential scanning calorimetry trace comprising an endotherm with an extrapolated onset temperature of 205.5° C. to 208.5° C. at a scan rate of 10° C./minute; and/or
3) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a powder X-ray diffraction pattern comprising peaks, in terms of 2θ, at 8.2°±0.2°, 16.4°±0.2n, and 20.5'±0.2°;
2) a differential scanning calorimetry trace comprising an endotherm with an extrapolated onset temperature of 207.1° C. to 208.1° C. at a scan rate of 10° C./minute; and/or
3) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a differential scanning calorimetry trace comprising an endotherm with an extrapolated onset temperature of 205.0° C. to 208.5° C. at a scan rate of 10° C./minute; and/or
2) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a differential scanning calorimetry trace comprising an endotherm with an extrapolated onset temperature of 206.5° C. to t 208.5° C. at a scan rate of 10° C./minute; and/or
2) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a differential scanning calorimetry trace comprising an endotherm with an extrapolated onset temperature of 205.5° C. to 208.5° C. at a scan rate of 10° C./minute; and/or
2) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a differential scanning calorimetry trace comprising an endotherm with an extrapolated onset temperature of 207.1° C. to 208.1° C. at a scan rate of 10° C./minute; and/or
2) a dynamic moisture sorption (DMS) profile with an adsorption phase from 30% RH to 90% RH wherein the crystalline free-plate habit gains about 0.2% weight or less at 90% RH. In some embodiments, the crystalline free-plate habit has:
1) a powder X-ray diffraction pattern comprising peaks, in terms of 2θ, at 8.2°±0.2°, 16.4°±0.20, and 20.50±0.20;
2) a differential scanning calorimetry trace comprising an endotherm with an extrapolated onset temperature of 205.0° C. to 208.5° C. at a scan rate of 10° C./minute;

3) a dynamic moisture sorption (DMS) profile with an adsorption phase from 30% RH to 90% RH wherein said crystalline free-plate habit gains about 0.3% weight or less at 90% RH; and/or 4) a BET specific surface area of about 0.1 m²/g to about 5.0 m²/g. In some embodiments, the crystalline free-plate habit has:

1) a powder X-ray diffraction pattern comprising peaks, in terms of 2θ, at 8.2°±0.2°, 20.5°±0.2°, and 24.6°±0.2°;

2) a differential scanning calorimetry trace comprising an endotherm with an extrapolated onset temperature of 205.5° C. to t 208.5° C. at a scan rate of 10° C./minute;

3) a dynamic moisture sorption (DMS) profile with an adsorption phase from 30% RH to 90% RH wherein said crystalline free-plate habit gains about 0.3% weight or less at 90% RH; and/or 4) a BET specific surface area of about 0.1 m²/g to about 4.0 m²/g.

In some embodiments, the crystalline free-plate habit has:

1) a powder X-ray diffraction pattern comprising peaks, in terms of 2θ, at 8.20±0.2°, 20.50°±0.2°, and 24.6°±0.2°;

2) a differential scanning calorimetry trace comprising an endotherm with an extrapolated onset temperature of 205.5° C. to t 208.5° C. at a scan rate of 10° C./minute;

3) a dynamic moisture sorption (DMS) profile with an adsorption phase from 30% RH to 90% RH wherein said crystalline free-plate habit gains about 0.3% weight or less at 90% RH; and/or 4) a BET specific surface area of about 0.3 m²/g to about 3.0 m²/g.

In some embodiments, the crystalline free-plate habit has:

1) a powder X-ray diffraction pattern comprising peaks, in terms of 2θ, at 8.20±0.2°, 16.4°±0.2°, 20.5°±0.2°, and 24.6°±0.2;

2) a differential scanning calorimetry trace comprising an endotherm with an extrapolated onset temperature of 205.5° C. to 208.5° C. at a scan rate of 10° C./minute;

3) a dynamic moisture sorption (DMS) profile with an adsorption phase from 30% RH to 90% RH wherein said crystalline free-plate habit gains about 0.3% weight or less at 90% RH; and/or 4) a BET specific surface area of about 0.6 m²/g to about 4.0 m²/g.

In some embodiments, the crystalline free-plate habit has:

1) a powder X-ray diffraction pattern comprising peaks, in terms of 2θ, at 8.2°±0.2°, 16.4°±0.2°, 20.5°±0.2°, and 24.6°±0.2°;

2) a differential scanning calorimetry trace comprising an endotherm with an extrapolated onset temperature of 206.5° C. to t 208.5° C. at a scan rate of 10° C./minute;

3) a dynamic moisture sorption (DMS) profile with an adsorption phase from 30% RH to 90% RH wherein said crystalline free-plate habit gains about 0.3% weight or less at 90% RH; and/or 4) a BET specific surface area of about 0.4 m²/g to about 2.0 m²/g.

In some embodiments, the crystalline free-plate habit has:

1) a powder X-ray diffraction pattern comprising peaks, in terms of 2θ, at 8.2°±0.2°, 16.4°±0.2°, 20.5°±0.2°, 24.6°±0.2°, and 28.8°±0.2°;

2) a differential scanning calorimetry trace comprising an endotherm with an extrapolated onset temperature of 206.5° C. to 208.1° C. at a scan rate of 10° C./minute;

3) a dynamic moisture sorption (DMS) profile with an adsorption phase from 30% RH to 90% RH wherein said crystalline free-plate habit gains about 0.2% weight or less at 90% RH; and/or 4) a BET specific surface area of about 0.5 m²/g to about 1.8 m²/g.

In some embodiments, the crystalline free-plate habit has:

1) a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.30±0.2°;

2) a differential scanning calorimetry trace comprising an endotherm with an extrapolated onset temperature of 205.5° C. to 208.1° C. at a scan rate of 10° C./minute;

3) a dynamic moisture sorption (DMS) profile with an adsorption phase from 30% RH to 90% RH wherein said crystalline free-plate habit gains about 0.2% weight or less at 90% RH; and/or 4) a BET specific surface area of about 0.6 m2/g to about 4.0 m2/g.

In some embodiments, the crystalline free-plate habit has:

1) a powder X-ray diffraction pattern comprising peaks, in terms of 2θ, at 8.2°±0.2°, 16.40°±0.2°, 20.5°±0.20, 24.6°±0.20, 28.8°±0.20, and 37.3°±0.20;

2) a differential scanning calorimetry trace comprising an endotherm with an extrapolated onset temperature of 207.1° C. to 208.1° C. at a scan rate of 10° C./minute;

3) a dynamic moisture sorption (DMS) profile with an adsorption phase from 30% RH to 90% RH wherein said crystalline free-plate habit gains about 0.2% weight or less at 90% RH; and/or 4) a BET specific surface area of about 0.6 m²/g to about 1.6 m²/g.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a powder X-ray diffraction pattern comprising peaks, in terms of 2θ, at 8.2°±0.2°, 16.40°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 20, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.20, 16.4°±0.2°, 20.5°±0.2°, 24.6°±0.2°, 28.8°±0.2°, and 37.3°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a differential scanning calorimetry trace comprising an endotherm with an extrapolated onset temperature of 205.0° C. to 208.5° C. when scanned at 10° C. per minute. In some embodiments, the crystalline free-plate habit has a differential scanning calorimetry trace comprising an endotherm with an extrapolated onset temperature of 205.0° C. to 208.1° C. at a scan rate of 10° C./minute. In some embodiments, the crystalline free-plate habit has a differential scanning calorimetry trace comprising an endotherm with an extrapolated onset temperature of 205.5° C. to 208.5° C. at a scan rate of 10° C./minute. In some embodiments, the crystalline free-plate habit has a differential scanning calorimetry trace comprising an endotherm with an extrapolated onset temperature of 205.5° C. to 208.1° C. at a scan rate of 10° C./minute. In some embodiments, the crystalline free-plate habit has a differential scanning calorimetry trace comprising an endotherm with an extrapolated onset temperature of 206.0° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.1° C. at a scan rate of 10° C./minute. In some embodiments, the crystalline free-plate habit has a differential scanning calorimetry trace comprising an endotherm with an extrapolated onset temperature of 207.0° C. to 208.1° C. at a scan rate of 10° C./minute. In some embodiments, the crystalline free-plate habit has a powder X-ray diffraction pattern comprising peaks, in terms of 2θ, at 8.2°±0.20, 16.40±0.2°, and 20.5°±0.2°. In some embodiments, the crystalline free-plate habit has a powder X-ray diffraction pattern comprising peaks, in terms of 2θ, at 8.2°±0.2°, 20.50±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.50±0.2°, and 24.6°±0.2°. In some embodiments, the crystalline free-plate habit has a powder X-ray diffraction pattern comprising peaks, in terms of 2θ, at 8.2°±0.20, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.20, 16.4°±0.2°, 20.5°±0.2°, 24.6°±0.2°, 28.8°±0.2°, and 37.3°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a dynamic moisture sorption (DMS) profile with an adsorption phase from 30% RH to 90% RH wherein the crystalline free-plate habit gains about 0.3% weight or less at 90% RH. In some embodiments, the crystalline free-plate habit has a dynamic moisture sorption (DMS) profile with an adsorption phase from 30% RH to 90% RH wherein the crystalline free-plate habit gains about 0.2% weight or less at 90% RH. In some embodiments, the crystalline free-plate habit has a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.60±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.60° 0.2°, 28.8°±0.2°, and 37.3°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a BET specific surface area of about 0.1 m²/g to about 5.0 m²/g. In some embodiments, the crystalline free-plate habit has a BET specific surface area of about 0.1 m²/g to about 4.0 m²/g. In some embodiments, the crystalline free-plate habit has a BET specific surface area of about 0.3 m²/g to about 4.0 m²/g. In some embodiments, the crystalline free-plate habit has a BET specific surface area of about 0.5 m²/g to about 4.0 m²/g. In some embodiments, the crystalline free-plate habit has a BET specific surface area of about 0.6 m²/g to about 4.0 m²/g. In some embodiments, the crystalline free-plate habit has a BET specific surface area of about 0.3 m²/g to about 3.0 m²/g. In some embodiments, the crystalline free-plate habit has a BET specific surface area of about 0.4 m²/g to about 2.0 m²/g. In some embodiments, the crystalline free-plate habit has a BET specific surface area of about 0.5 m²/g to about 1.8 m²/g. In some embodiments, the crystalline free-plate habit has a BET specific surface area of about 0.6 m²/g to about 1.6 m²/g. In some embodiments, the crystalline free-plate habit has a powder X-ray diffraction pattern comprising peaks, in terms of 2θ, at 8.2°±0.20, 16.4°±0.2°, and 20.5°±0.2°. In some embodiments, the crystalline free-plate habit has a powder X-ray diffraction pattern comprising peaks, in terms of 2θ, at 8.20±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.20, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

CERTAIN EMBODIMENTS

In its various embodiments, the present invention is directed to, inter alia, methods of treating primary biliary cholangitis (PBC) in an individual in need thereof comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of primary biliary cholangitis (PBC) in an individual.

In some embodiments, the individual was previously treated with a therapeutically effective amount of ursodeoxycholic acid (UDCA).

In some embodiments, the individual is currently treated with a therapeutically effective amount of ursodeoxycholic acid (UDCA).

In some embodiments, the therapeutically effective amount of UDCA is about 10-20 mg/kg/day. In some embodiments, the therapeutically effective amount of UDCA is about 13-15 mg/kg/day.

In some embodiments, the therapeutically effective amount of UDCA is reduced when administered with Compound 1. In some embodiments, the therapeutically effective amount of UDCA is reduced to less than 15 mg/kg/day. In some embodiments, the therapeutically effective amount of UDCA is reduced to less than 13 mg/kg/day. In some embodiments, the therapeutically effective amount of UDCA is reduced to less than 500 mg. In some embodiments, the therapeutically effective amount of UDCA is reduced to less than 500 mg per administration. In some embodiments, the therapeutically effective amount of UDCA is reduced to less than 250 mg. In some embodiments, the therapeutically effective amount of UDCA is reduced to less than 250 mg per administration. In some embodiments, the frequency of administration of UDCA is reduced. In some embodiments, the administration of UDCA is reduced to four divided doses. In some embodiments, the administration of UDCA is reduced to three divided doses. In some embodiments, the administration of UDCA is reduced to two divided doses. In some embodiments, UDCA is administered four times daily. In some embodiments, UDCA is administered three times daily. In some embodiments, UDCA is administered twice daily.

In some embodiments, the therapeutically effective amount of Compound 1 is reduced when administered with UDCA. In some embodiments, the therapeutically effective amount of Compound 1 is reduced to less than 2 mg. In some embodiments, the therapeutically effective amount of Compound 1 is reduced to less than 1.5 mg. In some embodiments, the therapeutically effective amount of Compound 1 is reduced to less than 1 mg. In some embodiments, the frequency of administration of Compound 1 is reduced. In some embodiments, Compound 1 is administered once daily. In some embodiments, Compound 1 is administered every other day.

In some embodiments, the therapeutically effective amount of UDCA is about 100 mg to about 1000 mg. In some embodiments, the therapeutically effective amount of UDCA is about 250 mg to about 500 mg. In some embodiments, the therapeutically effective amount of UDCA is about 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, or 1000 mg. In some embodiments, the therapeutically effective amount of UDCA is about 250 mg. In some embodiments, the therapeutically effective amount of UDCA is about 500 mg.

In some embodiments, the therapeutically effective amount of UDCA is administered in two to ten divided doses. In some embodiments, the therapeutically effective amount of UDCA is administered in two to four divided doses. In some embodiments, the therapeutically effective amount of UDCA is administered in two divided doses. In some embodiments, the therapeutically effective amount of UDCA is administered in three divided doses. In some embodiments, the therapeutically effective amount of UDCA is administered in four divided doses. In some embodiments, the therapeutically effective amount of UDCA is administered in five divided doses. In some embodiments, UDCA is administered four times daily. In some embodiments, UDCA is administered three times daily. In some embodiments, UDCA is administered twice daily.

In some embodiments, the therapeutically effective amount of UDCA is substantially the same amount (stable dose) for at least 6 months.

In some embodiments, the individual was previously treated with ursodeoxycholic acid (UDCA) and the individual had an inadequate response to UDCA.

In some embodiments, the individual had an inadequate response to UDCA as determined by an alkaline phosphate (ALP)>1.67× upper limit of normal (ULN) for the individual.

In some embodiments, the individual had an inadequate response after 6 months of treatment with UDCA.

In some embodiments, the individual had an inadequate response after 6 months of treatment with UDCA and an alkaline phosphate (ALP)>1.67× upper limit of normal (ULN).

In some embodiments, the treatment dose of UDCA was at least 13 mg/kg/day.

In some embodiments, the individual has at least one primary biliary cholangitis diagnosis criteria selected from the group consisting of:
 anti-mitochondrial antibody (AMA) titer >1:40;
 alkaline phosphate (ALP)>1.5×ULN for at least 6 months; and
 liver biopsy findings consistent with PBC.

In some embodiments, the individual has at least two primary biliary cholangitis diagnosis criteria selected from the group consisting of:
 anti-mitochondrial antibody (AMA) titer >1:40;
 alkaline phosphate (ALP)>1.5×ULN for at least 6 months; and
 liver biopsy findings consistent with PBC.

In some embodiments, the individual has at least one of the criteria selected from the group consisting of:
 ALP>1.67×ULN but <10×ULN;
 ALT and AST<5×ULN;
 total bilirubin <1.5×ULN;
 international normalized ratio (INR)<1.2×ULN; and
 serum creatinine <1.5 mg/dL (133 μmol/L).

In some embodiments, the individual has at least one of the criteria selected from the group consisting of:
 ALP>1.67×ULN but <10×ULN;
 ALT and AST<5×ULN;
 total bilirubin <ULN;
 international normalized ratio (INR)<1.2×ULN; and
 serum creatinine <1.5 mg/dL (133 μmol/L).

In some embodiments, the individual has at least one of the criteria selected from the group consisting of:
 ALP>1.67×ULN but <10×ULN;
 ALT and AST<5×ULN;
 total bilirubin <1.5×ULN;
 international normalized ratio (INR)<1.2×ULN;
 platelet count >150,000;
 serum albumin >3.4 g/dL;
 serum creatinine <1.5 mg/dL (133 μmol/L);
 TSH<5.0 mU/L without clinical significant changes of free T3 and T4 levels; and
 Fibroscan (transient elastography)<10 kPa.

In some embodiments, the individual has at least one of the criteria selected from the group consisting of:
 ALP>1.67×ULN but <10×ULN;
 ALT and AST<5×ULN;
 total bilirubin <ULN;
 international normalized ratio (INR)<1.2×ULN;
 platelet count >150,000/mm$^3$;
 serum albumin >3.0 g/dL;
 serum creatinine <1.5 mg/dL (133 μmol/L);
 TSH<5.0 mU/L without clinical significant changes of free T3 and T4 levels; and
 Fibroscan® (transient elastography)<10 kPa.

In some embodiments, the individual has at least two of the criteria selected from the group consisting of:
 ALP>1.67×ULN but <10×ULN;
 ALT and AST<5×ULN;
 total bilirubin <1.5×ULN;
 international normalized ratio (INR)<1.2×ULN;
 platelet count >150,000/mm$^3$;
 serum albumin >3.4 g/dL;
 serum creatinine <1.5 mg/dL (133 μmol/L);

TSH<5.0 mU/L without clinical significant changes of free T3 and T4 levels; and
Fibroscan (transient elastography)<10 kPa.
In some embodiments, the individual has at least two of the criteria selected from the group consisting of:
ALP>1.67×ULN but <10×ULN;
ALT and AST<5×ULN;
total bilirubin <1.5×ULN;
international normalized ratio (INR)<1.2×ULN;
platelet count >150,000/mm$^3$;
serum albumin >3.4 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least three of the criteria selected from the group consisting of:
ALP>1.67×ULN but <10×ULN;
ALT and AST<5×ULN;
total bilirubin <1.5×ULN;
international normalized ratio (INR)<1.2×ULN;
platelet count >150,000/mm$^3$;
serum albumin >3.4 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least three of the criteria selected from the group consisting of:
ALP>1.67×ULN but <10×ULN;
ALT and AST<5×ULN;
total bilirubin <ULN;
international normalized ratio (INR)<1.2×ULN;
platelet count >150,000/mm$^3$;
serum albumin >3.0 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least four of the criteria selected from the group consisting of:
ALP>1.67×ULN but <10×ULN;
ALT and AST<5×ULN;
total bilirubin <1.5×ULN;
international normalized ratio (INR)<1.2×ULN;
platelet count >150,000/mm$^3$;
serum albumin >3.4 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least four of the criteria selected from the group consisting of:
ALP>1.67×ULN but <10×ULN;
ALT and AST<5×ULN;
total bilirubin <ULN;
international normalized ratio (INR)<1.2×ULN;
platelet count >150,000/mm$^3$;
serum albumin >3.0 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least five of the criteria selected from the group consisting of:
ALP>1.67×ULN but <10×ULN;
ALT and AST<5×ULN;
total bilirubin <1.5×ULN;
international normalized ratio (INR)<1.2×ULN;
platelet count >150,000/mm$^3$;
serum albumin >3.4 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least five of the criteria selected from the group consisting of:
ALP>1.67×ULN but <10×ULN;
ALT and AST<5×ULN;
total bilirubin <ULN;
international normalized ratio (INR)<1.2×ULN;
platelet count >150,000/mm$^3$;
serum albumin >3.0 g/dL;
scrum creatinine <1.3 mg/dL (133 µmol/L);
TSH<5.0 mU/L without clinical significant changes of free T3 and T4 levels; and
Fibroscan (transient elastography)<10 kPa.
In some embodiments, the individual has at least six of the criteria selected from the group consisting of:
ALP>1.67×ULN but <10×ULN;
ALT and AST<5×ULN;
total bilirubin <1.5×ULN;
international normalized ratio (INR)<1.2×ULN;
platelet count >150,000/mm$^3$;
serum albumin >3.4 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least six of the criteria selected from the group consisting of:
ALP>1.67×ULN but <10×ULN;
ALT and AST<5×ULN;
total bilirubin <ULN;
international normalized ratio (INR)<1.2×ULN;
platelet count >150,000/mm$^3$;
serum albumin >3.0 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least seven of the criteria selected from the group consisting of:
ALP>1.67×ULN but <10×ULN;
ALT and AST<5×ULN;
total bilirubin <1.5×ULN;
international normalized ratio (INR)<1.2×ULN;
platelet count >150,000/mm$^3$;
serum albumin >3.4 g/dL;
serum creatinine <1.5 mg/dL (133 µmol/L);
TSH<5.0 mU/L without clinical significant changes of free T3 and T4 levels; and
Fibroscan (transient elastography)<10 kPa.
In some embodiments, the individual has at least seven of the criteria selected from the group consisting of:
ALP>1.67×ULN but <10×ULN;
ALT and AST<5×ULN;
total bilirubin <UI N;
international normalized ratio (INR)<1.2×ULN;
platelet count >150,000/mm$^3$;
serum albumin >3.0 g/dL;
serum creatinine <1.5 mg/dL (133 µmol/L);

TSH<5.0 mU/L without clinical significant changes of free T3 and T4 levels; and

Fibroscan (transient elastography)<10 kPa.

In some embodiments, the individual has at least eight of the criteria selected from the group consisting of:

ALP>1.67×ULN but <10×ULN;
ALT and AST<5×ULN;
total bilirubin <1.5×ULN;
international normalized ratio (INR)<1.2×ULN;
platelet count >150,000/mm³;
serum albumin >3.4 g/dL;
serum creatinine <1.5 mg/dL (133 µmol/L);
TSH<5.0 ml J/L without clinical significant changes of free T3 and T4 levels; and Fibroscan (transient elastography)<10 kPa.

In some embodiments, the individual has at least eight of the criteria selected from the group consisting of:

ALP>1.67×ULN but <10×ULN;
ALT and AST<5×ULN;
total bilirubin <ULN;
international normalized ratio (INR)<1.2×ULN;
platelet count >150,000/mm³;
serum albumin >3.0 g/dL;
serum creatinine <1.5 mg/dL (133 µmol/L);
TSH<5.0 mU/L without clinical significant changes of free T3 and T4 levels; and Fibroscan (transient elastography)<10 kPa.

In some embodiments, the individual has all the criteria selected from the group consisting of:

ALP>1.67×ULN but <10×ULN;
ALT and AST<5×ULN;
total bilirubin <1.5×ULN;
international normalized ratio (INR)<1.2×ULN;
platelet count >150,000/mm³;
serum albumin >3.4 g/dL;
serum creatinine <1.5 mg/dL (133 µmol/L);
TSH<5.0 mU/L without clinical significant changes of free T3 and T4 levels; and Fibroscan (transient elastography)<10 kPa.

In some embodiments, the individual has all the criteria selected from the group consisting of:

ALP>1.67×ULN but <10×ULN;
ALT and AST<5×ULN;
total bilirubin <ULN;
international normalized ratio (INR)<1.2×ULN;
platelet count >150,000/mm³;
serum albumin >3.0 g/dL;
serum creatinine <1.5 mg/dL (133 µmol/L);
TSH<5.0 mU/L without clinical significant changes of free T3 and T4 levels; and Fibroscan (transient elastography)<10 kPa.

In some embodiments, the individual has at least one additional condition selected from the group consisting of: pruritus, fatigue, osteoporosis, vitamin deficiencies, dry eyes and/or mouth, portal hypertension, and pain.

In some embodiments, the therapeutically effective amount of Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration.

In some embodiments, the Compound 1, or a pharmaceutically acceptable salt, hydrate, or solvate thereof, is formulated as a tablet suitable for oral administration.

In some embodiments, the individual is administered a titration dose of Compound 1 prior to the administering the therapeutically effective amount of Compound 1, wherein the titration dose is less than the therapeutically effective amount of Compound 1.

In some embodiments, the titration dose is less than about 2 mg of Compound 1.

In some embodiments, the titration dose is maintained until there are no significant changes in vital signs and/or EKG of the individual.

In some embodiments, the titration dose is maintained until the pulse rate ≥55 bpm, systolic blood pressure (SBP) ≥90, and diastolic blood pressure (DBP) ≥55 mmHg in the individual.

In some embodiments, the titration dose is maintained for no more than 14 days prior to administering the therapeutically effective amount of Compound 1.

In some embodiments, the titration dose comprises a first titration dose and a second titration dose, wherein the first titration dose is less than the second titration dose and each titration dose is less than the therapeutically effective amount of Compound 1.

In some embodiments, the first titration dose is in an amount equivalent to about 1 mg of Compound 1.

In some embodiments, the second titration dose is in an amount equivalent to about 1.5 mg of Compound 1.

In some embodiments, the first titration dose is in an amount equivalent to about 1 mg of Compound 1 and the second titration dose is in an amount equivalent to about 1.5 mg of Compound 1.

In some embodiments, the first titration dose is maintained for no more than 7 days prior to administering the second titration dose.

In some embodiments, the second titration dose is maintained for no more than 7 days prior to administering the therapeutically effective amount of Compound 1.

In some embodiments, the therapeutically effective amount of Compound 1, or a pharmaceutically acceptable salt, hydrate, or solvate thereof, is in an amount equivalent to about 1.0 mg to about 5 mg of Compound 1.

In some embodiments, the therapeutically effective amount of Compound 1, or a pharmaceutically acceptable salt, hydrate, or solvate thereof, is in an amount equivalent to about 1 mg to about 2 mg.

In some embodiments, the therapeutically effective amount of Compound 1, or a pharmaceutically acceptable salt, hydrate, or solvate thereof, is in an amount equivalent to about 1 mg, about 1.25 mg, about 1.5 mg, about 1.75, or about 2 mg.

In some embodiments, the therapeutically effective amount of Compound 1, or a pharmaceutically acceptable salt, hydrate, or solvate thereof, is in an amount equivalent to about 1 mg or about 2 mg.

In some embodiments, the therapeutically effective amount of Compound 1, or a pharmaceutically acceptable salt, hydrate, or solvate thereof, is in an amount equivalent to about 1 mg of Compound 1.

In some embodiments, the therapeutically effective amount of Compound 1, or a pharmaceutically acceptable salt, hydrate, or solvate thereof, is in an amount equivalent to 1.1 mg, 1.2 mg, 1.3 mg, 1.4 mg, 1.5 mg, 1.6 mg, 1.7 mg, 1.8 mg, 1.9 mg, or 2 mg of Compound 1.

In some embodiments, the therapeutically effective amount of Compound 1, or a pharmaceutically acceptable salt, hydrate, or solvate thereof, is in an amount equivalent to ≥1 mg of Compound 1. In some embodiments, the therapeutically effective amount of Compound 1, or a pharmaceutically acceptable salt, hydrate, or solvate thereof, is in an amount equivalent to ≥1.5 mg of Compound 1. In some embodiments, the therapeutically effective amount of Compound 1, or a pharmaceutically acceptable salt, hydrate, or solvate thereof, is in an amount equivalent to 1 mg of Compound 1. In some embodiments, the therapeutically effective amount of Compound 1, or a pharmaceutically acceptable salt, hydrate, or solvate thereof, is in an amount equivalent to ≤1.5 mg of Compound 1. In some embodiments, the therapeutically effective amount of Compound 1, or a pharmaceutically acceptable salt, hydrate, or solvate thereof, is in an amount equivalent to ≤2 mg of Compound 1. In some embodiments, the therapeutically effective amount of Compound 1, or a pharmaceutically acceptable salt, hydrate, or solvate thereof, is no more than 1 mg, 1.5 mg, 2 mg, or 5 mg of Compound 1.

In some embodiments, the therapeutically effective amount of Compound 1, or a pharmaceutically acceptable salt, hydrate, or solvate thereof, is administered once daily.

In some embodiments, the therapeutically effective amount of Compound 1, or a pharmaceutically acceptable salt, hydrate, or solvate thereof, is in an amount equivalent to about 2 mg of Compound 1.

In some embodiments, the Compound 1, or a pharmaceutically acceptable salt, hydrate, or solvate thereof, is selected from: Compound 1, a calcium salt of Compound 1, and an L-arginine salt of Compound 1.

In some embodiments, the Compound 1, or a pharmaceutically acceptable salt, hydrate, or solvate thereof, is an L-arginine salt of Compound 1.

In some embodiments, the Compound 1, or a pharmaceutically acceptable salt, hydrate, or solvate thereof, is an anhydrous, non-solvated crystalline form of the L-arginine salt of Compound 1.

In some embodiments, the Compound 1, or a pharmaceutically acceptable salt, hydrate, or solvate thereof, is a crystalline free-plate habit of the non-solvated L-arginine salt of Compound 1.

In some embodiments, the Compound 1, or a pharmaceutically acceptable salt, hydrate, or solvate thereof, is an anhydrous, non-solvated crystalline form of Compound 1.

In some embodiments, the method further comprises administering Compound 1, or a pharmaceutically salt, solvate, or hydrate thereof, in combination with a therapeutically effective amount of with a compound selected from the group consisting of: an antihistamine (diphenhydramine), cholestyramine (questran, prevalite), rifampin, an opioid antagonist (naloxone), pilocarpine (isopto carpine, salagen), cevimeline (evoxac), calcium and/or vitamin D supplement, and vitamin A, D, E and/or K supplement.

Some embodiments of the present invention related to titration packages for enabling compliance with a regimen of changing dosage of a medication over a period of time for the treatment of primary biliary cholangitis (PBC), wherein the medication is (R)-2-(7-(4-cyclopentyl-3-(trifluoromethyl)benzyloxy)-1,2,3,4-tetrahydrocyclo-penta[b]indol-3-yl)acetic acid (Compound 1) or a pharmaceutically salt, solvate, or hydrate thereof, the package comprising:

a first number of daily units of a pharmaceutical composition comprising one or more doses of Compound 1, or a pharmaceutically acceptable salt, hydrate, or solvate thereof, wherein each dose is in an amount equivalent to about 1.5 mg or less of Compound 1, and a second number of daily units of a pharmaceutical composition comprising a standard dose of Compound 1, or a pharmaceutically acceptable salt, hydrate, or solvate thereof, is in an amount equivalent to about 1.0 to about 2.5 mg of Compound 1.

In some embodiments, the dose of the first number of daily units is in an amount equivalent to about 1 mg of Compound 1.

In some embodiments, the dose of the first number of daily units is in an amount equivalent to about 1.5 mg of Compound 1.

In some embodiments, the dose of the second number of daily units is in an amount equivalent to about 2 mg of Compound 1.

In some embodiments, the dose of the first number of daily units is in an amount equivalent to about 1 mg or 1.5 mg of Compound l and the dose of the second number of daily units is in an amount equivalent to about 2 mg of Compound 1.

Some embodiments relate to kits comprising a titration package according to any previous embodiment, and instructions indicating that the medication is to be administered to an individual in need of treatment of primary biliary cholangitis (PBC).

In some embodiments, the individual is administered the therapeutically effective amount of Compound 1 once daily.

In some embodiments, the individual is administered the therapeutically effective amount of Compound 1 twice daily.

In some embodiments, the individual is administered the therapeutically effective amount of Compound 1 three times daily.

In some embodiments, the individual is administered the therapeutically effective amount of Compound 1 once every other day.

In some embodiments, Compound 1 is administered without food.

In some embodiments, the individual has been identified as having impaired liver function prior to administration of the titration dose.

Some embodiments relate to methods, further comprising:
identifying the liver function of the individual; and
administering at least one titration dose if the individual has impaired liver function, or
not administering a titration dose if the individual does not have impaired liver function.

Some embodiments relate to methods, wherein impaired liver function of the individual is determined by a liver function test for at least one marker selected from: bilirubin, albumin, total protein, aminotransferase (ALT), aspartate aminotransferase (AST), creatinine kinase (CK), gamma-glutamyl transferase (GGT), or alkaline phosphatase (ALP).

One aspect of the present invention relates to methods of treating an individual in need thereof with (R)-2-(7-(4-cyclopentyl-3-(trifluoromethyl)benzyloxy)-1,2,3,4-tetrahydrocyclo-penta[b]indol-3-yl)acetic acid (Compound 1) comprising:

(a) analyzing one or more samples from the individual for the level of at least one biomarker obtained prior to the treatment with Compound 1; and (b) administering Compound 1 or not administering Compound 1 to the individual based on a predetermined level of the at least one biomarker prior to treatment of Compound 1;

wherein the at least one biomarker is selected from the group consisting of: (i) anti-gp210; (ii) anti-sp100; (iii) serum high sensitivity C-reactive protein (hsCRP); (iv) alanine transaminase (ALT); (v) aspartate transaminase (AST); (vi) gamma-glutamyl transferase (GGT); (vii) anti-mitochondrial antibodies (AMA); (viii) Golgi protein 73 (GP73); (viii) bile acid; (x) complement factor 4 (C4); (xi) IgG; and (xii) IgM.

One aspect of the present invention relates to methods of treating an individual in need thereof with (R)-2-(7-(4-cyclopentyl-3-(trifluoromethyl)benzyloxy)-1,2,3,4-tetrahydrocyclo-penta[b]indol-3-yl)acetic acid (Compound 1) comprising:

(a) administering Compound 1 to the individual;

(b) analyzing one or more samples from the individual for the level of at least one biomarker obtained after the treatment with Compound 1; and (c) (i) continuing administration of Compound 1 if the at least one biomarker is less than or equal to a predetermined level for the at least one biomarker prior to treatment of Compound 1; or (ii) discontinuing administration of Compound 1 if the at least one biomarker is greater than a predetermined level for the at least one biomarker prior to treatment of Compound 1;

wherein the at least one biomarker is selected from the group consisting of: (i) anti-gp210; (ii) anti-sp100; (iii) serum high sensitivity C-reactive protein (hsCRP); (iv) alanine transaminase (ALT); (v) aspartate transaminase (AST); (vi) gamma-glutamyl transferase (GGT); (vii) antimitochondrial antibodies (AMA); (viii) Golgi protein 73 (GP73); (viii) bile acid; (x) complement factor 4 (C4); (xi) IgG; and (xii) IgM.

One aspect of the present invention relates to methods of treating an individual in need thereof with (R)-2-(7-(4-cyclopentyl-3-(trifluoromethyl)benzyloxy)-1,2,3,4-tetrahydrocyclo-penta[b]indol-3-yl)acetic acid (Compound 1) comprising:

(a) analyzing one or more samples from the individual for a first level of at least one biomarker obtained prior to the treatment with Compound 1;

(b) administering Compound 1 to the individual;

(c) analyzing one or more samples from the individual for a second level of the at least one biomarker obtained after the treatment with Compound 1; and (d). (i) continuing administration of Compound 1 if the second level of the at least one biomarker in step (c) is less than or about equal to the corresponding first level of the at least one biomarker in step (a); or (ii) discontinuing administration of Compound 1 if the second level of the at least one biomarker in step (c) is greater than the corresponding first level of the at least one biomarker in step (a);

wherein the at least one biomarker is selected from the group consisting of: (i) anti-gp210; (ii) anti-sp100; (iii) serum high sensitivity C-reactive protein (hsCRP); (iv) alanine transaminase (ALT); (v) aspartate transaminase (AST); (vi) gamma-glutamyl transferase (GGT); (vii) antimitochondrial antibodies (AMA); (viii) Golgi protein 73 (GP73); (viii) bile acid; (x) complement factor 4 (C4); (xi) IgG; and (xii) IgM.

In some embodiments, the individual has primary biliary cholangitis (PBC).

In some embodiments, the individual has fatigue, pruritus, eye dryness, and/or Sjögren's syndrome (SS).

In some embodiments, the individual has fatigue.

In some embodiments, the individual has pruritus.

In some embodiments, the individual has eye dryness.

In some embodiments, the individual has Sjögren's syndrome (SS).

In some embodiments, the second level of the at least one biomarker in step (c) is 2% less, 5% less, 10% less, 12% less, 15% less, 17% less, 20% less, 22% less, 25% less, 30% less, 35% less, 40% less, 45% less, 50% less, or >50% less than the corresponding first level of the at least one biomarker in step (a).

In some embodiments, the at least one biomarker is two, three, four, five, six, seven, eight, nine, ten, eleven, or twelve biomarkers selected from the group consisting of: (i) anti-gp210; (ii) anti-sp100; (iii) serum high sensitivity C-reactive protein (hsCRP); (iv) alanine transaminase (ALT); (v) aspartate transaminase (AST); (vi) gamma-glutamyl transferase (GGT); (vii) antimitochondrial antibodies (AMA); (viii) Golgi protein 73 (GP73); (viii) bile acid; (x) complement factor 4 (C4); (xi) IgG; and (xii) IgM.

In some embodiments, the at least one biomarker in step (c) is two, three, four, five, six, seven, eight, nine, ten, eleven, or twelve biomarkers selected from the group consisting of: (i) anti-gp210; (ii) anti-sp100; (iii) serum high sensitivity C-reactive protein (hsCRP); (iv) alanine transaminase (ALT); (v) aspartate transaminase (AST); (vi) gamma-glutamyl transferase (GGT); (vii) antimitochondrial antibodies (AMA); (viii) Golgi protein 73 (GP73); (viii) bile acid; (x) complement factor 4 (C4); (xi) IgG; and (xii) IgM.

One aspect of the present invention relates to methods of treating fatigue in an individual in need thereof comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

One aspect of the present invention relates to methods of treating fatigue in an individual with primary biliary cholangitis (PBC) comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

One aspect of the present invention relates to methods of treating pruritus in an individual in need thereof comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

One aspect of the present invention relates to methods of treating pruritus in an individual with primary biliary cholangitis (PBC) comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

One aspect of the present invention relates to methods of treating eye dryness in an individual in need thereof comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

One aspect of the present invention relates to methods of treating eye dryness in an individual with primary biliary cholangitis (PBC) comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

One aspect of the present invention relates to methods of treating Sjögren's syndrome (SS) in an individual in need thereof comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

One aspect of the present invention relates to methods of treating Sjögren's syndrome (SS) in an individual with primary biliary cholangitis (PBC) comprising administering a therapeutically effective amount of (R)-2-(7-(4-cyclopentyl-3-(trifluoromethyl)benzyloxy)-1,2,3,4-tetrahydrocyclo-penta[b]indol-3-yl)acetic acid (Compound 1), or a pharmaceutically salt, solvate, or hydrate thereof.

One aspect of the present invention relates to methods of treating an individual in need thereof with (R)-2-(7-(4-cyclopentyl-3-(trifluoromethyl)benzyloxy)-1,2,3,4-tetrahydrocyclo-penta[b]indol-3-yl)acetic acid (Compound 1) comprising:

(a) analyzing one or more samples from the individual for a level of at least one biomarker obtained prior to the treatment with Compound 1; and (d) modifying administration of Compound 1, wherein the at least one biomarker is selected from the group consisting of: (i) anti-gp210; (ii) anti-sp100; (iii) serum high sensitivity C-reactive protein (hsCRP); (iv) alanine transaminase (ALT); (v) aspartate transaminase (AST); (vi) gamma-glutamyl transferase (GGT); (vii) anti-mitochondrial antibodies (AMA); (viii) Golgi protein 73 (GP73); (viii) bile acid; (x) complement factor 4 (C4); (xi) IgG; and (xii) IgM.

In some embodiments, modifying the administration of Compound 1 comprises increasing the amount of Compound 1.

In some embodiments, modifying the administration of Compound 1 comprises decreasing the amount of Compound 1.

In some embodiments, the individual has been administered Compound 1 prior to modified administration.

In some embodiments, the amount of UDCA is about 13 mg/kg/day to about 15 mg/kg/day.

In some embodiments, the UDCA is administered in two to four divided doses.

In some embodiments, the amount of UDCA is about 250 mg or about 500 mg.

In some embodiments, the amount or frequency of administration of UDCA is reduced when administered with Compound 1.

In some embodiments, the amount or frequency of administration of Compound 1 is reduced when administered with UDCA.

Pharmaceutical Compositions A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or suspensions, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a salt, solvate, hydrate or physiologically functional derivative thereof can be used as active ingredients in pharmaceutical compositions, specifically as S1P1 receptor modulators. The term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary and as is customary and known to the physician, it is to be tailored to the individual conditions in each individual case. It depends, for example, on the nature and severity of the illness to be treated, on the condition of the individual, or on whether an acute or chronic disease state is treated or prophylaxis is conducted or on whether further active compounds are administered in addition to the compounds of the present invention. Representative doses of the present invention include, but are not limited to, about 1 mg to about 5 mg, about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, and about 5 mg. Multiple doses may be administered during the day, especially when relatively large amounts are deemed to be needed, for example 2, 3 or 4 doses. Depending on the individual and as deemed appropriate by the individual's physician or caregiver it may be necessary to deviate upward or downward from the doses described herein.

The amount of active ingredient or an active salt, solvate or hydrate derivative thereof, required for use in treatment will vary not only with the particular salt selected but also with the route of administration, the nature of the condition being treated and the age and condition of the individual and will ultimately be at the discretion of the attendant physician or clinician. Representative factors include the type, age, weight, sex, diet and medical condition of the individual, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis is conducted or whether further active compounds are administered in addition to the compounds of the present invention and as part of a drug combination. The dosage regimen for treating a disease condition with the compounds and/or compositions of this invention is selected in accordance with a variety factors including those cited above. Thus, the actual dosage regimen employed may vary widely and therefore may deviate from a preferred dosage regimen and one skilled in the art will recognize that dosage and dosage regimens outside these typical ranges can be tested and, where appropriate, may be used in the methods of this invention.

The desired dose may conveniently be presented in a single dose or as divided doses administered at appropriate intervals, for example, as 2, 3, 4 or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

For preparing pharmaceutical compositions from the compounds of the present invention, the suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or encapsulating materials.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may be from 0.5 to about 90 percent of the active compound. However, an artisan would know when amounts outside of this range are necessary. Suitable carriers for powders and tablets include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein (e.g., by stirring). The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the individual administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols (e.g., nasal aerosols, by inhalation), this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. Solutions or dispersions of the compounds of the present invention or a pharmaceutically acceptable salt, solvate, hydrate or derivative thereof in water, water/alcohol mixtures or suitable saline solutions, for example, can be employed using customary additives (e.g., benzyl alcohol or other suitable preservatives), absorption enhancers for increasing the bioavailability, solubilizers, dispersants and others and, if appropriate, customary propellants (e.g., carbon dioxide, CFCs, such as, dichlorodifluoromethane, trichlorofluoromethane, dichlorotetrafluoroethane and the like). The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively, the active ingredients may be provided in the form of a dry powder (e.g., a powder mix of the compound in a suitable powder base such as lactose, starch, starch derivatives such as hydroxypropylmethyl cellulose and polyvinylpyrrolidone (PVP)). Conveniently the powder carrier will form a gel in the nasal cavity. The powder composition may be presented in unit dose form (e.g., capsules, cartridges) as for gelatin or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

In some embodiments, the compositions are tablets or capsules for oral administration.

In some embodiments, the compositions are liquids for intravenous administration.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., Journal of Pharmaceutical Sciences, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and that when administered into an individual undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Preparation of Compounds

The preparation of Compound 1, including certain crystal forms of Compound 1 are described in International Patent Application No. PCT/US2009/004265, published as International Publication No. WO2010/011316; and International Patent Application No. PCT/US2011/000153, published as International Publication No. WO2011/094008; the entire contents of each are incorporated herein by reference in their entirety.

The preparation of the crystal form and crystalline free-plate habit of the non-solvated L-arginine salt of Compound 1 is described in International Patent Application No. PCT/US2016/038506, published as International Publication No. WO2016/209809, the entire contents of which are incorporated herein by reference in their entirety.

Example 2: Clinical Trial for Treating Primary Biliary Cholangitis (PBC) with Compound 1

A phase I/II, open-label, single arm, proof-of-concept study is performed to evaluate the safety, tolerability and efficacy of Compound 1 in individuals with primary biliary cholangitis (PBC). The study is conducted in individuals aged 18 to 80 years old (inclusive) who have PBC and an inadequate response to ursodeoxycholic acid (UDCA) and are on a stable dose of UDCA for at least 6 months prior to screening. The trial includes an initial pilot study to assess pharmacokinetics and tolerability for up to ten individuals.

Primary objectives include efficacy (i.e., changes in ALP levels from baseline), safety and tolerability of Compound 1 in individuals with PBC over a 24-week treatment period.

Exploratory objectives include assessment of the following: 1) the pharmacokinetic (PK) profile of Compound 1 in individuals with PBC; 2) the pharmacodynamic (PD) response (lymphocyte counts and subsets thereof) and changes in antinuclear antibodies (ANA) (anti-gp210 and anti-sp100) and other exploratory biomarkers over a 24-week treatment period; 3) serum high sensitivity C-reactive protein (hsCRP), alanine transaminase (ALT), aspartate transaminase (AST), gamma-glutamyl transferase (GGT), antimitochondrial antibodies (AMA), Golgi protein 73 (GP73), complement factor 4 (C4), bile acid, total IgG, total IgM, over a 24-week treatment period; 4) complete blood count (CBC); 5) quality of life (QoL) and incidence of pruritus and/or fatigue over a 24-week treatment period; 6) safety, tolerability and efficacy of Compound 1 over a 12-week period; 7) liver stiffness using transient elastography over a 24-week treatment period; and 8) changes in eye dryness, the Schirmer test and tear breakup time (TBUT) test over a 24-week treatment period in individuals with abnormal results at screening.

Individuals are screened for up to four weeks, then administered 1 or 2 mg of Compound 1 for 24 consecutive weeks. Safety laboratory parameters, vital signs, physical examination, and concomitant medications are evaluated during the screening period, and Child-Pugh scores may be calculated. The trial is conducted as follows:

1) A four-week pilot study is run to assess safety and tolerability, including PK and maximum tolerated dose, in up to 10 individuals before proceeding with the remainder of the clinical trial. Individuals are admitted to the clinic on Day −1 and stay until Day 3. Vital signs and EKG changes are monitored extensively during this time. Individuals have abbreviated PK sampling pre-dose (baseline) and at 0.5, 1, 2, 4, 6, 8, and 12 hours after dosing on Day 1, and 6 hours post-dosing on Days 2 and 3. Individuals receive 1 mg of Compound 1 (PO, QD) on Days 1, 2, and 3. If 1 mg of Compound 1 is well tolerated and there are no clinically significant changes in vital signs and EKG, the 1 mg dose level is maintained and the individual is discharged on Day 3. If 1 mg is not tolerated, then treatment is stopped if any of the following findings are made during treatment:

Certain ECG changes (e.g., if a QTc interval ≥500 msec is observed and confirmed, extended monitoring is performed until the findings have resolved and dosing is stopped);

ALT/AST >3× baseline level and >ULN; or

Total bilirubin >2× baseline level and >1.5 mg/dL.

The 1 mg dose level may be increased to 2 mg at Week 4 based on the individual's safety and PK data. Individuals with dose escalation on Week 4 have an additional PK sampling, and vital signs and ECG monitoring are performed every 30 minutes until at least 6 hours post dosing. Dosage is maintained at 2 mg QD if possible, but may return to 1 mg QD if deemed necessary.

2) Based on the above pilot study data, subsequent individuals are admitted to the clinic on Day −1 and start treatment on Day 1 (1 mg QD). PK sampling is performed up to 45 minutes pre-dose, and at 0.5, 1, 2, 4, 6, and 8 hours post dosing on Day 1. Vital signs and EKG changes are closely monitored. Additional PK samples are collected pre-dose on Weeks 1, 2, 4, 8, 12, 16, 20, and 24. The 1 mg dose level may be increased to 2 mg at Week 4 based on the individual's safety and PK data. If 1 mg is not tolerated, treatment is stopped as described above. Individuals with dose escalation on Week 4 have an additional PK sampling, and vital signs and ECG monitoring are performed every 30 minutes until at least 6 hours post dosing. Dosage is maintained at 2 mg QD if possible, but may return to 1 mg QD if deemed necessary. Safety and tolerability are assessed by monitoring adverse events and vital signs, ECG, and blood tests. Individuals return to the study site at Weeks 1, 2, 4, 8, 12, 16, 20, and 24 for examinations as described in Schedule of Procedures and Visits (FIGS. 2 to 6).

The last dose of Compound 1 is administered one day before the end of the 24-week treatment period.

Individuals return to the study site for the final visit two weeks after the end of 24-week treatment, and final procedures are performed per Schedule of Procedures and Visits (FIGS. 2 to 6).

ALP, GGT, ALT/AST, bilirubin (total and direct), PT/INR, albumin, lipid panel, and total serum IgG/IgM as well as a PBC-40 questionnaire and a 5-D Pruritus scale/VAS are measured during the study period.

Individuals must meet the inclusion and exclusion criteria described below to be enrolled in the study.

Inclusion Criteria:
1. Individuals must be males or females aged 18 to 80 years (inclusive) at the time of screening, with confirmed PBC diagnosis based upon at least two of the following three criteria:
   anti-mitochondrial antibody (AMA) titer >1:40;
   alkaline phosphate (ALP)>1.5×ULN for at least 6 months; and
   liver biopsy findings consistent with PBC.
2. An inadequate response to UDCA, as defined by an alkaline phosphate (ALP)>1.67×ULN after 6 months of UDCA at a minimum dose of 13 mg/kg/day.
3. Individuals must be on a stable dose of UDCA for at least 3 months prior to screening.
4. Individuals taking medications for pruritus or fatigue must have been on stable doses of these medications for at least two weeks prior to Day 1.
5. Individuals must have the following laboratory parameters at screening:
   ALP>1.67×ULN but <10×ULN
   ALT and AST<5×ULN
   total bilirubin <ULN
   international normalized ratio (INR)<1.2×ULN
   platelet count >150,000/mm$^3$ (>150×10$^9$/L)
   serum albumin >3.0 g/dL (>30 g/L)
   serum creatinine <1.5 mg/dL (133 µmol/L)
   estimated glomerular filtration rate (eGFR) ≥60 mL/min/1.73 m$^2$
   TSH<5.0 mU/L without clinical significant changes of free T3 and T4 levels
   Fibroscan® (transient elastography)<10 kPa
6. Individuals are considered to be in stable health in the opinion of the investigator as determined by:
   a) a screening physical examination with no clinically significant abnormalities unrelated to PBC.
   b) vital signs at screening: pulse rate ≥55 bpm, systolic blood pressure (SBP) ≥90, and diastolic blood pressure (DBP) ≥55 mmHg.
   c) no clinical abnormalities noted in the 12-lead electrocardiogram (ECG) in the opinion of the investigator (see also exclusion criteria #22 and #23).
   d) no evidence of macular edema in an ophthalmology evaluation (performed by an ophthalmologist), supported with optical coherence tomography (OCT), where available (dependent on site capability) at screening or no later than three months prior to screening.

Exclusion Criteria:
1. Chronic liver disease of a non-PBC etiology. However, PBC patients accompanied with primary Sjögren's syndrome (pSS) are eligible to be enrolled.
2. History or evidence of clinically significant hepatic decompensation:
   a) Portal hypertension, cirrhosis and complications of cirrhosis/portal hypertension (e.g., variceal hemorrhage, encephalopathy or ascites).
   b) History of liver transplantation, current placement on a liver transplant list or current Model for End Stage Liver Disease (MELD) score ≥12.
   c) Cirrhosis with complications, including history or presence of: spontaneous bacterial peritonitis, hepatocellular carcinoma, hyperbilirubinemia >1.5×ULN.
   d) Hepatorenal syndrome (type I or II).
   e) Splenomegaly.
3. Medical conditions that may cause non-hepatic increases in ALP (e.g., Paget's disease).
4. No evidence of worsening liver function during the screening period.
5. Patients who have donated any blood, or had significant blood loss within 30 days prior to screening.
6. Clinically significant infections (e.g., pneumonia, pyelonephritis) as judged by the investigator with an end date less than 6-weeks prior to treatment start (Day 1). In case of infection requiring hospitalization or intravenous antimicrobial therapy, or opportunistic infections, those infections must have ended at least 8 weeks prior to Day 1.
7. Infection with hepatitis C virus anytime in the past; confirmed active infection with hepatitis B virus at screening.
8. Current active or latent tuberculosis (TB) or history of TB that has not been successfully treated. In case of documented successful treatment in the past and current positivity of the QuantiFERON® test this criterion may be assessed on a case by case basis with medical monitor.
9. A positive diagnostic TB test at screening defined as a positive QuantiFERON® test or 2 successive indeterminate QuantiFERON® tests.
10. Agents used for the treatment of any condition listed in the exclusionary enrollment criteria from 30 days prior to Day 1.
11. Exposure to B cell or T cell targeted therapies (such as natalizumab, rituximab, abatacept, ustekinurnab) within 30 days prior to Day 1.
12. Azathioprine, colchicine, or methotrexate within 30 days prior to Day 1.
13. Treatment with obeticholic acid (OCA) or fibrates (including bezafibrate) within 30 days prior to Day 1.
14. Other immunosuppressive, immunomodulating or antineoplastic agents within 30 days prior to Day 1 (or not meeting the stability time period for concomitant medications indicated as permitted). However, medications (such as for pruritus and fatigue) used as adjunctive therapy for PBC in combination with UDCA should be at stable doses within 30 days prior to Day 1. These medications may be adjusted during study treatment, but all adjustments must be recorded in the concomitant medications source documents and eCRFs.

Drugs not allowed per the UDCA prescribing information: agents used for the treatment of any condition listed in the exclusionary enrollment criteria within 30 days prior to Day 1; Exposure to B cell or T cell targeted therapies (such as natalizumab, rituximab, abatacept, ustekinumab) within 30 days prior to Day 1 and during the study; azathioprine, colchicine, or methotrexate within 30 days prior to Day 1 and during the study; fibrates (including bezafibrate) within 30 days prior to Day 1 and during the study; treatment with OCA within 30 days prior to Day 1 and during the study; immunosuppressive, immunomodulating agents such as 5-ASA, azathioprine, colchicine, or methotrexate due to the potential impact on ALP; use of moderate to strong inhibitors of CYP2C9 (e.g., amiodarone, felbamate, fluconazole, miconazole, piperine, diosmin, disulfiram . . . m, fluvastatin, fluvoxamine, voriconazole) within 30 days prior to Day 1; receipt of live vaccine from 30 days prior to Day 1 (and for at least 6 months after the last dose of study drug); receipt of any investigational agent (including S1P modulators) within 30 days or 5 half-lives (whichever is longer), prior to Day 1; investigational agents, other than Compound 1 from 30 days prior to Day 1 and during the study; and receipt of any other medications that in the opinion of the investigator precludes patient from the safe participation in the study.

15. Use of moderate to strong inhibitors of CYP2C9 (e.g., amiodarone, felbamate, fluconazole, miconazole, piperine, diosmin, disulfiram, fluvastatin, fluvoxamine, voriconazole) within 30 days prior to Day 1.

16. Patients without documented positive varicella zoster virus (VZV) IgG-antibody status or patients who have not completed VZV vaccination within 6 weeks prior to Day 1.

17. Receipt of live vaccine within 30 days prior to Day 1 (and for at least 6 months after the last dose of study drug).

18. Receipt of any investigational agent (including S P modulators) within 30 days or 5 half-lives (whichever is longer), prior to Day 1.

19. Receipt of any other medication that in the opinion of the investigator precludes patients from the safe participation in the study.

20. Abnormal forced expiratory volume ($FEV_1$) or forced vital capacity (FVC), i.e., <80% of predicted values at screening.

21. Any known history of congenital or acquired immunodeficiency (e.g., common variable immunodeficiency, human immunodeficiency virus [HIV] infection [ELISA and Western blot] test result, organ transplantation).

22. Recent history (within 6 months of screening visit) of cardio- or cerebrovascular disease, acute coronary syndrome (ACS), myocardial infarction (MI), cardiomyopathy, heart failure, unstable angina, cerebro-vascular accident, including transient ischemic attack (TIA).

23. History or presence of cardiac arrhythmia, conduction system disease (including AV node dysfunction, 2nd or 3rd degree heart block, and sick sinus syndrome), or use of Class Ia or Class III anti arrhythmic agents, or baseline QTc ≥500 msec.

24. Any surgical procedure requiring general anesthesia within 30 days prior to Day 1 or plans to undergo major surgery during the study period.

25. History or presence of retinal macular edema.

26. History of or signs and symptoms of progressive multifocal leukoencephalopathy (PML) as assessed by the PML checklist at screening. If PML is suspected, withhold dosing and refer to a neurologist; if confirmed, discontinue dosing permanently.

27. History of more than one episode of herpes zoster or any episode of disseminated zoster.

28. History of lymphoproliferative disorder, lymphoma, leukemia, myeloproliferative disorder, or multiple myeloma.

29. Leukopenia or lymphopenia at screening.

30. History of malignancy except for adequately treated basal cell skin cancer and in situ carcinoma of the cervix or of the uterus that have been completely excised with documented, clear margins.

31. History of severe allergic or anaphylactic reactions requiring medical attention.

32. History of uncontrolled hypothyroidism.

33. Current or recent history (within 1 year prior to Day 1) of alcohol dependence or illicit drug use.

34. Active psychiatric disorders that, in the investigator's opinion, may interfere with compliance with the study procedures.

35. History of any other clinically significant medical condition that, in the investigator's opinion, would preclude patients from safe participation in the study.

36. Inability to attend all the study visits or comply with study procedures.

Example 3: BET (Brunauer, Emmett, and Teller) Specific Surface Area Method (Plate Habit)

In general, the specific surface areas for crystalline free-plate habit of the non-solvated L-arginine salt of Compound 1 were determined by physical adsorption of nitrogen gas on the surface of the sample from each lot using the well-established technique based on the Brunauer, Emmett, and Teller theory.

The BET surface areas for the samples were measured by Micromeritics Pharmaceutical Services using a Micromeritics™ TriStar IT BET surface area analyzer (MicroActive for TriStar II Plus 2.02 Software™). The samples were degassed at 25° C. for 960 minutes under vacuum (i.e., 100 mm/Hg). The determination of the adsorption of N, at 77.3 K was measured using a BET surface area eleven-point method with relative pressures in the range of about 0.05 to about 0.3 ($P/P_0$) for a weighed amount of each sample, see Table 1 below. The analysis was performed per ISO9277.

TABLE 1

| Arena Lot Number | Lot Number | Sample (g) | Correlation Coefficient | BET Surface Area ($m^2/g$) | Isolated Morphology | DSC Onset Temperature |
|---|---|---|---|---|---|---|
| 5015-12-12 | A1 | 0.6163 | 0.99916 | 0.7 | Plates | 208.09° C. |
| 5015-12-13 | A2 | 1.5270 | 0.99945 | 0.7 | Plates | 207.20° C. |
| 5015-12-14 | A3 | 0.4465 | 0.99922 | 1.5 | Plates | 207.19° C. |
| 5015-12-15 | A4 | 0.5709 | 0.99939 | 1.0 | Plates | 207.83° C. |
| 5015-12-16 | A5 | 0.9582 | 0.99940 | 0.8 | Plates | 207.90° C. |
| 04GSp | A6 | 0.4332 | 0.99921 | 2.4 | Plates | 206.55° C. |
| 05GSp | A7 | 0.3652 | 0.9991 | 1.9 | Plates | 206.94° C. |
| 06GSp | A8 | 0.6866 | 0.99984 | 3.0 | Plates | 207.04° C. |
| 07GSp | A9 | 0.2754 | 0.99914 | 3.1 | Plates | 207.63° C. |

Figure 7:
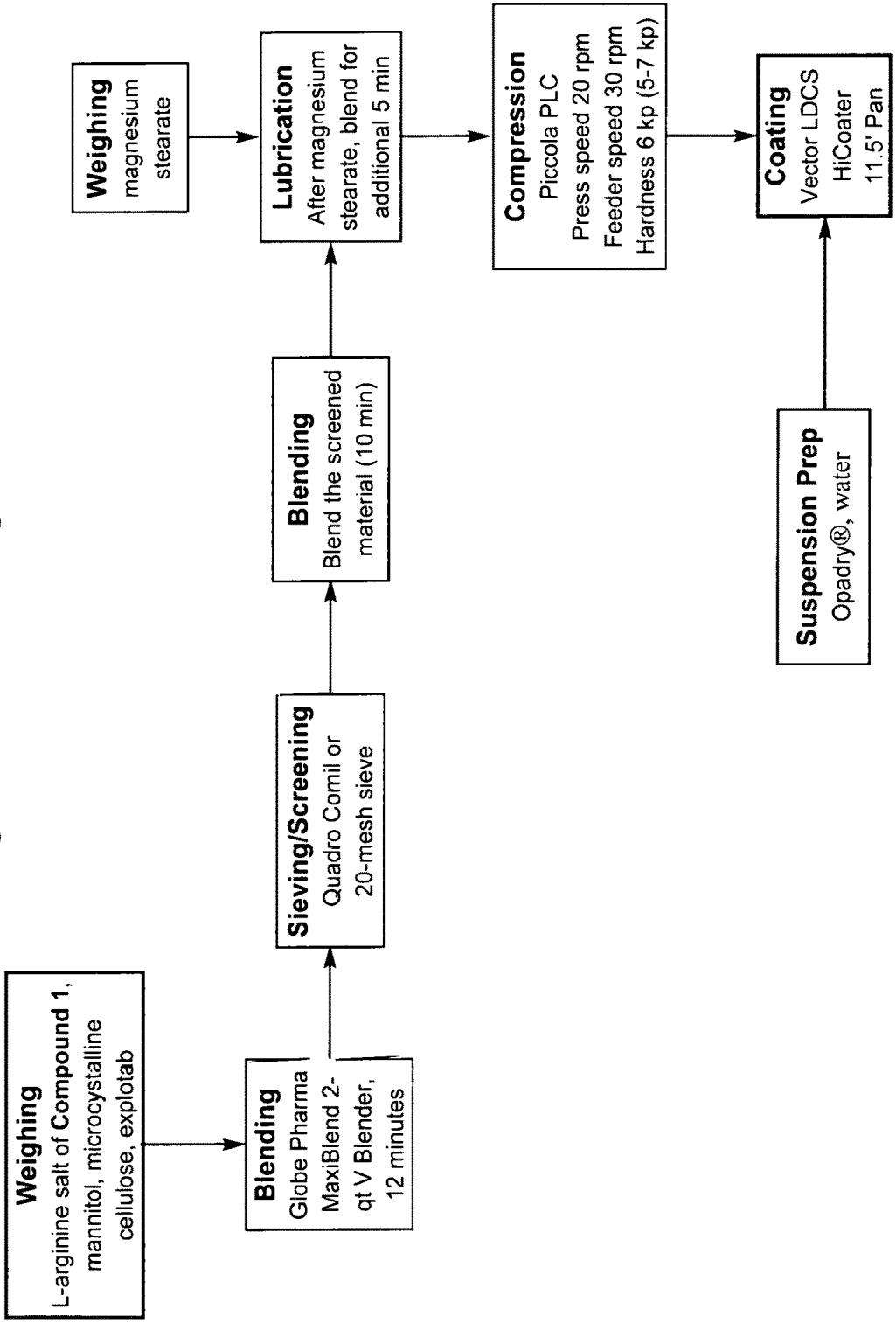
FIG. 7 shows a flowchart for the preparation of core tablets of the L-arginine salt of (R)-2-(7-(4-cyclopentyl-3-(trifluoromethyl)benzyloxy)-1,2,3,4-tetrahydrocyclopenta[b]indol-3-yl)acetic acid (Compound 1).

Example 4: Formulations for L-Arginine Salt of (R)-2-(7-(4-Cyclopentyl-3-(trifluoromethyl)-benzyloxy)-1,2,3,4-tetrahydrocyclopenta[b]indol-3-yl) acetic Acid Core tablets were manufactured using the formulation as described in Table 2 and using substantially the same process as described in FIG. 7. The L-arginine salt of (R)-2-(7-(4-cyclopentyl-3-(trifluoromethyl)benzyloxy)-1,2,3,4-tetrahydrocyclopenta[b]indol-3-yl)acetic acid is 72.42% free acid (Compound 1) and 27.58% L-arginine (i.e., 1.381 mg of the L-arginine salt of Compound 1 corresponds to 1 mg of active/free acid).

TABLE 2

| Tablet Strength | 1 mg | 2 mg |
| --- | --- | --- |
| L-Arg Salt of Compound 1 | 1.381 | 2.762 |
| Mannitol Pearlitol ® 100SD | 54.119 | 52.738 |
| Microcrystalline cellulose - Avicel ® | 40 | 40 |
| Sodium Starch Glycolate - Explotab ® | 4 | 4 |
| Magnesium Stearate | 0.5 | 0.5 |
| Opadry ® II Blue | 4 | 4 |
| Total tablet target weight | 104 | 104 |

Those skilled in the art will recognize that various modifications, additions, substitutions, and variations to the illustrative examples set forth herein can be made without departing from the spirit of the invention and are, therefore, considered within the scope of the invention.

What is claimed is:

1. A method of treating primary biliary cholangitis (PBC) in an individual in need thereof comprising administering a therapeutically effective amount of (R)-2-(7-(4-cyclopentyl-3-(trifluoromethyl)benzyloxy)-1,2,3,4-tetrahydrocyclopenta[b]indol-3-acetic acid (Compound 1), or a pharmaceutically salt, solvate, or hydrate thereof, wherein the individual is currently treated with a therapeutically effective amount of ursodeoxycholic acid (UDCA), wherein Compound 1 is administered without food.

2. The method according to claim 1, wherein the individual was previously treated with a therapeutically effective amount of ursodeoxycholic acid (UDCA).

3. The method according to claim 1, wherein the individual was previously treated with ursodeoxycholic acid (UDCA) and the individual had an inadequate response to UDCA.

4. The method according to claim 1, wherein the individual has at least one primary biliary cholangitis diagnosis criteria selected from the group consisting of:
anti-mitochondrial antibody (AMA) titer >1:40;
alkaline phosphate (ALP) >1.5 x ULN for at least 6 months; and
liver biopsy findings consistent with PBC.

5. The method according to claim 1, wherein the individual has at least one of the criteria selected from the group consisting of:
ALP >1.67 x ULN but <10 x ULN;
ALT and AST <5 x ULN;
total bilirubin <ULN;
international normalized ratio (INR)<1.2 x ULN;
platelet count >150,000/mm³;
serum albumin >3.0 g/dL;
serum creatinine <1.5 mg/dL (133 µmol/L);
TSH <5.0 mU/L without clinical significant changes of free T3 and T4 levels; and
Fibroscan® (transient elastography)<10 kPa.

6. The method according to claim 1, wherein the therapeutically effective amount of Compound 1, or a pharmaceutically acceptable salt, hydrate, or solvate thereof, is administered orally.

7. The method according to claim 1, wherein the Compound 1, or a pharmaceutically acceptable salt, hydrate, or solvate thereof, is formulated as a capsule or tablet suitable for oral administration.

8. The method according to claim 1, wherein the therapeutically effective amount of Compound 1, or a pharmaceutically acceptable salt, hydrate, or solvate thereof, is in an amount equivalent to about 1.0 mg to about 5 mg of Compound 1.

9. The method according to claim 1, wherein the therapeutically effective amount of Compound 1, or a pharmaceutically acceptable salt, hydrate, or solvate thereof, is in an amount equivalent to about 1 mg to about 2 mg.

10. The method according to claim 1, wherein the therapeutically effective amount of Compound 1, or a pharmaceutically acceptable salt, hydrate, or solvate thereof, is in an amount equivalent to about 1 mg, about 1.25 mg, about 1.5 mg, about 1.75 mg, or about 2 mg of Compound 1.

11. The method according to claim 1, wherein the therapeutically effective amount of Compound 1, or a pharmaceutically acceptable salt, hydrate, or solvate thereof, is in an amount equivalent to about 1 mg of Compound 1.

12. The method according to claim 1, wherein the therapeutically effective amount of Compound 1, or a pharmaceutically acceptable salt, hydrate, or solvate thereof, is in an amount equivalent to about 2 mg of Compound 1.

13. The method according to claim 1, wherein the therapeutically effective amount of Compound 1, or a pharmaceutically acceptable salt, hydrate, or solvate thereof, is administered once daily.

14. The method according to claim 1, wherein the Compound 1, or a pharmaceutically acceptable salt, hydrate, or solvate thereof, is an L-arginine salt of Compound 1.

15. The method according to claim 1, wherein the Compound 1, or a pharmaceutically acceptable salt, hydrate, or solvate thereof, is an anhydrous, non-solvated crystalline form of the L-arginine salt of Compound 1.

16. The method according to claim 1, wherein the Compound 1, or a pharmaceutically acceptable salt, hydrate, or solvate thereof, is a crystalline free-plate habit of the non-solvated L-arginine salt of Compound 1.

17. The method according to claim 1, further comprising administering Compound 1, or a pharmaceutically salt, solvate, or hydrate thereof, in combination with a therapeutically effective amount of with a compound selected from the group consisting of: an antihistamine, cholestyramine, rifampin, an opioid antagonist, pilocarpine, cevimeline, calcium and/or vitamin D supplement, and vitamin A, D, E and/or K supplement.

18. A method of treating fatigue, pruritus, eye dryness, and/or Sjögren's syndrome (SS) in an individual with primary biliary cholangitis (PBC) comprising administering a therapeutically effective amount of (R)-2-(7-(4-cyclopentyl-3-(trifluoromethyl)benzyloxy)-1,2,3,4-tetrahydrocyclopenta[b]indol-3-acetic acid (Compound 1), or a pharmaceutically salt, solvate, or hydrate thereof,
wherein the individual is currently treated with a therapeutically effective amount of ursodeoxycholic acid (UDCA), wherein Compound 1 is administered without food.

* * * * *